US007803363B2

(12) United States Patent
Klose et al.

(10) Patent No.: US 7,803,363 B2
(45) Date of Patent: Sep. 28, 2010

(54) ATTENUATED *FRANCISELLA* BACTERIA

(75) Inventors: Karl E. Klose, San Antonio, TX (US);
Bernard P. Arulanandam, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 11/680,375

(22) Filed: Feb. 28, 2007

(65) Prior Publication Data

US 2007/0248622 A1    Oct. 25, 2007

Related U.S. Application Data

(60) Provisional application No. 60/780,692, filed on Mar. 9, 2006, provisional application No. 60/777,682, filed on Feb. 28, 2006.

(51) Int. Cl.
*A61K 39/02* (2006.01)
(52) U.S. Cl. .................. 424/93.2; 424/93.4; 435/440
(58) Field of Classification Search ................ None
See application file for complete search history.

(56) References Cited

U.S. PATENT DOCUMENTS

| | | | | |
|---|---|---|---|---|
| 4,596,792 | A | 6/1986 | Vyas ........................ 512/21 |
| 4,599,230 | A | 7/1986 | Milich et al. ................ 424/89 |
| 4,599,231 | A | 7/1986 | Milich et al. ................ 424/88 |
| 4,601,903 | A | 7/1986 | Frasch et al. ................ 424/92 |
| 4,608,251 | A | 8/1986 | Mia et al. .................... 424/85 |
| 5,643,771 | A | 7/1997 | Stocket et al. ........... 435/172.3 |
| 6,254,874 | B1 | 7/2001 | Mekalanos et al. ....... 424/234.1 |
| 2004/0197343 | A1 | 10/2004 | Dubensky et al. ........ 424/184.1 |

FOREIGN PATENT DOCUMENTS

WO    WO 2004/084935    10/2004

OTHER PUBLICATIONS

Clements et al. (Vaccine, 20:S24-S33, 2002).*
Barker et al. (Abstract B-139, 105th ASM General Meeting, Jun. 7, 2005).*
PCT International Search Report and Written Opinion, issued in International Application No. PCT/US 07/63004, dated Oct. 29, 2007.
Abd et al., "Survival and Growth of *Francisella tularensis* in *Acanthamoeba castellanii*," *Applied Environment Microbiology*, 69:600-606, 2003.
Allen, "Immunity Against Turlaremia: Passive Protection of Mice by Transfer of Immune Tissues," *J. Exp. Med.*, 115:411-420, 1962.
Anthony et al., "Growth of *Francisella* spp. In Rodent Macrophages," *Infection and Immunity*, 59:3291-3296, 1991.
Anthony et al., "The requirement for gamma interferon in resistance of mice to experimental tularemia," *Microbial. Pathogenesis*, 7:421-428, 1989.
Arulanandam et al., "Intranasal Vaccination with Pneumococcal Surface Protein A and Interleukin-12 Augments Antibody-Mediated Opsonization and Protective Immunity against *Streptococcus pneumoniae* Infection," *Infection and Immunity*, 69:6718-6724, 2001.
Badger and Miller, "Expression of Invasin and Motility Are Coordinately Regulated in *Yersinia enterocolitica*," *Journal of Bacteriology*, 180:793-800, 1998.
Barker et al., "MglA regulates transcription of virulence factors necessary for *Francisella tularensis* intra-amoeba and intra-macrophage survival," www.asmbiodefense.org/2004monabs.asp, Jun. 22, 2005.
Baron and Nano, "An erythromycin resistance cassette and mini-transposon for constructing transcriptional fusions to cat," *Gene*, 229:59-65, 1999.
Baron and Nano, "MgIA and MgIB are required for the intramacrophage growth of *Francisella novicida*," *Molecular Microbiology*, 29:247-259, 1998.
Bosio and Elkins, "Susceptibility to Secondary *Francisella tularensis* Live Vaccine Strain Infection in B-Cell-Deficient Mice is Assocaited with Neutrophilia but Not with Defects in Specific T-Cell-Mediated Immunity," *Infection and Immunity*, 69:194-203, 2001.
Broekhuijsen et al., "Genome-Wide DNA Microarray Analysis of *Francisella tularensis* Strains Demonstrates Extensive Genetic Conservation within the Species but Identifies Regions that are Unique to the Highly Virulent *F. tularensis* subsp. *tularensis*," *Journal of Clinical Microbiology*, 41:2924-2931, 2003.
Casadevall, "Antibody-mediated protection against intracellular pathogens," *Trends Microbiology*, 6:102-107, 1998.
Christopher et al., "Biological Warfare: A Historical Perspective," *JAMA*, 278:412-417, 1997.
Clemens et al., "Virulent and Avirulent Strains of *Francisella tularensis* Prevent Acidification and Maturation of Their Phagosomes and Escape into the Cytoplasm in Human Macrophages," *Infection and Immunity*, 72:3204-3217, 2004.
Collins and Dunnick, "Germline transcripts of the murine immunoglobin γ2a gene: structure and induction by IFN-γ," *International Immunology*, 5:885-891, 1993.
Conlan et al., "CD4 and CD8 T-Cell-Dependent and -Independent Host Defense Mechanisms Can Operate to Control and Resolve Primary and Secondary *Francisella tularensis* LVS Infection in Mice," *Infection and Immunity*, 62:5603-5607, 1994.
Conlan, "Vaccines against *Francisella tularensis*-past, present and future," *Expert Reviews Vaccines*, 3:307-314, 2004.
Cooper et al., "IFN-γ and NO In mycobacterial disease: new jobs for old hands," *Trends in Microbiology*, 10:221-226, 2002.
Cowley et al., "Phase variation in *Francisella tularensis* affecting intracellular growth, lipopolysaccharide antigenicity and nitric oxide production," *Molecular Microbiology*, 20:867-874, 1996.
Cronquist, "Tularemia: the disease and the weapon," *Dermatologic Clinics*, 22:313-320, 2004.

(Continued)

*Primary Examiner*—Robert B Mondesi
*Assistant Examiner*—Brian J Gangle
(74) *Attorney, Agent, or Firm*—Fulbright & Jaworski L.L.P.

(57) ABSTRACT

In one embodiment, there is disclosed a method of inducing an immune response in a subject comprising administering to the subject a *Francisella* bacterium that includes an alteration in the nucleic acid sequence encoding the mglA, iglA, iglB, iglC, or iglD gene of the bacterium.

12 Claims, 4 Drawing Sheets

OTHER PUBLICATIONS

De Reuse and Taha, "RegF, an SspA homologue, regulates the expression of the *Neisseria gonorrhoeae pilE* gene,"*Res. Microbiol.*, 148:289-303, 1997.

Dennis et al., "Tularemia as a Biological Weapon," *JAMA*, 285:2763-2773, 2001.

Ding et al., "Role of SspA in the density-dependent expression of the transcriptional activator AarP in *Providencia stuartii*," *FEMS Microbiology Letters*, 196:25-29, 2001.

DiRita et al., "Regulatory cascade controls virulence in *Vibrio cholerae*," *Proc. Natl. Acad. Sci. USA*, 88:5403-5407, 1991.

Edelson and Unanue, "Intracellular Antibody Neutralizes *Listeria* Growth," *Immunity.*, 14:503-512, 2001.

Eigelsbach and Downs, "Prophylactic Effectiveness of Live and Killed Tularemia Vaccines," *J. Immunol.*, 87:415-425, 1961.

Elkins et al., "*Francisella*: a little bug hits the big time," *Expert Review of Vaccines*, 2:735-738, 2003.

Elkins et al., "Importance of B cells, but Not Specific Antibodies, in Primary and Secondary Protective Immunity to the Intracellular Bacterium *Francisella tularensis* Live Vaccine Strain," *Infection and Immunity*, 67:6002-6007, 1999.

Elkins et al., "Innate and adaptive immune responses to an intracellular bacterium, *Francisella tularensis* live vaccine strain," *Microbes and Infection*, 5:135-142, 2003.

Elkins et al., "Minimal Requirements for Murine Resistance to Infection with *Francisella tularensis* LVS," *Infection and Immunity*, 64:3288-3293, 1996.

Elkins et al., "Nonspecific Early Protective Immunity in *Francisella* and *Listeria* Infections Can Be Dependent on Lymphocytes," *Infection and Immunity*, 66:3467-3469, 1998.

Elkins et al., "T-Cell-Independent Resistance to Infection and Generation of Immunity to *Francisella tularensis*," *Infection and Immunity*, 61:823-829, 1993.

Ellis et al., "Tularemia," *Clinical Microbiology Reviews*, 15:631-646, 2002.

Feldman et al., "An Outbreak of Primary Pneumonic Tularemia on Martha's Vineyard," *The New England Journal of Medicine*, 345:1601-1606, 2001.

Forsman et al., "Analysis of 16S Ribosomal DNA Sequences of *Francisella* Strains and Utilization for Determination of the Phylogeny of the Genus and for Identification of Strains by PCR," *International Journal of Systematic Bacteriology*, 44:38-46, 1994.

Fortier et al., "Life and Death of an Intracellular Pathogen: *Francisella tularensis* and the Macrophage," *Immunology Series.*, 60:349-361, 1994.

*Francisella tularensis* subsp. *novicida* U112, GenBank Accession No. AAP58964, 2002.

*Francisella tularensis* subsp. *novicida* U112, GenBank Accession No. AF045772, 1998.

*Francisella tularensis* subsp. *novicida* U112, GenBank Accession No. AY293579, 2002.

Fulop et al., "Role of antibody to lipopolysaccharide in protection against low- and high-virulence strains of *Francisella tularensis*," *Vaccine*, 19:4465-4472, 2001.

Gao et al., "Utilization of Similar Mechanisms by *Legionella pneumophila* to Parasitize Two Evolutionary Distant Host Cells, Mammalian Macrophages and Protozoa," *Infection and Immunity*, 65:4738-4746, 1997.

Golovliov et al., "A method for allelic replacement in *Francisella tularensis*," *FEMS Microbiology Letters*, 222:273-280, 2003.

Gray et al., "The identification of five genetic loci of *Francisella novicida* associated with intracellular growth," *FEMS Microbiological Letters*, 215, 53-56, 2002.

Greenfield and Bronze, "Current therapy and the development of therapeutic options for the treatment of diseases due to bacterial agents of potential biowarfare and bioterrorism," *Current Opinion in Investigational Drugs*, 5:135-140, 2004.

Groisman et al., "*Salmonella typhimurium phoP* virulence gene is a transcriptional regulator," *Proc. Natl. Acad. Sci. USA*, 86:7077-7081, 1989.

Hansen et al., "*Escherichia coli* SspA is a transcription activator for bacteriophage P1 late genes," *Molecular Microbiology*, 48:1621-1631, 2003.

Harb et al., "From protozoa to mammalian cells: a new paradigm in the life cycle of intracellular bacterial pathogens," *Environmental Microbiology*, 2:251-265, 2000.

Harris, "Japanese Biological Warefare Research on Animals: A Case Study of Microbiology and Ethics," *Annals New York Academy of Science*, 666:21-52, 1992.

Hornick et al., "Aerogenic Immunization of Man with Live Tularemia Vaccine," *Bacteriological Reviews*, 30:532-538, 1966.

Igietseme et al., "Antibody regulation of T-cell immunity: implications for vaccine strategies against intracellular pathogens," *Expert. Rev. Vaccines*, 3:23-34, 2004.

Isherwood et al., "Vaccination strategies for *Francisella tularensis*," *Advanced Drug Delivery Reviews*, 57:1403-1414, 2005.

Jackson et al., "Safety of a trivalent live attenuated intranasal influenza vaccine, FluMist™, administered in addition to parenteral trivalent inactivated influenza vaccine to seniors with chronic medical conditions," *Vaccine*, 17:1905-1909, 1999.

Kieffer et al., "*Francisella novicida* LPS has greater immunobiological activity in mice than *F. tularensis* LPS, and contributes to *F. novicida* murine pathogenesis," *Microbes and Infection*, 5:397-403, 2003.

Kipps et al., "Importance of Immunoglobulin Isotype in Human Antibody-Dependent, Cell-Mediated Cytotoxicity Directed by Murine Monoclonal Antibodies," *The Journal of Experimental Medicine*, 161:1-17, 1985.

Lai et al., "Expression of IgIC is necessary for intracellular growth and induction of apoptosis in murine macrophages by *Francisella tularensis*," *Microbial Pathogenesis*, 37:225-230, 2004.

Lai et al., "*Francisella tularensis* Induces Cytopathogenicity and Apoptosis in Murine Macrophages via a Mechanism that Requires Intracellular Bacterial Multiplication," *Infection and Immunity*, 69:4691-4694, 2001.

Lauriano et al., "Allelic exchange in *Francisella tularensis* using PCR products," *FEMS Microbiological Letters*, 229:195-202, 2003.

Lauriano et al., "Intranasal vaccination with *Francisella tularensis* subsp. *novicida* IgIC confers protective immunity against pulmonary tularemia," $12^{th}$ *International Congress in Mucosal Immunology*, Abstract # 53291, 2005.

Lauriano et al., "MgIA regulates transcription of virulence factors necessary for *Francisella tularensis* intraamoebae and intramacrophage survival," *Proceedings of the National Academy of Science of the USA*, 101:4246-4249, 2004.

Leiby et al., "In Vivo Modulation of the Murine Immune Response to *Francisella tularensis* LVS by Administration of Anticytokine Antibodies," *Infection and Immunity*, 60:84-89, 1992.

Lenco et al., "Insights into the oxidative stress response in *Francisella tularensis* LVS and its mutant ΔiglC1+2 by proteomics analysis," *FEMS Microbiology Letters*, 246:47-54, 2005.

Li and Winslow, "Survival, Replication, and Antibody Susceptibility of *Ehrlichia chaffeensis* Outside of Host Cells," *Infection and Immunity*, 71:4229-4237, 2003.

Lindgren et al., "Factors affecting the escape of *Francisella tularensis* from the phagolysosome," *Journal of Medical Microbiology*, 53:953-958, 2004.

Miller et al., "A two-component regulatory system (phoP phoQ) controls *Salmonella typhimurium* virulence," *Proceedings of the National Academy of Science of the USA*, 86:5054-5058, 1989.

Moore et al., "Fc receptor regulation of protective immunity against *Chlamydia trachomatis*," *Immunology*, 105:213-221, 2002.

Murthy et al., "*Chlamydia trachomatis* pulmonary infection induces greater inflammatory pathology in immunoglobulin A deficient mice," *Cell Immunology*, 230:56-64, 2004.

Nano et al., "A *Francisella tularensis* Pathogenicity Island Required for Intramacrophage Growth," *Journal of Bacteriology*, 186:6430-6436, 2004.
Neuberger and Rajewsky, "Activation of mouse complement by monoclonal mouse antibodies," *European Journal of Immunology*, 11:1012-1016, 1981.
Oyston and Quarry "Tularemia vaccine: past, present and future," *Antonie van Leeuwenhoek*, 87:277-281, 2005.

Pammit et al., "Intranasal Interleukin-12 Treatment Promotes Antimicrobial Clearance and Survival in Pulmonary *Francisella tularensis* subsp. *novicida* Infection," *Antimicrobial Agents and Chemotherapy*, 48:4513-4519, 2004.

Pammit et al., "Intranasal Vaccination with a Defined Attenuated *Francisella novicida* Strain Induces Gamma Interferon-Dependent Antibody-Mediated Protection against Tularemia," *Infection and Immunity*, 74:2063-2071, 2006.

Ravetch and Clynes, "Divergent Roles for Fc Receptors and Complement in Vivo," *Annual Review of Immunology*, 16:421-432, 1998.

Rhinehart-Jones et al., "Transfer of Immunity against Lethal Murine *Francisella* Infection by Specific Antibody Depends on Host Gamma Interferon and T Cells," *Infection and Immunity*, 62:3129-3137, 1994.

Santic et al., "Modulation of biogenesis of the *Francisella tularensis* subsp. *novicida*-containing phagosome in quiescent human macrophages and its maturation into a phagolysosome upon activation by IFN-$\gamma$," *Cell Microbiology*, 7:957-967, 2005.

Santic et al., "The *Francisella tularensis* pathogencity island protein IgIC and its regulator MgIA are essential for modulating phagosome biogenesis and subsequent bacterial escape into the cytoplasm," *Cellular Microbiology*, 7:969-979, 2005.

Saslaw et al., "Aseptic Meningitis and Nonparalytic Poliomyelitis," *Arch. Intern. Med.*, 107568-571, 1960.

Shen et al., "Mice sublethally infected with *Francisella novicida* U112 develop only marginal protective immunity against systemic or aerosol challenge with virulent type A or B strains of *F. tularensis*," *Microbial Pathogenesis*, 37:107-110, 2004.

Sjostedt et al., "The requirement of tumour necrosis factor-alpha and interferon-gamma for the expression of protective immunity to secondary murine tularaemia depends on the size of the challenge inoculum," *Microbiology*, 142:1369-1374, 1996.

Stenmark et al., "Specific antibodies contribute to the host protection against strains of *Francisella tularensis* subspecies *holarctica*," *Microbial Pathogenesis*, 35:73-80, 2003.

Stuart and Pullen, "Tularemic Pneumonia: Review of American Literature and Report of 15 Additional Cases," *Am. J. Med. Sci.*, 210:223-236, 1945.

Syrjala et al., "Bronchial changes in airborne tularemia," *The Journal of Laryngology and Otology*, 100:1169-1176, 1986.

Takai et al., "FcR-gamma Chain Deletion Results in Pleiotrophic Effector Cell Defects," *Cell*, 76:519-529, 1994.

Tarnvik, "Nature of Protective Immunity to *Francisella tularensis*," *Reviews of Infectious Diseases*, 11:440-451, 1989.

Telepnev et al., "*Francisella tularensis* inhibits Toll-like receptor-mediated activation of intracellular signalling and secretion of TNF-$\alpha$ and IL-1 from murine macrophages," *Cell Microbiology*, 5:41-51, 2003.

Titball and Oyston, "A vaccine for tularaemia," *Expert Opinion on Biological Therapy*, 3:645-653, 2003.

Titball et al., "Will the enigma of *Francisella tularensis* virulence soon be solved?," *Trends Microbiology*, 11:118-123, 2003.

Trinchieri, "Interleukin-12 and the Regulation of Innate Resistance and Adaptive Immunity," *Nature Reviews Immunology*, 3:133-146, 2003.

Unkeless et al., "Structure and Function of Human and Murine Receptors for IgG," *Annu. Rev. Immuno.* 6:251-281, 1988.

Vinogradov et al., "Structural analysis of *Francisella tularensis* lipopolysaccharide," *Eur. J. Biochem.*, 269:6112-6118, 2002.

Vogel et al., "Conjugative Transfer by the Virulence System of *Legionella pneumophila*," *Science*, 279:873-876, 1998.

Vogel, "An Obscure Weapon of the Cold War Edges Into the Limelight," *Science*, 302:222-223, 2003.

Walker, "New strategies for using mucosal vaccination to achieve more effective immunization," *Vaccine*, 12:387-400, 1994.

White et al., "Pathogensis of experimental respiratory tularemia in monkeys," The Journal of Infectious Diseases, 114:277-283, 1964.

Williams et al., "Glutathione S-Transferase-SSPA Fusion to *E. coli* RNA Polymerase and Complements $\Delta$sspA Mutation Allowing Phage P1 Replication," *Biochemical and Biophysical Research Communication*, 201:123-127, 1994.

Winslow et al., "Mechanisms of Humoral Immunity during *Ehrlichia chaffeensis* Infection," *Ann. N.Y. Acad. Sci.*, 990:435-443, 2003.

Wu et al., "Intranasal Vaccination Induces Protective Immunity against Intranasal Infection with Virulent *Francisella tularensis* Biovar A," *Infection and Immunity*, 73:2644-2654, 2005.

Yee et al., "Loss of Either CD4 or CD8 T Cells Does Not Affect the Magnitude or Protective Immunity to an Intracellular Pathogen, *Francisella tularensis* Strain LVS," *J. Immunolog.*, 157:5042-5048, 1996.

Yoon et al., "*Pseudomonas aeruginosa* Anaerobic Respiration in Biofilms: Relationships to Cystic Fibrosis Pathogenesis," *Developmental Cell*, 3:593-603, 2002.

\* cited by examiner

ATTENUATED *FRANCISELLA* BACTERIA

CROSS-REFERENCES TO RELATED APPLICATIONS

This application claims the benefit of U.S. Provisional Application No. 60/780,692, filed 9 Mar. 2006, and U.S. Provisional Application No. 60/777,682, filed 28 Feb. 2006. The contents of these applications are incorporated by reference.

STATEMENT REGARDING FEDERALLY SPONSORED RESEARCH

This invention was made with government support under grant numbers AI050564 and AI057156 awarded by the National Institutes of Health. The government has certain rights in the invention.

BACKGROUND OF THE INVENTION

A. Field of the Invention

The present invention concerns attenuated *Francisella* bacteria vaccines and methods of preventing and treating a *Francisella* infection.

B. Background of the Invention

*Francisella tularensis* is an intracellular Gram negative bacterium that can cause pneumonic tularemia in humans (Ellis et al., 2002; Tarnvik, 1989). *F. tularensis* subsp. *tularensis* is classified as one of the most infectious pathogenic bacteria because inhalation with only a few organisms will cause disease and significant mortality (Saslaw et al., 1961). *F. tularensis* also is considered a potential biological weapon and has been developed as a germ warfare agent by several government programs (Christopher et al., 1997; Dennis et al., 2001; Harris, 1992). Humans infected by *F. tularensis* usually acquire the disease by contact with infected animals, vectors (ticks), exposure to contaminated food and water, or aerosol exposure (Feldman et al., 2001; Tarnvik, 1989).

To date, *F. tularensis* live vaccine strain (LVS), which is derived from *F. tularensis* subspecies *holarctica* (type B) has been the only vaccine candidate for tularemia. In humans (Saslaw et al., 1961) and in animals (Eigelsbach and Downs, 1961), vaccination with LVS has demonstrated varying degrees of protection against aerosolized and parenteral subsp. *tularensis* challenges. However, the basis of attenuation of the LVS strain is unknown, making its use in humans somewhat questionable given the uncertain probability of reversion to virulence of the vaccine strain.

SUMMARY OF THE INVENTION

The present invention overcomes the deficiencies in the art by providing compositions and methods for their use in live bacteria compositions. In certain aspects the live bacteria compositions contain attenuated bacteria for use in provoking an immune response to non-attenuated bacteria. Further aspects of the invention include vaccine comprising attenuated bacteria of the genus *Franscisella*, in particular the species *Francisella tularensis*. In still other aspects of the invention are directed to modified subspecies *F. tularensis novicida, F. tularensis tularensis,* or *F. tularensis holarctica*.

Embodiments of the invention include methods of inducing an immune response in a subject comprising administering to the subject a *Francisella* bacterium that includes an alteration in the nucleic acid sequence encoding the mglA, iglA, iglB, iglC, or iglD gene of the bacterium. In certain aspects the bacterium is attenuated. The alteration in the nucleic acid sequence can render the mglA, iglA, iglB, iglC, or iglD gene inactive. In one aspect the mglA gene is altered. In a second aspect the iglA gene is altered. In a third aspect the iglB gene is altered. In a fourth aspect the iglC gene is altered. In a fifth aspect the iglD gene is altered.

In a further embodiment the methods may include a bacterium with at least two, three, four, or five of the mglA, iglA, iglB, iglC, or iglD genes altered. In certain aspects all of the mglA, iglA, iglB, iglC, and iglD genes are altered. In other aspects one or more of the mglA, iglA, iglB, iglC, or iglD gene is not expressed. In still other aspects the bacterium lacks the mglA, iglA, iglB, iglC, or iglD gene. An alteration can be a deletion, substitution, or insertion mutation. In still further aspects of the invention the bacterium expresses an inactive mglA, iglA, iglB, iglC, or iglD protein. In certain aspects of the invention the bacterium is *F. tularensis*. The *F. tularensis* bacterium can be *F. tularensis tularensis* (Type A), *F. tularensis holarctica* (Type B), *F. tularensis mediaasiatica,* and *F. tularensis novicida*. In one aspect, *F. tularensis* is *F. tularensis tularensis* (Type A). In a second aspect, *F. tularensis* is *F. tularensis holarctica* (Type B). In a third aspect, *F. tularensis* is *F. tularensis mediaasiatica*. In a fourth aspect, *F. tularensis* is *F. tularensis novicida*. In a further aspect *F. tularensis novicida* is *F. tularensis novicida* strain KKF34 or KKF24. The bacterium of the invention can be comprised in a pharmaceutically acceptable composition. The composition can be formulated into a liquid, spray, or aerosol. The bacterium of the invention can be administered intravenously (e.g., by injection) or intranasally.

In yet another aspect the bacterium are incapable of replicating. In certain aspects bacterium is incapable of replicating in a cell. In a further aspect the bacterium is incapable of replicating in a macrophage or an amoebae. In a particular aspect the bacterium is incapable of replicating in an amoebae. In still a further aspect the bacterium is incapable of replicating in the subject. The subject can be an animal. The animal can be a human, mouse, rat, rabbit, cat, dog, pig, or cow. In particular aspects the animal is a human.

The methods of the invention may further include (a) producing a protective immune response in the subject; (b) preventing against or treating *Francisella* bacterial infection; (c) preventing against or treating pulmonary *Francisella* bacterial infection; (d) preventing a pulmonary challenge of *Francisella* bacterial infection; and/or (e) preventing or treating tularemia.

Methods of the invention include methods of preventing or treating *Francisella* bacterium infection comprising administering to a subject an attenuated *Francisella* bacterium that includes an alteration in the nucleic acid sequence encoding the mglA, iglA, iglB, iglC, or iglD gene of the bacterium.

Methods of the invention also include methods for producing an attenuated *Francisella* bacterium comprising introducing an alteration in the nucleic acid sequence encoding the mglA, iglA, iglB, iglC, or iglD gene of the bacterium. An alteration can include a deletion, substitution, or insertion mutation. In certain aspects one or more of the mglA, iglA, iglB, iglC, or iglD gene is not expressed. In other aspects of the invention the bacterium expresses one or more inactive mglA, iglA, iglB, iglC, or iglD protein. In still further aspects the bacterium lacks one or more of the mglA, iglA, iglB, iglC, or iglD gene. The bacterium or bacteria of the invention can be formulated into a pharmaceutically acceptable vaccine.

Further embodiments of the invention include methods of vaccination against a *Francisella* bacterium comprising administering to a subject an attenuated *Francisella* bacterium having a genome comprising an alteration in the nucleic acid sequence encoding one or more of the mglA, iglA, iglB, iglC, or iglD gene of the bacterium. The composition typically comprises a pharmaceutically acceptable formulation.

Still further embodiments of the invention include vaccine compositions comprising an attenuated *Francisella* bacterium with a genome that comprises an alteration in the nucleic acid sequence encoding the mglA, iglA, iglB, iglC, or iglD gene of the bacterium. Vaccine composition of the invention can comprise an adjuvant.

Yet still further embodiments of the invention include methods for inducing an immune response against a *Francisella* bacterium comprising administering to a subject an effective amount of a vaccine compositions described herein. The composition can be administered to the subject at least 2, 3, 4, 5, 6, 7, 8, 9, 10, or more times. In certain aspects of the invention an adjuvant is administered with the vaccine composition(s).

Embodiments of the invention include methods for producing a vaccine for a *Francisella* bacterial infection comprising generating or obtaining an attenuated *Francisella* bacterium that includes an alteration in the nucleic acid sequence encoding one or more of the mglA, iglA, iglB, iglC, or iglD gene of the bacterium and formulating a pharmaceutically acceptable composition comprising one or more bacterium encoding one or more altered genes.

Further embodiments of the invention include vaccine compositions comprising an immunologically protective amount of a first attenuated, non-reverting altered *Francisella* bacterium in which one or more of the mglA, iglA, iglB, iglC, or iglD gene has been inactivated.

Further embodiments of the invention include live attenuated vaccines for the protection of animals against infection with pathogenic *Francisella*, said live attenuated vaccine comprising: (a) a live attenuated *Francisella* bacterium that is incapable of expressing a functional mglA, iglA, iglB, iglC, or iglD protein, wherein the bacterium includes an alteration in the mglA, iglA, iglB, iglC, or iglD gene; and (b) an adjuvant. In certain aspects the bacterium can further comprise a heterologous gene. The vaccine will typically comprise sufficient attenuated *Francisella* bacteria to elicit an immune response in a subject.

Embodiments of the invention include methods of protecting a subject against infection with pathogenic *Francisella* bacteria comprising administering to the subject a live attenuated *Francisella* bacterium that is incapable of expressing a functional mglA, iglA, iglB, iglC, or iglD protein, wherein the bacterium includes an alteration in the mglA, iglA, iglB, iglC, or iglD gene.

The inventors also contemplates that equivalent genes (e.g., greater than 80% homology) in other gram negative bacteria can be similarly inactivated to provide efficacious vaccines.

"Inactivated" gene includes a gene that has been mutated by insertion, deletion or substitution, or a combination thereof of nucleotide sequence such that the mutation inhibits or abolishes expression and/or biological activity of the encoded gene product. The mutation may act through affecting transcription or translation of the gene or its mRNA, or the mutation may affect the polypeptide gene product itself in such a way as to render it inactive.

"Attenuated" includes a cell, culture, or strain of *Francisella* exhibiting a detectable reduction in infectivity or virulence in vitro or in vivo as compared to that of the parent strain of *Francisella* from which the attenuated cell, culture, or strain is derived. Reduction in virulence encompasses any detectable decrease in any attribute of virulence, including infectivity in vitro or in vivo, or any decrease in the severity or rate of progression of any clinical symptom or condition associated with infection.

In addition to immunizing the recipient, the vaccines of the invention may also promote growth of the recipient and/or boost the recipient's immunity and/or improve the recipient's overall health status.

The subject to be immunized may be a human or other mammal or animal, for example, farm animals including cows, sheep, pigs, horses, goats and poultry (e.g., chickens, turkeys, ducks and geese) and companion animals such as dogs and cats; exotic and/or zoo animals. Immunization of both rodents and non-rodent animals is contemplated.

It is contemplated that any embodiment discussed in this specification can be implemented with respect to any method or composition of the invention, and vice versa. Furthermore, compositions of the invention can be used to achieve methods of the invention.

The term "about" or "approximately" are defined as being close to as understood by one of ordinary skill in the art, and in one non-limiting embodiment the terms are defined to be within 10%, within 5%, within 1%, and within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Figure 1:
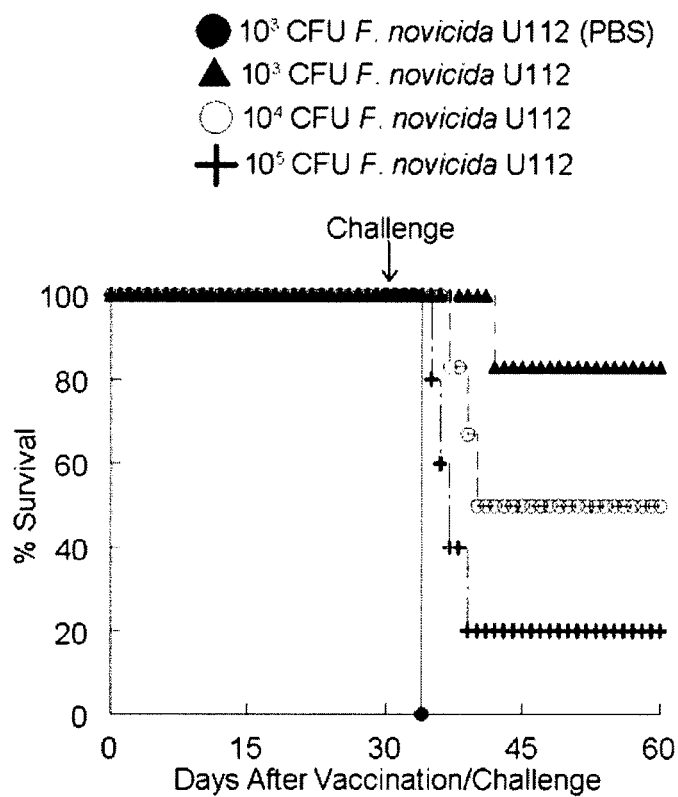
FIG. 1: Efficacy of intranasal vaccination with KKF24. BALB/c mice (6 mice/group) were anesthetized with 3% Isofluorane and vaccinated immediately i.n. with KKF24 (106 CFU) in 25 μl of sterile PBS. Unvaccinated mice received only PBS. All animals were challenged after 30 days with escalating inocula (100, 1000 and 10,000 $LD_{50}$) of wild type *F. tularensis* subsp. *novicida* U112. All animals were monitored daily for survival. Differences in survival between KKF24 vaccinated and mock-vaccinated mice were significant at p<0.001. Results are representative of 2 independent experiments.

F. tularensis can be classified into several subspecies, including those relevant to human disease: F. tularensis subsp. tularensis (type A) and F. tularensis subsp. holarctica (type B) (Titball et al., 2003). An additional subspecies, F. tularensis subsp. novicida, has low virulence for humans but shares a high degree of antigenic and genetic similarities to F. tularensis types A and B (Forsman et al., 1994), and maintains high virulence in mice (Lauriano et al., 2004; Pammit et al., 2004), thus making subsp. novicida infections of mice an attractive model for tularemia vaccine development.

F. tularensis subsp. tularensis is classified as one of the most infectious pathogenic bacteria because inhalation with only a few organisms will cause disease and significant mortality (Saslaw et al., 1961). F. tularensis also is considered a potential biological weapon and has been developed as a germ warfare agent by several government programs (Christopher et al., 1997; Dennis et al., 2001; Harris, 1992). In this regard, the respiratory tract and lungs are major portals of entry for inhalation exposure and serve as primary sites of infection before systemic spread.

Aerosol exposure to F. tularensis leads to high levels of morbidity and mortality, yet there currently is no tularemia vaccine approved for human usage in the U.S. Because F. tularensis is an intracellular pathogen, a live attenuated strain is a potentially effective means of vaccination. While LVS vaccination has been shown to provide protection against aerosol challenge with F. tularensis subsp. tularensis in mice and humans (Eigelsbach and Downs, 1961; Saslaw et al., 1961; Wu et al., 2005), the basis for attenuation of the LVS strain is unknown, thus bringing its safety for humans into question.

The inventors have discovered attenuated Francisella bacterium vaccines that overcome the deficiencies of previously known vaccines such as the LVS vaccine. The Francisella bacterium can include an alteration in the nucleic acid sequence encoding the mglA, iglA, iglB, iglC, and/or iglD genes of the bacterium. The IglA, iglB, IglC, and IglD genes are duplicated in the F. tularensis subsp. tularensis and F. tularensis subsp. holartica genomes.

As discussed below, the alteration can be, for example, a deletion, substitution, or insertion mutation in the mglA, iglA, iglB, iglC, and/or iglD genes of the bacterium. Additionally, the bacterium can be incorporated into pharmaceutical compositions that can be administered to a subject to induce an immune response. The immune response, in certain aspects, can be a protective or therapeutic immune response.

These and other aspects of the present invention are described in further non-limiting detail in the following sections.

A. iglC, iglD, iglA, iglB, and mglA

The iglC gene encodes a 23 kDa protein that is upregulated during intramacrophage growth in the *Francisella* bacterium. The nucleotide and amino acid sequences of iglC from *Francisella tularensis* subspec. *novicida* are described in SEQ ID NOS: 1 and 2 and can be found at gene bank accession numbers AY293579 and AAP58964 (the contents of which are incorporated by reference), respectively. The nucleotide and amino acid sequences of iglC from *Francisella tularensis* subspec. *tularensis* are described in SEQ ID NOS: 3 and 4 and can be found at gene bank accession numbers NC_006570, NC_006570, YP_170309, and YP_170617 (the contents of which are incorporated by reference), respectively. The nucleotide and amino acid sequences of iglC from *Francisella tularensis* subspec. *holarctica* are described in SEQ ID NOS: 5 and 6, respectively and can be found on the world wide web at theseed.uchigaco.edu/FIG/index.cgi (the contents of which are incorporated by reference). This gene has been shown to be important for intramacrophage survival and growth of subsp. *novicida* (Feldman et al., 2001; Gray et al., 2002). Moreover, iglC mutants of subsp. *novicida* are highly attenuated for virulence in mice and growth within amoebae (Golovliov et al., 2003; Lauriano et al., 2004). IglC is important for the inhibition of phagosome-lysosome fusion (Santic et al., 2005), escape from the phagosome (Lindgren et al., 2004; Santic et al., 2005) and induction of apoptosis in infected macrophages (Lai et al., 2004). IglC also may play a role in the downregulation of TLR-mediated signaling (Telepnev et al., 2003).

Similar to the iglC gene, the iglD gene encodes a protein that is essential for intramacrophage survival, escape from the phagosome, and induction of apoptosis (see Table 1 and 2 below). The nucleotide and amino acid sequences of iglD from *Francisella tularensis* subspec. *novicida* are described in SEQ ID NOS: 7 and 8 and can be found at gene bank accession numbers AY293579 and AAP58965 (the contents of which are incorporated by reference), respectively. The nucleotide and amino acid sequences of iglD from *Francisella tularensis* subspec. *tularensis* are described in SEQ ID NOS: 9 and 10 and can be found at gene bank accession numbers NC_006570, YP_170308, and YP_170616 (the contents of which are incorporated by reference), respectively. The nucleotide and amino acid sequences of iglD from *Francisella tularensis* subspec. *holarctica* are described in SEQ ID NOS: 11 and 12, respectively and can be found on the world wide web at theseed.uchigaco.edu/FIG/index.cgi (the contents of which are incorporated by reference).

The iglA and iglB genes encode proteins that appear to be essential for intramacrophage survival and virulence (see Table 1 and 2 below, and Gray et al., 2002). The nucleotide and amino acid sequences of iglA from *Francisella tularensis* subspec. *novicida* are described in SEQ ID NOS: 13 and 14 and can be found at gene bank accession numbers AY293579 and AAP58962 (the contents of which are incorporated by reference), respectively. The nucleotide and amino acid sequences of iglA from *Francisella tularensis* subspec. *tularensis* are described in SEQ ID NOS: 15 and 16 and can be found at gene bank accession numbers NC_006570, YP_170311, and YP_170619 (the contents of which are incorporated by reference), respectively. The nucleotide and amino acid sequences of iglA from *Francisella tularensis* subspec. *holarctica* are described in SEQ ID NOS: 17 and 18, respectively, and can be found on the world wide web at theseed.uchigaco.edu/FIG/index.cgi (the contents of which are incorporated by reference). The nucleotide and amino acid sequences of iglB from *Francisella tularensis* subspec. *novicida* are described in SEQ ID NOS: 19 and 20 and can be found at gene bank accession numbers AY293579 and AAP58963 (the contents of which are incorporated by reference), respectively. The nucleotide and amino acid sequences of iglB from *Francisella tularensis* subspec. *tularensis* are described in SEQ ID NOS: 21 and 22 and can be found at gene bank accession numbers NC_006570, YP_170310, and YP_170618 (the contents of which are incorporated by reference), respectively. The nucleotide and amino acid sequences of iglB from *Francisella tularensis* subspec. *holarctica* are described in SEQ ID NOS: 23 and 24 and can be found on the world wide web at theseed.uchigaco.edu/FIG/index.cgi (the contents of which are incorporated by reference).

The mglA gene shares homology with SspA of *Escherichia coli*, which regulates stationary-phase gene transcription by interacting with RNA polymerase. mglA also plays a role in stimulating transcription of iglA, iglC and iglD. The nucleotide and amino acid sequences of mglA from *Francisella tularensis* subspec. *novicida* are described in SEQ ID NOS: 25 and 26 and can be found at gene bank accession numbers AF045772 and AAC29032 (the contents of which are incorporated by reference), respectively. The nucleotide and amino acid sequences of mglA from *Francisella tularensis* subspec. *tularensis* are described in SEQ ID NOS: 27 and 28 and can be found at gene bank accession numbers NC_006570 and YP_170231 (the contents of which are incorporated by reference), respectively. The nucleotide and amino acid sequences of mglA from *Francisella tularensis* subspec. *holarctica* are described in SEQ ID NOS: 29 and 30, respectively.

The complete nucleic acid sequence for the *F. tularensis* subsp. *novicida* pathogenicity island can be found at gene bank accession number AY293579, which is incorporated by reference. The complete nucleic acid sequence for the *F. tularensis* subsp. *tularensis* genome can be found at gene bank accession number NC_006570, which is incorporated by reference. The complete nucleic acid sequence for the *F. tularensis* subsp. *holarctica* genome can be found on the world wide web at theseed.uchigaco.edu/FIG/index.cgi (the contents of which are incorporated by reference).

B. Preparation of Attenuated Strains of *Francisella* Bacteria

In order for a modified *Francisella* strain to be effective in a vaccine formulation, the attenuation must be significant enough to prevent the pathogen from evoking severe clinical symptoms, but also insignificant enough to allow limited replication and growth of the bacteria in the recipient. The recipient is a subject needing protection or treatment from a disease caused by a virulent form of *Francisella* or other pathogenic microorganisms.

Attenuated *Francisella* bacteria can be made in several ways. For instance, methods such as subjecting wild-type *Francisella* bacteria having the mglA, iglA, iglB, iglC, and/or iglD genes to mutagenesis techniques known to those of skill in the art (Baron and Nano, 1998; Gray et al., 2002; Lauriano et al., 2003). Where employed, mutagenesis will be accomplished by a variety of standard, mutagenic procedures. Mutation is the process whereby changes occur in the quantity or structure of an organism. Mutation can involve modification of the nucleotide sequence of a single gene, blocks of genes or whole chromosomes. Changes in single genes may be the consequence of point mutations which involve the removal, addition, or substitution of a single nucleotide base within a DNA sequence (Cooley et al. 1988), or they may be the consequence of changes involving the insertion or deletion of large numbers of nucleotides. The mutation may act through affecting transcription or translation of the gene or its mRNA, or the mutation may affect the polypeptide gene product itself in such a way as to render it inactive.

In certain embodiments, attenuation of a *Francisella* Bacteria is carried out by deletion of a portion of the coding region of the mglA, iglA, iglB, iglC, and/or iglD genes. A deletion mutation can reduce the risk that the mutant will revert to a virulent state. For example, some, most (e.g., half or more), or virtually all of the coding region may be deleted (e.g., about 1, 2, 3, 4, 5, 6, 7, 8, 9, 10, 11, 12, 13, 14, 15, 16, 17, 18, 19, 20, 25, 30, 35, 40, 45, 50, 55, 60, 70, 80, 90, to about 100% of the gene). Alternatively, the mutation may be an insertion or deletion of even a single nucleotide that causes a frame shift in the open reading frame, which in turn may cause premature termination of the encoded polypeptide or expression of a completely inactive polypeptide. Mutations can also be generated through insertion of foreign gene sequences, e.g., the insertion of a gene encoding antibiotic resistance.

Deletion mutants can be constructed using any of a number of techniques that are known to those of skill in the art. In one non-limiting example, a strategy using counter selectable markers can be employed which has commonly been utilized to delete genes in many bacteria (Reyrat et al., 1998). In this technique, a double selection strategy is often employed wherein a plasmid is constructed encoding both a selectable and counter selectable marker, with flanking DNA sequences derived from both sides of the desired deletion. The selectable marker is used to select for bacteria in which the plasmid has integrated into the genome in the appropriate location and manner. The counter selecteable marker is used to select for the very small percentage of bacteria that have spontaneously eliminated the integrated plasmid. A fraction of these bacteria will then contain only the desired deletion with no other foreign DNA present.

In another technique, the cre/lox system is used for site specific recombination of DNA. Alternatively, site specific recombination can be achieved using the FLP recombinase techniques (Datsenko and Wanner, 2000). The system consists of 34 base pair lox sequences that are recognized by the bacterial cre recombinase gene. If the lox sites are present in the DNA in an appropriate orientation, DNA flanked by the lox sites will be excised by the cre recombinase, resulting in the deletion of all sequences except for one remaining copy of the lox sequence. Using standard recombination techniques, it is possible to delete the targeted gene of interest in the *Francisella* genome and to replace it with a selectable marker (e.g., a gene coding for kanamycin resistance) that is flanked by the lox sites. Transient expression (by electroporation of a suicide plasmid containing the cre gene under control of a promoter that functions in *Francisella* of the cre recombinase should result in efficient elimination of the lox flanked marker. This process would result in a mutant containing the desired deletion mutation and one copy of the lox sequences.

Another approach includes directly replacing a desired deleted sequence in the *Francisella* genome with a marker gene, such as green fluorescent protein (GFP), β-galactosidase, or luciferase. In this technique, DNA segments flanking a desired deletion are prepared by PCR and cloned into a suicide (non-replicating) vector for *Francisella*. An expression cassette, containing a promoter active in *Francisella* and the appropriate marker gene, is cloned between the flanking sequences. The plasmid is introduced into wild-type *Francisella*. Bacteria that incorporate and express the marker gene (probably at a very low frequency) are isolated and examined for the appropriate recombination event (i.e., replacement of the wild type gene with the marker gene).

Mutations can also be induced following exposure to chemical or physical mutagens. Such mutation-inducing agents include ionizing radiations, ultraviolet light, and a diverse array of chemical such as alkylating agents and polycyclic aromatic hydrocarbons all of which are capable of interacting either directly or indirectly (generally following some metabolic biotransformations) with nucleic acids. For instance, benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the O4 position of thymine induced by exposure to n-nitrosoureas results in TA to CG transitions. The DNA lesions induced by such environmental agents may lead to modifications of base sequence when the affected DNA is replicated or repaired and thus to a mutation.

Random mutations in the mglA, iglA, iglB, iglC, and/or iglD genes of a *Francisella* Bacterium can also be introduced using error prone PCR (Cadwell and Joyce, 1992). The rate of mutagenesis may be increased by performing PCR in multiple tubes with dilutions of templates. Alternatively, random mutations can be introduced by fragmentation and reassembly techniques (See U.S. Pat. No. 5,380,721). The method comprises obtaining polynucleotide library members, pooling and fragmenting the polynucleotides, and reforming fragments therefrom, performing PCR amplification, thereby homologously recombining the fragments to form a shuffled pool of recombined polynucleotides.

Site-directed mutagenesis can also be used to introduce mutations in the mglA, iglA, iglB, iglC, and/or iglD genes of a *Francisella* Bacterium (See, e.g., U.S. Pat. Nos. 5,220,007; 5,284,760; 5,354,670; 5,366,878; 5,389,514; 5,635,377; and 5,789,166). The technique provides for the preparation and testing of sequence variants by introducing one or more nucleotide sequence changes into a selected DNA.

Another aspect of the invention involves the construction of attenuated *Francisella* bacteria of the present invention that additionally comprise a polynucleotide sequence encoding a heterologous polypeptide. For example, for *Francisella*, a "heterologous" polypeptide would be a non-Francisella polypeptide not normally expressed by *Francisella* bacteria. Such attenuated bacteria can be used in methods for delivering the heterologous polypeptide or DNA. For example, *Francisella* could be engineered to lyse upon entry into the cytoplasm of a eukaryotic host cell without causing significant damage, thereby becoming a vector for the introduction of plasmid DNA into the cell. Suitable heterologous polypeptides include immunogenic antigens from other infectious agents (including gram-negative bacteria, gram-positive bacteria and viruses) that induce a protective immune response in the recipients, and expression of the polypeptide antigen by the mutant bacteria in the vaccine causes the recipient to be immunized against the antigen. Other heterologous polypeptides that can be introduced using the *Francisella* include immunomodulatory molecules e.g., cytokines or "performance" proteins such as growth hormone, GRH, and GDF-8.

C. Vaccine Preparations and Routes of Administration

1. Vaccine Preparation

Once produced, synthesized, and/or purified, the attenuated *Francisella* Bacterium can be prepared as a vaccine for administration to a subject. The preparation of a vaccine is generally well understood in the art, as exemplified by U.S. Pat. Nos. 4,608,251, 4,601,903, 4,599,231, 4,599,230, and 4,596,792. Such methods may be used to prepare a vaccine comprising an immunogenic composition comprising at least one *Francisella* Bacterium as active ingredient(s), in light of the present disclosure. In certain embodiments, the compositions of the present invention are prepared to be pharmacologically acceptable vaccines.

Pharmaceutical vaccine compositions of the present invention comprise an effective amount of one or more *Francisella* Bacterium or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one *Francisella* Bacterium or additional active ingredient will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, e.g., Remington's 1990). The vaccines of the present invention may comprise different types of carriers depending on whether it is to be administered in solid, liquid or aerosol form, and whether it needs to be sterile for such routes of administration as injection. Except insofar as any conventional carrier is incompatible with the active ingredient, its use in the therapeutic or pharmaceutical compositions is contemplated.

The actual dosage amount of a vaccine composition of the present invention can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose (s) for the individual subject.

In certain non-limiting embodiments, pharmaceutical compositions may comprise, for example, at least about 0.1% of an active ingredient. In other embodiments, the active ingredient may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A person of ordinary skill will recognize that the vaccine compositions of the present invention can include at least about 0.0001% to about 0.001%, 0.001% to about 0.01%, 0.01% to about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of an attenuated *Francisella* Bacterium or other ingredients (e.g., additional vaccine components, pharmaceutical excipients, etc.) In non-limiting aspects, the percentage can be calculated by weight or volume of the total composition.

The vaccine component(s) may be formulated into a composition in a free base, neutral or salt form. Pharmaceutically acceptable salts, include the acid addition salts, e.g., those formed with the free amino groups of a proteinaceous composition, or which are formed with inorganic acids such as, for example, hydrochloric or phosphoric acids, or such organic acids as acetic, oxalic, tartaric or mandelic acid. Salts formed with the free carboxyl groups can also be derived from inorganic bases such as, for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example, liquid polyol or lipids; by the use of surfactants such as, for example, hydroxypropylcellulose; or combinations thereof. In many cases, one can include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained.

In certain embodiments the vaccine component(s) are prepared for administration by such routes as oral ingestion. In these embodiments, the composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Carriers for oral administration comprise inert diluents, assimilable edible carriers or combinations thereof. In other aspects of the invention, the oral composition may be prepared as a syrup or elixir, and may comprise, for example, at least one active agent, a sweetening agent, a preservative, a flavoring agent, a dye, a preservative, or combinations thereof.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation are vacuum-drying or freeze-drying techniques which yield a powder of the active ingredient plus any additional desired ingredient from a previously filter-sterilized liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

2. Routes of Administration

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrauterinely, intrarectally, intrathecally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990).

D. Monitoring Immunogenic Response and Protective Immunity

An "immunologically protective amount" of the attenuated mutant bacteria is an amount effective to induce an immunogenic response in the recipient that is adequate to prevent or ameliorate signs or symptoms of disease, including adverse health effects or complications thereof, caused by infection with wild type *Francisella* bacteria. Either humoral immunity or cell-mediated immunity or both may be induced. The immunogenic response of an animal to a vaccine composition may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number and % of days of diarrhea, milk production or yield, average daily weight gain, physical condition and overall health and performance of the subject.

E. Additional Vaccine Components

It is contemplated that a vaccine or immunogenic composition of the present invention can be combined with one or more additional components (e.g., components other than the attenuated *Francisella* bacteria of the present invention) to form a more effective vaccine. Non-limiting examples of additional components include, for example, one or more additional immunogens, immunomodulators, or adjuvants to stimulate an immune response to an immunogenic composition of the present invention and/or the additional component(s).

1. Immunomodulators

It is contemplated that immunomodulators can be included in the vaccine to augment a cell's or a subject's response. Immunomodulators can be included as purified proteins, nucleic acids encoding immunomodulators, and/or cells that express immunomodulators in the vaccine composition. The following sections list non-limiting examples of immunomodulators that are of interest, and it is contemplated that various combinations of immunomodulators may be used in certain embodiments.

i. Cytokines

Interleukins, cytokines, nucleic acids encoding interleukins or cytokines, and/or cells expressing such compounds are contemplated as possible vaccine components. Interleukins and cytokines, include but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, -interferon, -interferon, γ-interferon, angiostatin, thrombospondin, endostatin, GM-CSF, G-CSF, M-CSF, METH-1, METH-2, tumor necrosis factor, TGF, LT and combinations thereof.

ii. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

iii. Immunogenic Carrier Proteins

In certain embodiments, a vaccine or immunogenic composition may be chemically coupled to a carrier or recombinantly expressed with a immunogenic carrier peptide or polypeptide (e.g., an antigen-carrier fusion peptide or polypeptide) to enhance an immune reaction. Exemplary immunogenic carrier amino acid sequences include hepatitis B surface antigen, keyhole limpet hemocyanin (KLH) and bovine serum albumin (BSA). Other albumins such as ovalbumin, mouse serum albumin or rabbit serum albumin also can be used as immunogenic carrier proteins. Means for conjugating a polypeptide or peptide to a immunogenic carrier protein are well known in the art and include, for example, glutaraldehyde, m-maleimidobenzoyl-N-hydroxysuccinimide ester, carbodiimide and bis-biazotized benzidine.

iv. Biological Response Modifiers

It may be desirable to co-administer biologic response modifiers (BRM), which have been shown to upregulate T cell immunity or downregulate suppressor cell activity. Such BRMs include, but are not limited to, cimetidine (CIM; 1200 mg/d) (Smith/Kline, Pa.); low-dose cyclophosphamide (CYP; 300 mg/m$^2$) (Johnson/Mead, N.J.), or a gene encoding a protein involved in one or more immune helper functions, such as B-7.

2. Adjuvants

Immunization protocols have used adjuvants to stimulate responses for many years, and as such adjuvants are well known to one of ordinary skill in the art. Some adjuvants affect the way in which immunogens are presented. For example, the immune response is increased when protein immunogens are precipitated by alum. Emulsification of immunogens also prolongs the duration of immunogen presentation.

In one aspect, an adjuvant effect is achieved by use of an agent, such as alum, used in about 0.05 to about 0.1% solution in phosphate buffered saline. Alternatively, the immunogen is made as an admixture with synthetic polymers of sugars (Carbopol®) used as an about 0.25% solution. Adjuvant effect may also be made by aggregation of the immunogen in the vaccine by heat treatment with temperatures ranging between about 70° to about 101° C. for a 30-second to 2-minute period. Aggregation by reactivating with pepsin-treated (Fab) antibodies to albumin, mixture with bacterial cell(s) such as C. parvum or an endotoxin or lipopolysaccharide components of Gram-negative bacteria, emulsion in physiologically acceptable oil vehicles, such as mannide mono-oleate (Aracel A) or emulsion with a 20% solution of a perfluorocarbon (Fluosol-DA®) used as a block substitute, also may be employed.

Some adjuvants, for example, certain organic molecules obtained from bacteria, act on the host rather than on the immunogen. An example is muramyl dipeptide (N-acetylmuramyl-L-alanyl-D-isoglutamine [MDP]), a bacterial peptidoglycan. Derivatives of muramyl dipeptide, such as the amino acid derivative threonyl-MDP, and the fatty acid derivative MTPPE, are also contemplated. The effects of MDP, as with most adjuvants, are not fully understood. MDP stimulates macrophages but also appears to stimulate B cells directly. The effects of adjuvants, therefore, are not immunogen-specific. If they are administered together with a purified immunogen, however, they can be used to selectively promote the response to the immunogen.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is thought to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

Adjuvants have been used experimentally to promote a generalized increase in immunity against unknown immunogens (e.g., U.S. Pat. No. 4,877,611). In certain embodiments, hemocyanins and hemoerythrins may also be used in the invention. The use of hemocyanin from keyhole limpet (KLH) is used in certain embodiments, although other molluscan and arthropod hemocyanins and hemoerythrins can be employed.

Various polysaccharide adjuvants may also be used. For example, the effect of various pneumococcal polysaccharide adjuvants on the antibody response of mice has been described (Yin et al., 1989). The doses that produce optimal responses, or that otherwise do not produce suppression, should be employed as indicated (Yin et al., 1989). Polyamine varieties of polysaccharides can be used, such as chitin and chitosan, including deacetylated chitin.

Another adjuvant contemplated for use in the present invention is BCG. BCG (bacillus Calmette-Guerin, an attenuated strain of Mycobacterium) and BCG-cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945. BCG is an important clinical tool because of its immunostimulatory properties. BCG acts to stimulate the reticuloendothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990).

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994; Hunter et al., 1991) may also be employed. Oligonucleotides are another useful group of adjuvants (Yamamoto et al., 1988). Quil A and lentinen are other adjuvants that may be used in certain embodiments of the present invention.

One group of adjuvants for use in the invention are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

In other embodiments, the present invention contemplates that a variety of adjuvants may be employed in the membranes of cells, resulting in an improved immunogenic composition. The only requirement is, generally, that the adjuvant be capable of incorporation into, physical association with, or conjugation to, the cell membrane of the cell in question. Those of skill in the art will know the different kinds of adjuvants that can be conjugated to cellular vaccines in accordance with this invention and these include alkyl lysophospholipids (ALP); BCG; and biotin (including biotinylated derivatives) among others. Certain adjuvants particularly contemplated for use are the teichoic acids from Gram negative cells. These include the lipoteichoic acids (LTA), ribitol teichoic acids (RTA) and glycerol teichoic acid (GTA). Active forms of their synthetic counterparts may also be employed in connection with the invention (Takada et al., 1995a).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

One group of adjuvants for use in some embodiments of the present invention are those that can be encoded by a nucleic acid (e.g., DNA or RNA). It is contemplated that such adjuvants may be encoded in a nucleic acid (e.g., an expression vector) encoding the immunogen, or in a separate vector or other construct. These nucleic acids encoding the adjuvants can be delivered directly, such as for example with lipids or liposomes.

F. Vaccine Component Purification

A vaccine component may be isolated and/or purified from the chemical synthesis reagents, cell or cellular components. Purification can be accomplished by any appropriate technique that is described in the specification or known to those of skill in the art (e.g., Sambrook et al., 1987). There is no general requirement that a vaccine or immunogenic composition of the present invention or other vaccine component always be provided in their most purified state. Indeed, it is contemplated that a less substantially purified vaccine component, which is nonetheless enriched in the desired compound, relative to the natural state, will have utility in certain embodiments.

The present invention also provides purified and substantially purified vaccines or vaccine components. The term "purified vaccine component" as used herein, is intended to refer to at least one vaccine component wherein the component is purified to any degree relative to its naturally-obtainable state, e.g., relative to its purity within a cellular extract or reagents of chemical synthesis.

Where the term "substantially purified" is used, this will refer to a composition in which the specific compound forms the major component of the composition, such as constituting about 50% of the compounds in the composition or more. In certain aspects, a substantially purified vaccine component will constitute more than about 60%, about 70%, about 80%, about 90%, about 95%, about 99% or even more of the compounds in the composition.

Various techniques suitable for use in chemical, biomolecule or biological purification, well known to those of skill in the art, may be applicable to preparation of a vaccine component of the present invention. These include, for example, precipitation with ammonium sulfate, PEG, antibodies and the like or by heat denaturation, followed by centrifugation; fractionation, chromatographic procedures, including but not limited to, partition chromatograph (e.g., paper chromatograph, thin-layer chromatograph (TLC), gas-liquid chromatography and gel chromatography) gas chromatography, high performance liquid chromatography, affinity chromatography, supercritical flow chromatography, ion exchange chromatography, gel filtration chromatography, reverse phase chromatography, hydroxylapatite chromatography, lectin affinity chromatography; isoelectric focusing and gel electrophoresis (see for example, Sambrook et al. 1989; and Freifelder, Physical Biochemistry, Second Edition, pages 238-246).

G. Antibody Generation

In certain embodiments, isolated antibodies to the vaccine or immunogenic compositions of the present invention are contemplated as useful for purification, diagnostic and therapeutic applications. Monoclonal antibodies (MAbs) are recognized to have certain advantages, e.g., reproducibility and large-scale production, and their use is generally used. MAbs may be readily prepared through use of well-known techniques, such as those exemplified in U.S. Pat. No. 4,196,265.

In certain diagnostic or vaccine component purification aspects, an antibody specific to one or more vaccine components may be used. Non-limiting examples of such immunodetection methods include enzyme linked immunosorbent assay (ELISA), radioimmunoassay (RIA), immunoradiometric assay, fluoroimmunoassay, chemiluminescent assay, bioluminescent assay, and Western blot, to mention a few. The steps of various useful immunodetection methods have been described in the scientific literature, such as, e.g., Doolittle and Ben-Zeev, 1999; Gulbis and Galand, 1993; De Jager et al., 1993; and Nakamura et al., 1987. Often, the antibody may be conjugated with an imaging agent to enhance detection of a vaccine component ligand bound to the antibody, as would be known to one of ordinary skill in the art. Many appropriate imaging agents are known in the art, as are methods for their attachment to antibodies (see, for e.g., U.S. Pat. Nos. 5,021,236; 4,938,948; and 4,472,509).

In general, the detection of immunocomplex formation is well known in the art and may be achieved through the application of numerous approaches. These methods are generally based upon the detection of a label or marker, such as radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241. Of course, one may find additional advantages through the use of a secondary binding ligand such as a second antibody and/or a biotin/avidin ligand binding arrangement, as is known in the art.

H. Combination Therapy

In order to increase the effectiveness of the immunogenic and vaccine compositions of the present invention ("present compositions"), it may be desirable to combine the present compositions with other agents or vaccine components and methods effective in treating or preventing *Francisella* infection. The additional agents or vaccine components that can be used in the context of the present invention include such agents or vaccine components known to those of skill in the art (including those disclosed in other sections of the present specification).

This process can involve administering the combination of the present compositions with another agent(s) or vaccine component to the subject at the same time, for example, using a single composition or pharmacological formulation that includes both agents, or using two distinct compositions or formulations given at the same time, wherein one composition includes the compositions of the present invention which is administered before, during, or after the additional agent or vaccine component. The exact schedule of treatment with the present compositions and the second agent or vaccine component is determined in large part by the pharmacokinetic or pharmacodynamic properties of compositions being administered.

In embodiments where the present compositions and the additional agents or vaccine components are administered separately to the subject, one may wish that a significant period of time did not expire between the time of each delivery, such that the second agent or vaccine component and the present compositions would be able to exert an advantageously combined effect on the subject. In such instances, it is contemplated that one may administer to the subject with both modalities within about 12-24 h of each other or within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, such as where the present compositions is "A" and the second agent or vaccine component is "B":

| | | | | | | |
|---|---|---|---|---|---|---|
| A/B/A | B/A/B | B/B/A | A/A/B | A/B/B | B/A/A | A/B/B/B |
| B/A/B/B | | | | | | |
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | |

I. Kits

In still further embodiments, the present invention concerns kits for use with the vaccination methods described above. Immunogenic compositions comprising attenuated *Francisella* bacteria may be provided in a kit. Such kits may be used to provide immunogens, vaccine components or vaccine preparations for vaccination in a ready to use and storable container.

The container of the kits can generally include at least one vial, test tube, flask, bottle, syringe and/or other container, into which at least one immunogenic composition, antibody, vaccine component or vaccine may be placed and/or suitably aliquoted. The kits of the present invention may include a means for containing vaccine components, vaccines or any other reagent containers in close confinement for commercial sale. Such containers may include injection and/or blow-molded plastic containers into which the desired vials are retained.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Experimental Set-Up and Procedures

Bacteria. *F. tularensis* subsp. *novicida* U112 was provided by Dr. Francis Nano (University of Victoria, Canada). Construction of the isogenic strain KKF24 (*F. tularensis* subsp. *novicida* ΔiglC::ermC (ΔiglC::ermC, see SEQ ID NO:31)) has been described (Lauriano et al., 2003). Strains were grown at 37° C. in Typticase Soy broth (TSB) supplemented with 0.1% cysteine.

Mice. Six to eight-week old female BALB/c mice were obtained from the National Cancer Institute (Bethesda, Md.). BALB/c IFN-$\gamma^{-/-}$ mice and C57BL/6 μMT (B cell deficient) mice and wild-type animals were obtained from the Jackson Laboratories (Bar Harbor, Me.). All animal care and experimental procedures were performed in compliance with the Institutional Animal Care and Use Committee (IACUC) guidelines.

Intranasal immunization and pulmonary challenge. Mice were first anesthetized with 3% Isofluorane using a rodent anesthesia system (Harvard Apparatus, Holliston, Mass.) (Murthy et al., 2004; Pammit et al., 2004), then inoculated intranasally with $10^6$ CFU of KKF24 in 25 μl of PBS. Mock-vaccinated animals were treated with PBS alone. All animals were then challenged 4 weeks later, i.n. as described above, with escalating CFU (100 $LD_{50}$-10,000 $LD_{50}$) of U112 [the $LD_{50}$ of U112 administered i.n. has been calculated as 10 CFU (Lauriano et al., 2004)]. The actual CFU administered in each experiment was determined by serial dilution of inocula and plating on TSA supplemented with 0.1% cysteine. Animals were monitored daily for morbidity and mortality. Sera were prepared by collection of blood from the orbital plexus.

Spleen and lymph node cell culture for cytokine profiles. Spleens and cervical lymph nodes were collected from mice 10 days following i.n. vaccination with $10^6$ CFU of KKF24 or PBS (mock-vaccinated animals). Single cell suspensions were prepared ($1\times10^6$ cells/well for spleen cells and $2\times10^5$ cells/well for lymph node cells) and cultured in DMEM supplemented with 10% (v/v) FCS (Mediatech, Fairfax, Va.) $\pm 10^5$ CFU of UV-inactivated KKF24 for 72 h. Cells also were cultured with the unrelated antigen hen egg lysozyme (HEL). Culture supernatants were harvested for IFN-γ, IL-12 and IL-4 analysis by ELISA as described previously (Pammit et al., 2004). Lymph nodes and spleens from vaccinated mice were simultaneously evaluated for viable bacteria. No viable bacteria were recovered at 10 days post inoculation from the examined tissues.

Detection of antibody and isotype levels by ELISA. Microtiter plates were coated overnight with $10^6$ CFU of UV-inactivated KKF24 in sodium bicarbonate buffer (pH 9.5), washed with PBS containing 0.3% Brij-35 (Sigma) and blocked for 1 h at room temperature with PBS containing 2% bovine serum albumin (BSA, EM Science Gibbstown, N.J.). Serial dilutions of serum were added to wells and incubated at room temperature for 2 h. The plates were then washed and incubated for an additional 1 h with goat anti-mouse total Ig, IgG1 and IgG2a conjugated to alkaline phosphatase (Southern Biotechnology Associates, Birmingham, Ala.). After incubation for 1 h, the plates were washed and p-nitrophenyl phosphate substrate was added for color development. Absorbance at 405 nm was measured using an ELISA microplate reader (Biotek Instruments, Winooski, Vt.). The reciprocal serum dilutions corresponding to 50% maximal binding were used to obtain titers. No binding of immune sera was observed when the plates were coated with the unrelated antigen HEL.

Opsonophagocytosis assays. To examine the opsonic potential of the immune sera, an opsonophagocytosis assay was established using chamber slides (Lab-Tek, Nunc, Naperville, Ill.) that were seeded overnight with $1\times10^5$ J774A.1 cells (macrophage cell line; American Type Culture Collection, Manassas, Va.) overnight. Wild-type *F. tularensis* subsp. *novicida* U112 ($10^5$ CFU) was incubated with varying concentrations of heat inactivated immune (collected 30 days after i.n. vaccination) or normal mouse serum in Eppendorf tubes for 30 min at 37° C. with end-over-end rotation. The opsonized bacteria were then incubated for an additional 1 h at 37° C. with the J774A.1 macrophages in the chamber slides. Following incubation, the solutions containing the bacteria were removed, and macrophages were incubated with DMEM plus 10 μg/ml of gentamicin to eliminate extracellular bacteria. The macrophages then were washed 3-times with PBS and fixed with 2% paraformaldehyde solution overnight at 4° C. The macrophages were subsequently washed, treated with 1% saponin (Sigma) for 30 min at room temperature, incubated with 3% BSA (EM Science), and subsequently stained for 1 h at 37 C with R-PE conjugated rat anti-mouse CD11b (BD Bioscience), *F. novicida* LPS monoclonal ab #8.2 conjugated to Alexa 488, and Bisbenzimide H 33258 (Sigma) for nuclear staining. Cells were washed and images were acquired using an Axiocam digital camera (Zeiss, Thornwood, N.Y.) connected to a Zeiss Axioskop 2 Plus research microscope. Random fields were imaged and the number of cells containing bacteria were counted. The percentage of macrophages containing fluorescent bacteria was used as a measure of phagocytic activity.

Adoptive transfer studies. Immune serum was prepared by collection from 10 C57BL/6 mice four weeks after i.n. vaccination with $10^6$ CFU of KKF24. Normal mouse serum was prepared from unvaccinated animals. Naïve C57BL/6 βMT (B cell deficient) recipient mice were injected i.p. with 200 μl of a 1:3 dilution of pooled immune or normal serum at −8 h before i.n. challenge with 100 $LD_{50}$ of F. tularensis subsp. novicida. All animals also were injected with similar amounts of either immune or normal mouse serum at 24 h, 48 h and 72 h after bacterial challenge. Animals were monitored daily for morbidity and mortality.

Histology and immunofluorescence staining. Lungs were removed 3 days and 60 days after primary immunization and embedded in optimal cutting temperature (OCT) resin and snap frozen. Serial horizontal cryosections of 5 μm were prepared and placed on silane coated-slides (VWR International, West Chester, Pa.). All slides were dried overnight and fixed in fresh acetone for 20 s at room temperature. Some sections also were fixed with formalin for 10 min and stained by hematoxylin and eosin (H&E). For immunofluorescent staining, slides were blocked with 3% BSA for 5 min, followed by incubation with 10% normal rat serum (Sigma) for 30 min. Tissue sections were subsequently incubated with R-phycoerythrin (R-PE) conjugated rat anti-mouse CD11b (BD Biosciences, San Diego, Calif.) for 40 min. Some sections also were stained with anti-F. tularensis subsp. novicida LPS monoclonal antibody #8.2 (ImmunoPrecise Antibodies Ltd, Victoria, Canada) conjugated to Alexa 488 (BD Biosciences). Sections were then washed and mounted using fluorsave reagent (Calbiochem, La Jolla, Calif.) containing Hoescht stain for nuclear staining. Images were acquired using an Axiocam digital camera (Zeiss, Thornwood, N.Y.) connected to a Zeiss Axioskop 2 Plus research microscope.

Statistical Analysis. Survival data were analyzed by the Mann-Whitney rank sum test and the antibody titers and cytokine analyses were evaluated by Student's t-test using the statistical software program SigmaStat. The data are presented as mean±standard deviation. The number of repetitions of each experiment is indicated in the figure legends. Each experiment was repeated at least twice.

Example 2

Intranasal Vaccination with F. tularensis Subsp. novicida ΔiglC is Highly Efficacious Against Intranasal Challenge with the Wildtype Strain To directly assess the efficacy of F. tularensis subsp. novicida ΔiglC to function as a vaccine, BALB/c mice were vaccinated i.n. with $10^6$ CFU of KKF24. Vaccinated mice exhibited no signs of morbidity at this dosage and were challenged 30 days later i.n. with escalating inocula of the wildtype F. tularensis subsp. novicida U112 strain. As shown in FIG. 1, vaccinated animals challenged with $10^3$ CFU (100 $LD_{50}$) of U112 were highly protected (82% survival) with minimal loss of body weight (data not shown). When the challenge inoculum was increased to $10^4$ CFU (1000 $LD_{50}$) of U112, the survival rate decreased to 50%. Increasing the challenge inoculum further to $10^5$ CFU (10,000 $LD_{50}$) of U112 resulted in 20% survival. There was no survival of any unvaccinated animals at the challenge doses tested, indicating that all three inocula ($10^3$, $10^4$, and $10^5$ CFU) of U112 were lethal doses, as expected.

Figure 2:
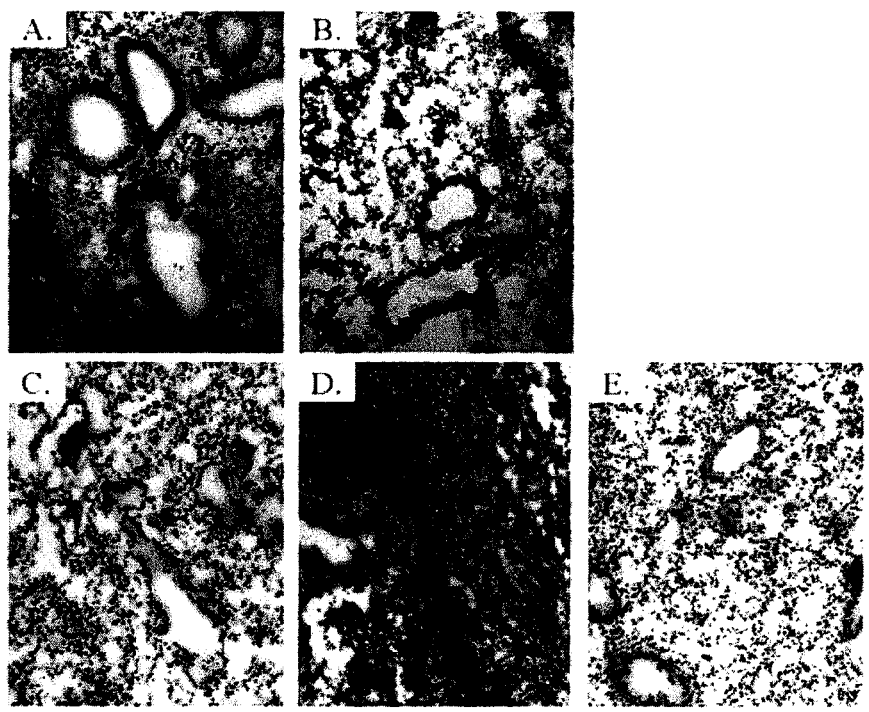
FIG. 2: Intranasal vaccination with KKF24 induces minimal pulmonary histopathological changes. Lungs were harvested from vaccinated animals, prepared for histological study and stained with H&E. (A) KKF24 primed lung day 3; (B) KKF24 primed lung day 60; (C) KKF24 primed and wild type challenged lung day 60; (D) PBS mock-treated and wild type challenged lung day 3; (E) PBS mock-treated animal. Magnification 10×. Results are representative of 2 independent experiments.

Histological analyses were performed on vaccinated and challenged mice, as shown in FIG. 2. Lung sections from mice vaccinated i.n. with $10^6$ CFU KKF24 three days (FIG. 2A) or 60 days (FIG. 2B) post vaccination revealed open air spaces with normal pulmonary architecture and no obvious evidence of histopathological changes, similar to mock (PBS) treated and unchallenged mice (2E). Lung tissue of vaccinated mice that were challenged i.n. with $10^3$ CFU of the wildtype U112 strain 30 days following challenge (FIG. 2C) appeared similar to the lung tissue of vaccinated unchallenged mice (FIG. 2B). In contrast, the lungs of mice mock-vaccinated with PBS and then challenged with $10^3$ CFU of the wildtype U112 strain displayed severe consolidation and polymorphonuclear cell infiltration 3 days after challenge (FIG. 2D).

Figure 3:
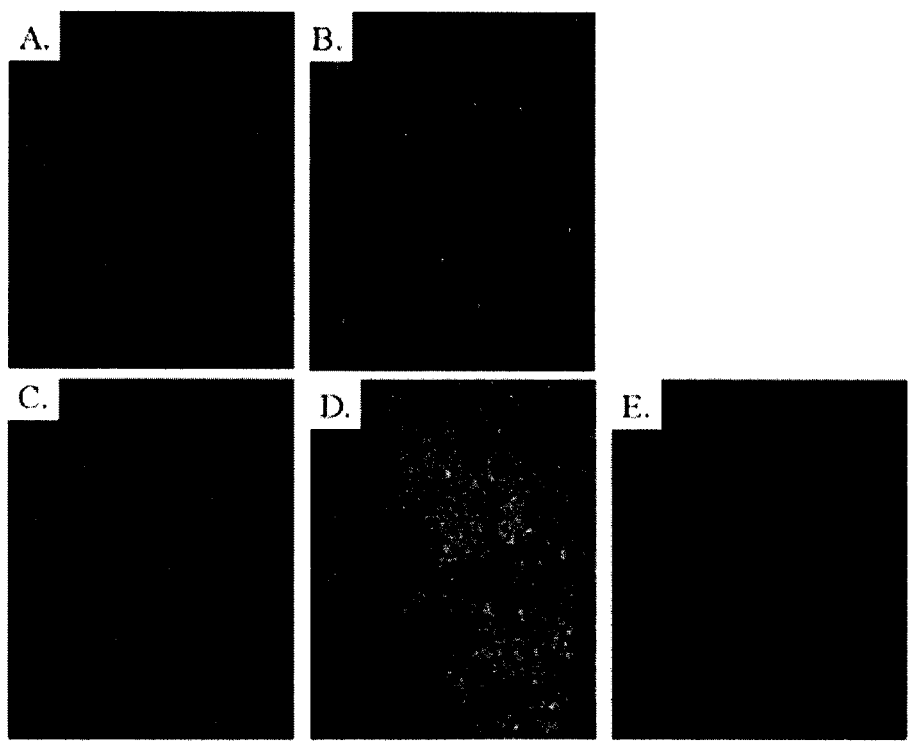
FIG. 3: Immunofluorescence staining of F. tularensis subsp. novicida following pulmonary challenge. Lungs were harvested from vaccinated animals and sections were stained with R-phycoerythrin conjugated rat anti-mouse CD11b (red) and anti F. novicida LPS monoclonal ab #8.2 (green). Nuclear staining (blue) was visualized with Bisbenzimide H 33258. (A) KKF24 primed lung day 3; (B) KKF24 primed lung day 60; (C) KKF24 primed and wild type challenged lung day 60; (D) PBS mock-treated and wild type challenged lung day 3; (E) PBS mock-treated animal. Magnification 20×. Results are representative of 2 independent experiments.

In situ immunohistochemistry (FIG. 3) was performed on lung tissue from vaccinated and challenged mice with anti-CD11b (red; stains macrophages) and anti-F. tularensis subsp. novicida LPS (green; stains bacteria). Mice vaccinated i.n. with $10^6$ CFU KKF24 had very few bacteria within the lung sections three (FIG. 3A) or 60 days (FIG. 3B) after vaccination and showed modest to no influx of macrophages, in comparison to PBS mock-treated and challenged mice (FIG. 3D). Mice vaccinated i.n. with KKF24, and then challenged i.n. with $10^3$ CFU of the wildtype U112 strain had no detectable bacteria within the lungs at 30 days post-challenge (FIG. 3C), whereas, abundant macrophages and bacteria could be detected in the lungs of mock-vaccinated mice challenged i.n. with $10^3$ CFU of the wildtype U112 strain as early as three days post challenge (FIG. 3D). As expected, there were few macrophages and no detectable bacteria in mock (PBS) treated and unchallenged mice (FIG. 3E). In addition, parallel lung tissues were also evaluated for bacterial loads. The mice vaccinated i.n. with KK24 exhibited no viable bacteria within the lungs 3 days post-inoculation, and no recoverable bacteria 60 days after immunization, which illustrates the high degree of attenuation of this strain. These results, utilizing subsp. novicida, show that a F. tularensis ΔiglC strain is a viable candidate for a live attenuated vaccine against pneumonic tularemia.

Example 3

Figure 4:
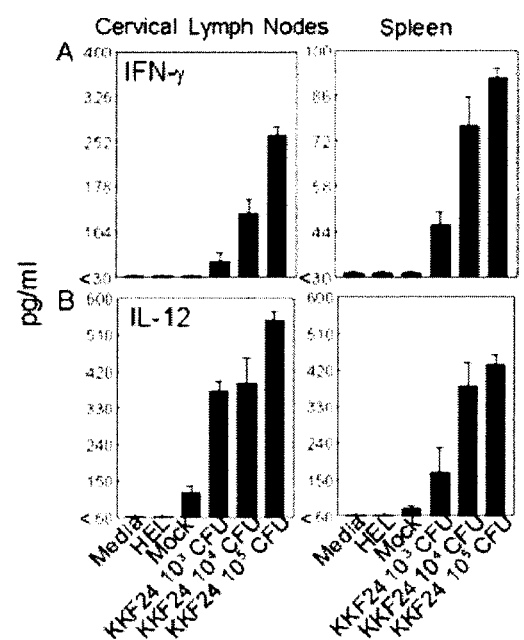
FIG. 4: Cytokine recall responses after vaccination with KKF24. BALB/c mice (3 mice/group) were anesthetized with 3% Isoflurane and vaccinated i.n. with KKF24 ($10^6$ CFU) in 25 µl of sterile PBS. On day 10, spleen and lymph node cells were tested for KKF24-induced IFN (A) and IL-12 (B) secretion by ELISA. Differences in IFN and IL-12 secretion between cells exposed to KKF24 and cells alone were significant at p<0.005. Results are representative of 3 independent experiments.

Vaccination with F. tularensis Subsp. novicida ΔiglC Induces a Th1-Type Immune Response The inventors examined whether vaccination with the KKF24 strain induces antigen-specific cell mediated responses. Mice were vaccinated with KKF24 ($10^6$ CFU), then 10 days later spleen and lymph node cells were tested for F. tularensis subsp. novicida-induced cytokine recall response. As shown in FIG. 4A, the draining cervical lymph node and spleen cells stimulated with UV-inactivated KKF24 induced an appreciable IFN-γ response in a dose-dependent manner in culture. Similarly, there was potent IL-12 secretion (FIG. 4B) from the stimulated cells upon i.n. vaccination with KKF24. There was negligible IL-4 induction in stimulated cultures (data not shown). Cells from mock-vaccinated (PBS) animals had no cytokine responses upon recall with KKF24. In addition, there was no recall response in cells from vaccinated animals to the unrelated control antigen HEL.

Figure 5:
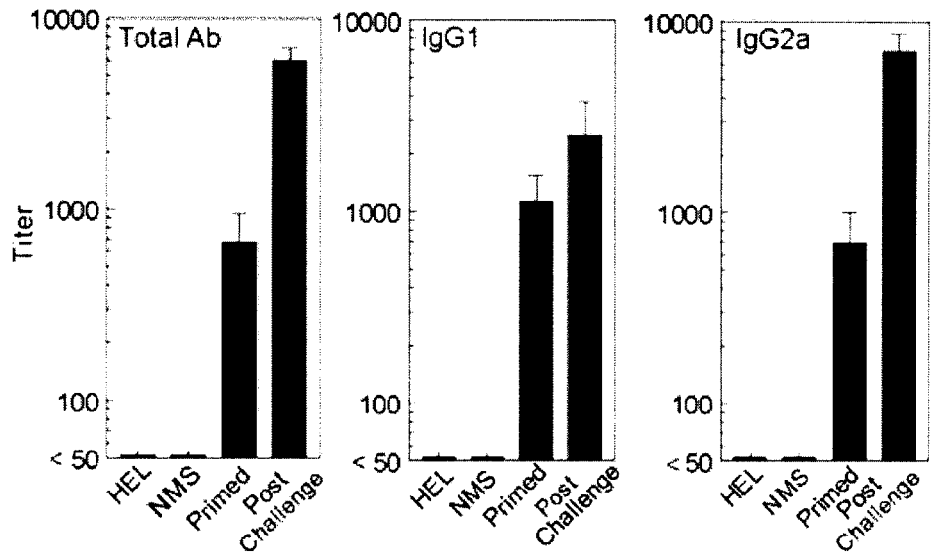
FIG. 5: Serum antibody profiles after vaccination with i.n. with KKF24. BALB/c mice were first anesthetized with 3% Isofluorane and primed i.n. with KKF24 ($10^6$ CFU) in 25 µl of sterile PBS. All animals were bled at day 30 and subsequently challenged with 100 $LD_{50}$ of wild type F. tularensis subsp. novicida U 112. Surviving animals were bled on day 60 sera and were analyzed by isotype-specific ELISA using UV inactivated KKF24-coated microtiter plates. The results are reported as 50% end point titers. Differences in antibody binding between immune serum and normal mouse serum for total ab, IgG1 and IgG2a were significant at p<0.005. Results are representative of 3 independent experiments.

Sera from KKF24-vaccinated mice were analyzed for antibody profiles 30 days after initial vaccination, as well as 30 days following challenge with the wildtype U112 strain. Intranasal immunization with $10^6$ CFU KKF24 induced a robust primary antibody response that included the induction of subsp. novicida-specific total, IgG1 and IgG2a antibodies (FIG. 5). Following i.n. challenge of vaccinated animals with $10^3$ CFU of the wildtype strain, surviving animals displayed higher subsp. *novicida*-specific IgG2a antibody titers, than IgG1 titers. No binding of immune sera was observed with the unrelated antigen HEL. The antibodies induced were specific, and the antigenic determinants of *F. tularensis* subsp. *novicida* that stimulated the reactivity of the antibodies are currently under investigation. Collectively, the results demonstrate that i.n. vaccination with KKF24 induces a robust Th1-type cytokine and antibody response.

Example 4

IFN-γ and *F. tularensis* Subsp. *novicida* ΔiglC-Mediated Protection

Figure 6:
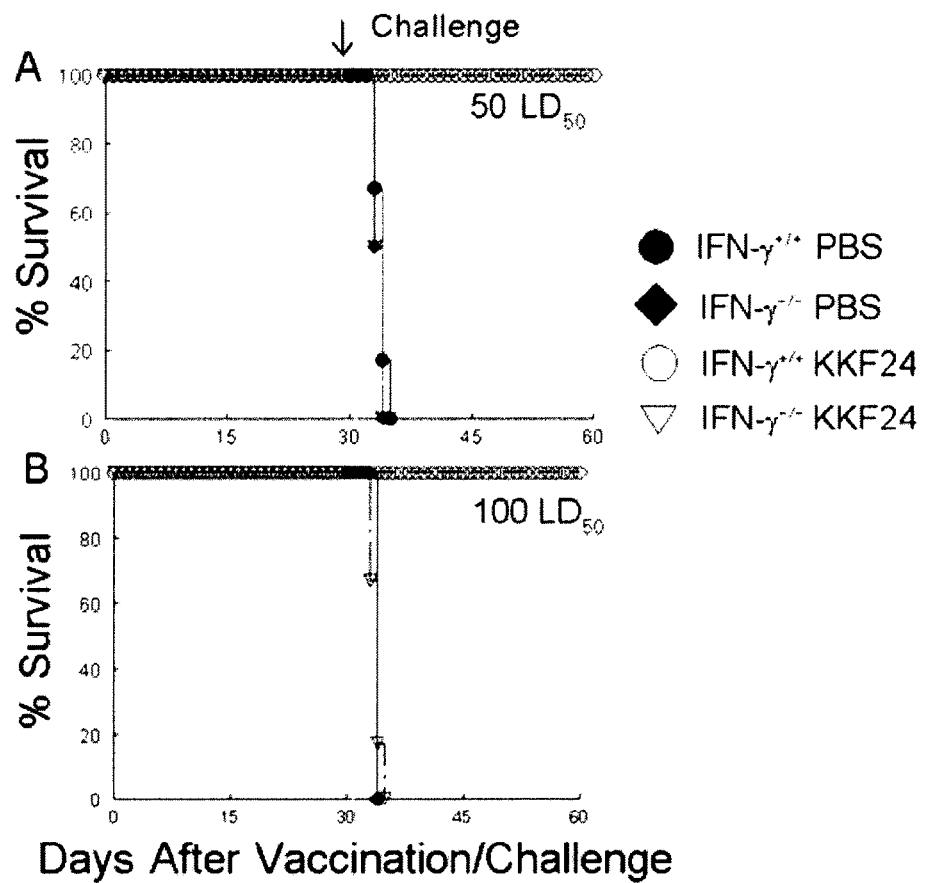
FIG. 6: IFN-dependent KKF24-mediated protection. BALB/c $IFN^{-/-}$ mice and $IFN^{+/+}$ mice (6 mice/group) were anesthetized with 3% Isofluorane and vaccinated i.n. with KKF24 ($10^6$ CFU) in 25 µl of sterile PBS. Animals were challenged after 30 days with 50 $LD_{50}$ (A) and 100 $LD_{50}$ (B) of wild type F. tularensis subsp. novicida U112 respectively. All animals were monitored daily for survival. Differences in survival between vaccinated $IFN^{+/+}$ mice and $IFN^{-/-}$ mice were significant at p<0.001. Results are representative of 2 independent experiments.

To determine the contribution of IFN-γ in protection mediated by the ΔiglC strain, BALB/c IFN-γ$^{-/-}$ and IFN-γ$^{+/+}$ mice were immunized i.n. with $10^6$ CFU of the *F. tularensis* subsp. *novicida* KKF24 strain. Notably, the vaccinated IFN-γ$^{-/-}$ mice all survived the infection with KKF24, with no overt symptoms of disease, indicating the highly attenuated nature of the ΔiglC strain. Vaccinated mice were challenged i.n. 30 days later with either 50 LD$_{50}$ (500 CFU, FIG. 6A) or 100 LD$_{50}$ (1000 CFU, FIG. 6B) of the wild-type *F. tularensis* subsp. *novicida* strain U112. It was found that all of the IFN-γ$^{-/-}$ vaccinated mice quickly succumbed within 4-5 days to the pulmonary challenge with the wild-type strain, whereas 100% of the IFN-γ$^{+/+}$ mice were completely protected against both challenge doses. Mock-vaccinated (PBS) IFN-γ$^{+/+}$ and IFN-γ$^{-/-}$ were highly susceptible to the lethal challenges. These results indicate that IFN-γ-dependent mechanisms play a pivotal role during vaccination with KKF24 in shaping the protective immune response against i.n. challenge with the wildtype strain.

Example 5

Figure 7:
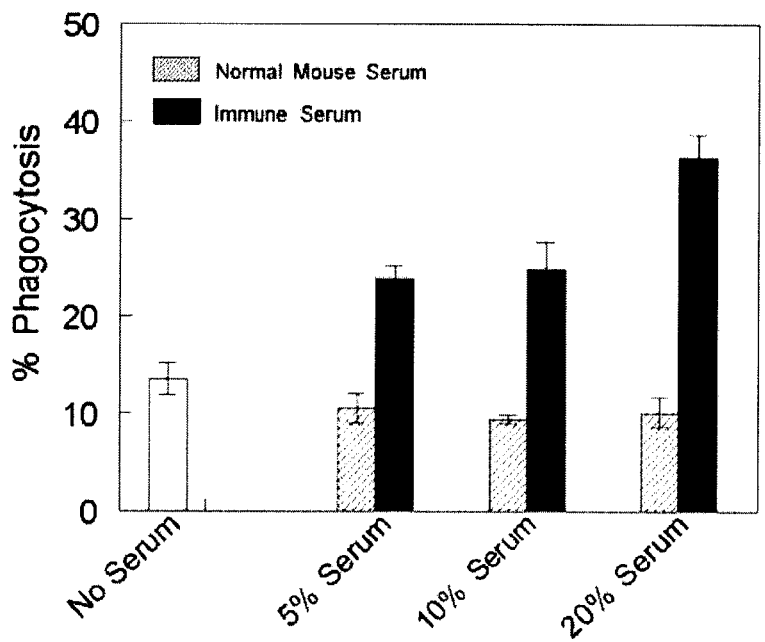
FIG. 7: Enhanced antibody-dependent phagocytic activity against F. tularensis subsp. novicida. F. tularensis subsp. novicida U112 was opsonized with varying concentrations of normal mouse serum (nms) or immune serum obtained from KKF24 vaccinated BALB/c mice. Phagocytosis was performed with the J774A.1 macrophage cell line (MOI of 1:1; bacteria to macrophage ratio). Cells were stained by anti-F. novicida LPS monoclonal ab #8.2 and anti-mouse CD11b and visualized by fluorescence microscopy. The percentage of macrophages containing bacteria was used as a measure of phagocytic activity. Results are shown as the mean percentage of macrophages containing fluorescent bacteria±SEM. 5% sera and nms: p<0.004; 10% sera and nms: p<0.005; 20% sera and nms: p<0.001. Results are representative of 2 independent experiments.

Antibodies Contribute to the Protection Conferred by i.n. Vaccination with *F. tularensis* Subsp. *novicida* ΔiglC To test the functional ability of such antibodies to mediate phagocytic uptake of *F. tularensis* subsp. *novicida*, the inventors utilized a complement-independent opsonophagocytic assay using the J774A.1 murine macrophage cell line (FIG. 7). Sera prepared from mice vaccinated with KKF24 and collected at 30 days efficiently mediated phagocytosis of the wildtype *F. tularensis* subsp. *novicida* strain U112 in a concentration dependent manner, whereas normal mouse serum did not. Similar results were observed with primary bone marrow derived macrophages (data not shown).

Figure 8:
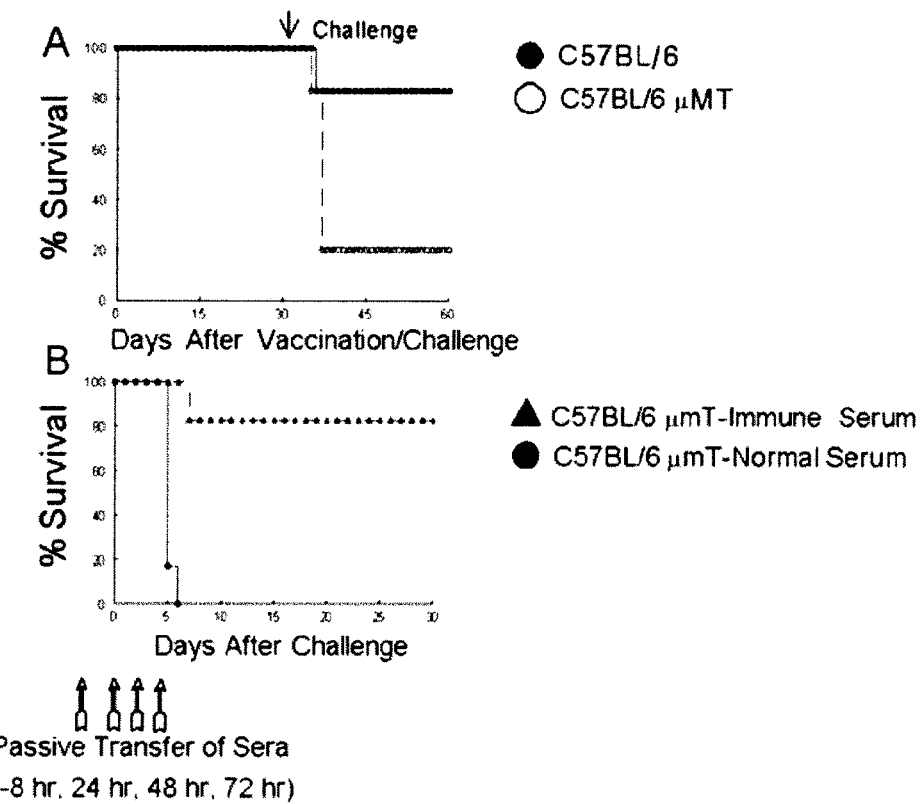
FIG. 8: Contribution of antibodies to KKF24-mediated protection. C57BL/6 µMT (B cell deficient) and C57BL/6 wild-type mice (6/group) were anesthetized with 3% Isoflurane and vaccinated i.n. with KKF24 ($10^6$ CFU) in 25 µl of sterile PBS. Animals were challenged after 30 days with 100 $LD_{50}$ (A) of wild type F. tularensis subsp. novicida U 112. (B) Adoptive transfer of immune or normal serum to naïve C57BL/6 µMT animals. Immune serum was prepared from C57BL/6 mice vaccinated i.n. with KKF24. Normal serum was collected from unvaccinated C57BL/6 mice. Naïve C57BL/6 µMT animals (6/group) were injected i.p. with 200 µl of either pooled immune or normal serum (1:3 dilution) at −8 h before i.n. challenge with 100 $LD_{50}$ of F. tularensis subsp. novicida. All animals were also injected with similar amounts of either immune or normal mouse serum at 24 h, 48 h and 72 h after bacterial challenge. Animals were monitored daily for morbidity and mortality. Results are representative of 2 independent experiments.

To further elucidate the role of humoral immunity in protection, B cell deficient (μMT) and wild type mice were vaccinated with $10^6$ CFU KKF24, then challenged 30 days later with 100 LD$_{50}$ of the *F. tularensis* subsp. *novicida* wild-type strain U112. As shown in FIG. 8A, vaccinated B cell deficient mice were found to be highly susceptible (20% survival) to the lethal wildtype subsp. *novicida* challenge, compared to similarly vaccinated wild-type (80% survival) mice. These results demonstrate a role for B cells in the protective immune response of ΔiglC-vaccinated mice.

To determine whether antibodies could reconstitute the protection in B cell deficient animals, adoptive transfer studies using immune or normal serum were performed. Adoptive transfer of immune serum from KKF24-vaccinated mice to naive B cell deficient mice afforded significant protection (80% survival) against i.n. lethal challenge with 100 LD$_{50}$ of the *F. tularensis* subsp. *novicida* wildtype strain U112 (FIG. 8B). In contrast, all the B cell deficient recipient mice receiving normal mouse serum succumbed (0% survival) to the challenge by day 6. These results indicate that antibodies contribute to the protection afforded by i.n. vaccination with *F. tularensis* subsp. *novicida* ΔiglC.

Example 6 i.n. Challenges of Mice with *F. tularensis* is a Reasonable Model for Human Pneumonic Tularemia The inventors utilized i.n. challenges of mice with *F. tularensis* subsp. *novicida* as a model for human pneumonic tularemia. Subsp. *novicida* infections are a reasonable model for tularemia because subsp. *novicida* has an LD$_{50}$ similar to the subsp. *tularensis* strain via the i.n. route in mice, and hallmarks of disease appear similar during infection caused by the two subspecies (Forsman et al., 1994; Lauriano et al., 2004; Pammit et al., 2004). Furthermore, subsp. *novicida* behaves similar to subsp. *tularensis* within human macrophages (Clemens et al., 2004; Santic et al., 2005), suggesting that the underlying pathogenic mechanism utilized by both subspecies is similar.

Protective efficacy of subsp. *novicida* ΔiglC (SEQ ID NO: 31), ΔiglA (SEQ ID NO: 32), ΔiglD (SEQ ID NO: 33), ΔmglA (SEQ ID NO: 34) strains against wildtype subsp. *novicida* challenge are illustrated in Tables 1 and 2.

TABLE 1

Virulence of *F. tularensis* subsp. *novicida* mutants in BALB/c mice:

| Strain | LD$_{50}$ intranasal | LD$_{50}$ intraperitoneal |
|---|---|---|
| mglA | >3.1 × $10^6$ | >2.3 × $10^4$ |
| iglA | >5.2 × $10^7$ | N.D. |
| iglC | >9.4 × $10^7$ | >1.7 × $10^6$ |
| iglD | >9.7 × $10^8$ | >1.8 × $10^7$ |

TABLE 2

Efficacy of Intranasal Vaccination with *F. tularensis* subsp. *novicida* mutants:

| Strain | Intranasal inoculum (CFU) | Intranasal WT challenge (CFU) | Survivors |
|---|---|---|---|
| None (PBS) | — | 1000 | 0/5 |
| mglA | 1.3 × $10^5$ | 1000 | 1/5 |
| iglA | 5.2 × $10^7$ | 1000 | 5/5 |
| iglC | 3.8 × $10^6$ | 1000 | 5/5 |
| iglD | 9.7 × $10^8$ | 1000 | 5/5 |

All of the compositions and/or methods disclosed and claimed in this specification can be made and executed without undue experimentation in light of the present disclosure. While the compositions and methods of this invention have been described in terms of certain embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265.
U.S. Pat. No. 4,275,149
U.S. Pat. No. 4,277,437
U.S. Pat. No. 4,366,241
U.S. Pat. No. 4,435,386
U.S. Pat. No. 4,472,509
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,866,034
U.S. Pat. No. 4,877,611
U.S. Pat. No. 4,938,948
U.S. Pat. No. 4,950,645
U.S. Pat. No. 5,021,236
U.S. Pat. No. 5,220,007
U.S. Pat. No. 5,284,760
U.S. Pat. No. 5,354,670
U.S. Pat. No. 5,366,878
U.S. Pat. No. 5,380,721
U.S. Pat. No. 5,389,514
U.S. Pat. No. 5,635,377
U.S. Pat. No. 5,789,166
U.S. Pat. No. 4,436,727
U.S. Pat. No. 4,436,728
U.S. Pat. No. 4,505,899
U.S. Pat. No. 4,505,900
U.S. Pat. No. 4,520,019
U.S. Pat. No. 4,579,945
Azuma et al., *Cell Immunol.*, 116(1):123-134, 1988.
Baron and Nano, *Mol. Microbiol.*, 29:247-259, 1998.
Cadwell and Joyce, *PCR Methods Appl.*, 2(1):28-33, 1992.
Christopher et al., *JAMA*, 278:412-417, 1997.
Clemens et al., *Infect. Immun.*, 72:3204-3217, 2004.
Cooley et al., *Science*, 239(4844):1121-1128, 1988.
Datsenko and Wanner, *PNAS*, 97(12):6640-45, 2000.
De Jager et al., *Semin. Nucl. Med.*, 23(2):165-179, 1993.
Dennis et al., *JAMA*, 285:2763-2773, 2001.
Doolittle and Ben-Zeev, *Methods Mol Biol*, 109:215-237, 1999.
Eigelsbach and Downs, *J. Immunol.*, 87:415-424, 1961.
Ellis et al., *Clin. Microbiol. Rev.*, 15:631-646, 2002.
Feldman et al., N. Engl. *J. Med.*, 345:1601-1606, 2001.
Forsman et al., Int. *J. Syst. Bacteriol.*, 44:38-46, 1994.
Forsman et al., Int. *J. Syst. Bacteriol.*, 44:38-46, 1994.
Freifelder, In: *Physical Biochemistry Applications to Biochemistry and Molecular Biology*, 2nd Ed. Wm. Freeman and Co., NY, 1982.
Golovliov et al., *FEMS Microbiol. Lett.*, 222:273-280, 2003.
Gray et al., *FEMS Microbiol. Lett.* 215, 53-56, 2002.
Gray et al., *FEMS Microbiol. Lett.*, 215:53-56, 2002.
Gulbis and Galand, *Hum. Pathol.*, 24(12):1271-1285, 1993.
Harris, *Ann. N.Y. Acad. Sci.*, 666:21-52, 1992.
Hunter et al., *Vaccine*, 9(4):250-256, 1991.
Husson et al., *J. Bacteriol.*, 172(2):519-524, 1990.
Jacobs et al., *Nature*, 327(6122):532-535, 1987.
Lai et al., *Microb. Pathog.*, 37:225-230, 2004.
Lauriano et al., *FEMS Microbiol. Lett.*, 229:195-202, 2003.
Lauriano et al., *Proc. Natl. Acad. Sci. USA*, 101:4246-4249, 2004.
Lindgren et al., *J. Med. Microbiol.*, 53:953-958, 2004.
Martin et al., *Nature*, 345(6277):739-743, 1990.
Murthy et al., *Cell Immunol.*, 230:56-64, 2004.
Nakamura et al., In: *Handbook of Experimental Immunology* ($4^{th}$ Ed.), Weir et al (Eds.), 1:27, Blackwell Scientific Publ., Oxford, 1987.
Pammit et al., *Antimicrob. Agents Chemother.*, 48:4513-4519, 2004.
PCT Appln. WO 91/16347
Rabinovich et al., *Science*, 265(5177):1401-1404, 1994.
Remington's Pharmaceutical Sciences, 18th Ed. Mack Printing Company, pp. 1289-1329, 1990.
Reyrat et al., *Infection and Immunity*, 66:4011-4017, 1998.
Sambrook et al., In: *Molecular cloning: a laboratory manual*, $2^{nd}$ Ed., Cold Spring Harbor Laboratory Press, Cold Spring Harbor, N.Y., 1987.
Sambrook et al, In: *Molecular cloning: a laboratory manual*, $2^{nd}$ Ed., Cold Spring Harbor Laboratory Press, Cold Spring Harbor, N.Y., 1989.
Santic et al., *Cell Microbiol.*, 7:957-967; 969-979, 2005.
Saslaw et al., *Arch. Intern Med.*, 107:134-146. 1961.
Snapper et al., *Proc. Natl. Acad. Sci. USA*, 85(18):6987-6991, 1988.
Takada et al., *Infection and Immunity*, 63(1):57-65, 1995a.
Tarnvik, *Rev. Infect. Dis.*, 11:440-451, 1989.
Telepnev et al., *Cell Microbiol.*, 5:41-51, 2003.
Titball et al., *Trends Microbiol.*, 11:118-123, 2003.
Wu et al., *Infect. Immun.*, 73:2644-2654, 2005.
Yamamoto et al., *Nature*, 334(6182):494-498, 1988.
Yin et al., *J. Biol. Resp. Modif.*, 8:190-205, 1989.

The invention claimed is:

1. A method for producing an attenuated *Francisella* bacterium comprising introducing an alteration in the nucleic acid sequence of the iglD gene of the bacterium.

2. The method of claim 1, wherein the alteration is a deletion, substitution, or insertion mutation.

3. The method of claim 1, wherein the iglD gene is not expressed.

4. The method of claim 1, wherein the bacterium expresses an inactive iglD protein.

5. The method of claim 1, wherein the bacterium lacks the iglD gene.

6. A composition comprising an attenuated *Francisella* bacterium with a genome that comprises an alteration in the nucleic acid sequence of the iglD gene of the bacterium.

7. The composition of claim 6, wherein the composition is comprised in a pharmaceutically acceptable vehicle.

8. The composition of claim 6, wherein the composition is formulated into a liquid, a spray, or an aerosol.

9. The method of claim 1, wherein the attenuated *Francisella* bacterium is further defined as attenuated *F. tularensis tularensis* (Type A).

10. The method of claim 6, wherein the attenuated *Francisella* bacterium is further defined as attenuated *F. tularensis tularensis* (Type A).

11. The method of claim 6, wherein the attenuated *Francisella* bacterium is further defined as attenuated *F. tularensis holarctica* (Type B).

12. The method of claim 6, wherein the attenuated *Francisella* bacterium is further defined as attenuated *F. tularensis novicida*.

\* \* \* \* \*

SEQUENCE LISTING

<160> NUMBER OF SEQ ID NOS: 34

<210> SEQ ID NO 1
<211> LENGTH: 636
<212> TYPE: DNA
<213> ORGANISM: Francisella tularensis
<220> FEATURE:
<221> NAME/KEY: CDS
<222> LOCATION: (1)..(633)

<400> SEQUENCE: 1

```
atg att atg agt gag atg ata aca aga caa cag gta aca agt ggc gag      48
Met Ile Met Ser Glu Met Ile Thr Arg Gln Gln Val Thr Ser Gly Glu
1               5                   10                  15 acc att cat gtg aga act gat cct act gca tgt ata gga tct cat cct      96
Thr Ile His Val Arg Thr Asp Pro Thr Ala Cys Ile Gly Ser His Pro
            20                  25                  30 aat tgt aga tta ttt att gat tct tta act ata gct ggg gag aaa ctt     144
Asn Cys Arg Leu Phe Ile Asp Ser Leu Thr Ile Ala Gly Glu Lys Leu
        35                  40                  45 gat aaa aat atc gtt gct ata gag ggt gga gag gat gtc acg aaa gct     192
Asp Lys Asn Ile Val Ala Ile Glu Gly Gly Glu Asp Val Thr Lys Ala
    50                  55                  60 gat tcg gct aca gct gct gct agt gta ata cgt tta tct ata acg cca     240
Asp Ser Ala Thr Ala Ala Ala Ser Val Ile Arg Leu Ser Ile Thr Pro
65                  70                  75                  80 ggc tct ata aat cca aca ata agt att act ctt ggt gtt cta att aaa     288
Gly Ser Ile Asn Pro Thr Ile Ser Ile Thr Leu Gly Val Leu Ile Lys
                85                  90                  95 tca aat gtc aga act aaa att gaa gag aaa gtt tcg agc ata tta caa     336
Ser Asn Val Arg Thr Lys Ile Glu Glu Lys Val Ser Ser Ile Leu Gln
            100                 105                 110 gca agt gct aca gat atg aaa att aag tta ggt aat tct aat aaa aaa     384
Ala Ser Ala Thr Asp Met Lys Ile Lys Leu Gly Asn Ser Asn Lys Lys
        115                 120                 125 caa gag tac aaa act gat gaa gca tgg ggt att atg ata gat cta tct     432
Gln Glu Tyr Lys Thr Asp Glu Ala Trp Gly Ile Met Ile Asp Leu Ser
    130                 135                 140 aat tta gag tta tat cca ata agt gct aag gct ttt agt att agt ata     480
Asn Leu Glu Leu Tyr Pro Ile Ser Ala Lys Ala Phe Ser Ile Ser Ile
145                 150                 155                 160 gag cca aca gaa ctt atg ggt gtt tca aaa gat gga atg agt tat cat     528
Glu Pro Thr Glu Leu Met Gly Val Ser Lys Asp Gly Met Ser Tyr His
                165                 170                 175 att ata tct ata gat ggt ctt aca aca tct caa gga agc ttg cca gta     576
Ile Ile Ser Ile Asp Gly Leu Thr Thr Ser Gln Gly Ser Leu Pro Val
            180                 185                 190 tgt tgc gca gct agc aca gat aaa gga gtt gct aaa ata gga tat att     624
Cys Cys Ala Ala Ser Thr Asp Lys Gly Val Ala Lys Ile Gly Tyr Ile
        195                 200                 205 gca gct gca tag                                                     636
Ala Ala Ala
    210
```

<210> SEQ ID NO 2
<211> LENGTH: 211
<212> TYPE: PRT
<213> ORGANISM: Francisella tularensis

<400> SEQUENCE: 2

```
Met Ile Met Ser Glu Met Ile Thr Arg Gln Gln Val Thr Ser Gly Glu
1               5                   10                  15

Thr Ile His Val Arg Thr Asp Pro Thr Ala Cys Ile Gly Ser His Pro
            20                  25                  30

Asn Cys Arg Leu Phe Ile Asp Ser Leu Thr Ile Ala Gly Glu Lys Leu
        35                  40                  45

Asp Lys Asn Ile Val Ala Ile Glu Gly Gly Glu Asp Val Thr Lys Ala
    50                  55                  60

Asp Ser Ala Thr Ala Ala Ala Ser Val Ile Arg Leu Ser Ile Thr Pro
65                  70                  75                  80
```

-continued

```
Gly Ser Ile Asn Pro Thr Ile Ser Ile Thr Leu Gly Val Leu Ile Lys
                85                  90                  95

Ser Asn Val Arg Thr Lys Ile Glu Glu Lys Val Ser Ser Ile Leu Gln
            100                 105                 110

Ala Ser Ala Thr Asp Met Lys Ile Lys Leu Gly Asn Ser Asn Lys Lys
        115                 120                 125

Gln Glu Tyr Lys Thr Asp Glu Ala Trp Gly Ile Met Ile Asp Leu Ser
    130                 135                 140

Asn Leu Glu Leu Tyr Pro Ile Ser Ala Lys Ala Phe Ser Ile Ser Ile
145                 150                 155                 160

Glu Pro Thr Glu Leu Met Gly Val Ser Lys Asp Gly Met Ser Tyr His
                165                 170                 175

Ile Ile Ser Ile Asp Gly Leu Thr Thr Ser Gln Gly Ser Leu Pro Val
            180                 185                 190

Cys Cys Ala Ala Ser Thr Asp Lys Gly Val Ala Lys Ile Gly Tyr Ile
        195                 200                 205

Ala Ala Ala
    210

<210> SEQ ID NO 3
<211> LENGTH: 636
<212> TYPE: DNA
<213> ORGANISM: Francisella tularensis
<220> FEATURE:
<221> NAME/KEY: CDS
<222> LOCATION: (1)..(633)

<400> SEQUENCE: 3 atg att atg agt gag atg ata aca aga caa cag gta aca agt ggc gag     48
Met Ile Met Ser Glu Met Ile Thr Arg Gln Gln Val Thr Ser Gly Glu
1               5                   10                  15 acc att cat gtg aga act gat cct act gca tgt ata gga tct cat cct     96
Thr Ile His Val Arg Thr Asp Pro Thr Ala Cys Ile Gly Ser His Pro
            20                  25                  30 aat tgt aga tta ttt att gat tct tta act ata gct ggg gag aaa ctt    144
Asn Cys Arg Leu Phe Ile Asp Ser Leu Thr Ile Ala Gly Glu Lys Leu
        35                  40                  45 gat aaa aat atc gtt gct ata gat ggt gga gag gat gtc acg aaa gct    192
Asp Lys Asn Ile Val Ala Ile Asp Gly Gly Glu Asp Val Thr Lys Ala
    50                  55                  60 gat tcg gct aca gct gct gct agt gta ata cgt tta tct ata acg cca    240
Asp Ser Ala Thr Ala Ala Ala Ser Val Ile Arg Leu Ser Ile Thr Pro
65                  70                  75                  80 ggc tct ata aat cca aca ata agt att act ctt ggt gtt cta att aaa    288
Gly Ser Ile Asn Pro Thr Ile Ser Ile Thr Leu Gly Val Leu Ile Lys
                85                  90                  95 tca aat gtt aga act aaa att gaa gag aaa gtt tcg agt ata tta caa    336
Ser Asn Val Arg Thr Lys Ile Glu Glu Lys Val Ser Ser Ile Leu Gln
            100                 105                 110 gca agt gct aca gat atg aaa att aag tta ggt aat tct aat aaa aaa    384
Ala Ser Ala Thr Asp Met Lys Ile Lys Leu Gly Asn Ser Asn Lys Lys
        115                 120                 125 caa gag tat aaa act gat gaa gca tgg ggt att atg ata gat cta tct    432
Gln Glu Tyr Lys Thr Asp Glu Ala Trp Gly Ile Met Ile Asp Leu Ser
    130                 135                 140 aat tta gag tta tat cca ata agt gct aag gct ttt agt att agt ata    480
Asn Leu Glu Leu Tyr Pro Ile Ser Ala Lys Ala Phe Ser Ile Ser Ile
145                 150                 155                 160
```

```
gag cca aca gaa ctt atg ggt gtt tca aaa gat gga atg aga tat cat    528
Glu Pro Thr Glu Leu Met Gly Val Ser Lys Asp Gly Met Arg Tyr His
            165                 170                 175 att ata tct ata gat ggt ctt aca aca tct caa gga agt ttg cca gta    576
Ile Ile Ser Ile Asp Gly Leu Thr Thr Ser Gln Gly Ser Leu Pro Val
        180                 185                 190 tgt tgc gca gct agc aca gat aaa gga gtt gct aaa ata gga tat att    624
Cys Cys Ala Ala Ser Thr Asp Lys Gly Val Ala Lys Ile Gly Tyr Ile
    195                 200                 205 gca gct gca tag                                                    636
Ala Ala Ala
    210

<210> SEQ ID NO 4
<211> LENGTH: 211
<212> TYPE: PRT
<213> ORGANISM: Francisella tularensis

<400> SEQUENCE: 4

Met Ile Met Ser Glu Met Ile Thr Arg Gln Gln Val Thr Ser Gly Glu
1               5                   10                  15

Thr Ile His Val Arg Thr Asp Pro Thr Ala Cys Ile Gly Ser His Pro
            20                  25                  30

Asn Cys Arg Leu Phe Ile Asp Ser Leu Thr Ile Ala Gly Glu Lys Leu
        35                  40                  45

Asp Lys Asn Ile Val Ala Ile Asp Gly Gly Glu Asp Val Thr Lys Ala
    50                  55                  60

Asp Ser Ala Thr Ala Ala Ser Val Ile Arg Leu Ser Ile Thr Pro
65                  70                  75                  80

Gly Ser Ile Asn Pro Thr Ile Ser Ile Thr Leu Gly Val Leu Ile Lys
                85                  90                  95

Ser Asn Val Arg Thr Lys Ile Glu Glu Lys Val Ser Ser Ile Leu Gln
            100                 105                 110

Ala Ser Ala Thr Asp Met Lys Ile Lys Leu Gly Asn Ser Asn Lys Lys
        115                 120                 125

Gln Glu Tyr Lys Thr Asp Glu Ala Trp Gly Ile Met Ile Asp Leu Ser
    130                 135                 140

Asn Leu Glu Leu Tyr Pro Ile Ser Ala Lys Ala Phe Ser Ile Ser Ile
145                 150                 155                 160

Glu Pro Thr Glu Leu Met Gly Val Ser Lys Asp Gly Met Arg Tyr His
                165                 170                 175

Ile Ile Ser Ile Asp Gly Leu Thr Thr Ser Gln Gly Ser Leu Pro Val
            180                 185                 190

Cys Cys Ala Ala Ser Thr Asp Lys Gly Val Ala Lys Ile Gly Tyr Ile
        195                 200                 205

Ala Ala Ala
    210

<210> SEQ ID NO 5
<211> LENGTH: 630
<212> TYPE: DNA
<213> ORGANISM: Francisella tularensis
<220> FEATURE:
<221> NAME/KEY: CDS
<222> LOCATION: (1)..(627)

<400> SEQUENCE: 5 atg agt gag atg ata aca aga caa cag gta aca agt ggc gag acc att    48
Met Ser Glu Met Ile Thr Arg Gln Gln Val Thr Ser Gly Glu Thr Ile
```

```
                1               5                       10                      15
cat gtg aga act gat cct act gca tgt ata gga tct cat cct aat tgt         96
His Val Arg Thr Asp Pro Thr Ala Cys Ile Gly Ser His Pro Asn Cys
            20                      25                      30 aga tta ttt att gat tct tta act ata gct ggg gag aaa ctt gat aaa         144
Arg Leu Phe Ile Asp Ser Leu Thr Ile Ala Gly Glu Lys Leu Asp Lys
            35                      40                      45 aat atc gtt gct ata gag ggt gga gag gat gtc acg aaa gct gat tcg         192
Asn Ile Val Ala Ile Glu Gly Gly Glu Asp Val Thr Lys Ala Asp Ser
        50                      55                      60 gct aca gct gct gct agt gta ata cgt tta tct ata acg cca ggc tct         240
Ala Thr Ala Ala Ala Ser Val Ile Arg Leu Ser Ile Thr Pro Gly Ser
65                      70                      75                      80 ata aat cca aca ata agt att act ctt ggt gtt cta att aaa tca aat         288
Ile Asn Pro Thr Ile Ser Ile Thr Leu Gly Val Leu Ile Lys Ser Asn
                    85                      90                      95 gtt aga act aaa att gaa gag aaa gtt tcg agt ata tta caa gca agt         336
Val Arg Thr Lys Ile Glu Glu Lys Val Ser Ser Ile Leu Gln Ala Ser
                100                     105                     110 gct aca gat atg aaa att aag tta ggt aat tct aat aaa aaa caa gag         384
Ala Thr Asp Met Lys Ile Lys Leu Gly Asn Ser Asn Lys Lys Gln Glu
            115                     120                     125 tat aaa act gat gaa gca tgg ggt att atg ata gat cta tct aat tta         432
Tyr Lys Thr Asp Glu Ala Trp Gly Ile Met Ile Asp Leu Ser Asn Leu
        130                     135                     140 gag tta tat cca ata agt gct aag gct ttt agt att agt ata gag cca         480
Glu Leu Tyr Pro Ile Ser Ala Lys Ala Phe Ser Ile Ser Ile Glu Pro
145                     150                     155                     160 aca gaa ctt atg ggt gtt tca aaa gat gga atg agt tat cat att ata         528
Thr Glu Leu Met Gly Val Ser Lys Asp Gly Met Ser Tyr His Ile Ile
                    165                     170                     175 tct ata gat ggt ctt aca aca tct caa gga agc ttg cca gta tgt tgc         576
Ser Ile Asp Gly Leu Thr Thr Ser Gln Gly Ser Leu Pro Val Cys Cys
                180                     185                     190 gca gct agc aca gat aaa gga gtt gct aaa ata gga tat att gca gct         624
Ala Ala Ser Thr Asp Lys Gly Val Ala Lys Ile Gly Tyr Ile Ala Ala
            195                     200                     205 gca tag                                                                 630
Ala

<210> SEQ ID NO 6
<211> LENGTH: 209
<212> TYPE: PRT
<213> ORGANISM: Francisella tularensis

<400> SEQUENCE: 6

Met Ser Glu Met Ile Thr Arg Gln Gln Val Thr Ser Gly Glu Thr Ile
1               5                   10                  15

His Val Arg Thr Asp Pro Thr Ala Cys Ile Gly Ser His Pro Asn Cys
            20                  25                  30

Arg Leu Phe Ile Asp Ser Leu Thr Ile Ala Gly Glu Lys Leu Asp Lys
        35                  40                  45

Asn Ile Val Ala Ile Glu Gly Gly Glu Asp Val Thr Lys Ala Asp Ser
    50                  55                  60

Ala Thr Ala Ala Ala Ser Val Ile Arg Leu Ser Ile Thr Pro Gly Ser
65                  70                  75                  80

Ile Asn Pro Thr Ile Ser Ile Thr Leu Gly Val Leu Ile Lys Ser Asn
                85                  90                  95
```

```
Val Arg Thr Lys Ile Glu Glu Lys Val Ser Ser Ile Leu Gln Ala Ser
            100                 105                 110

Ala Thr Asp Met Lys Ile Lys Leu Gly Asn Ser Asn Lys Lys Gln Glu
        115                 120                 125

Tyr Lys Thr Asp Glu Ala Trp Gly Ile Met Ile Asp Leu Ser Asn Leu
    130                 135                 140

Glu Leu Tyr Pro Ile Ser Ala Lys Ala Phe Ser Ile Ser Ile Glu Pro
145                 150                 155                 160

Thr Glu Leu Met Gly Val Ser Lys Asp Gly Met Ser Tyr His Ile Ile
            165                 170                 175

Ser Ile Asp Gly Leu Thr Thr Ser Gln Gly Ser Leu Pro Val Cys Cys
            180                 185                 190

Ala Ala Ser Thr Asp Lys Gly Val Ala Lys Ile Gly Tyr Ile Ala Ala
            195                 200                 205

Ala
```

```
<210> SEQ ID NO 7
<211> LENGTH: 1197
<212> TYPE: DNA
<213> ORGANISM: Francisella tularensis
<220> FEATURE:
<221> NAME/KEY: CDS
<222> LOCATION: (1)..(1194)
<220> FEATURE:
<221> NAME/KEY: modified_res
<222> LOCATION: (40)
<223> OTHER INFORMATION: x = can be any naturally occurring amino acid

<400> SEQUENCE: 7
```

```
atg ttt cta gaa agg att tat tgg gaa gat ggt tta aga tta gat agc      48
Met Phe Leu Glu Arg Ile Tyr Trp Glu Asp Gly Leu Arg Leu Asp Ser
1               5                   10                  15 gat att tta gat aag tca aat cta tct gtt tta gaa agg tta agc acc      96
Asp Ile Leu Asp Lys Ser Asn Leu Ser Val Leu Glu Arg Leu Ser Thr
            20                  25                  30 gca agc tat ttg cca gct aat cyt aat aag gga atc gtt agc ttt gat     144
Ala Ser Tyr Leu Pro Ala Asn Xaa Asn Lys Gly Ile Val Ser Phe Asp
        35                  40                  45 tta gat gtt gaa agt ttg cag aca ggt ctt atc ctt ata aaa gat ctt     192
Leu Asp Val Glu Ser Leu Gln Thr Gly Leu Ile Leu Ile Lys Asp Leu
    50                  55                  60 aaa ttg tac tta gat gaa aaa aat ttt gtt ttt tat gat aag tct tat     240
Lys Leu Tyr Leu Asp Glu Lys Asn Phe Val Phe Tyr Asp Lys Ser Tyr
65                  70                  75                  80 ccg tta tct tta caa ata atg act gat aag tta agt gat gaa ata ccc     288
Pro Leu Ser Leu Gln Ile Met Thr Asp Lys Leu Ser Asp Glu Ile Pro
                85                  90                  95 tta ttt ctg aat atc aga gag aaa gta att gaa aaa aat ggg gtt aaa     336
Leu Phe Leu Asn Ile Arg Glu Lys Val Ile Glu Lys Asn Gly Val Lys
            100                 105                 110 tat atc tat aat caa ttg tca tta tca tta gag cat agc tat ggt ttt     384
Tyr Ile Tyr Asn Gln Leu Ser Leu Ser Leu Glu His Ser Tyr Gly Phe
        115                 120                 125 aaa cat agc atc caa att gca tta ttt agg cta gat aga ggg cga tta     432
Lys His Ser Ile Gln Ile Ala Leu Phe Arg Leu Asp Arg Gly Arg Leu
    130                 135                 140 gta cca gaa att tat gac ttt ccg cta tta act ctt aat cat tat tat     480
Val Pro Glu Ile Tyr Asp Phe Pro Leu Leu Thr Leu Asn His Tyr Tyr
145                 150                 155                 160 tta ggt gat att ttt gta aaa ctt aat agg act gtt tct gaa cta aag     528
```

```
                                                             -continued

Leu Gly Asp Ile Phe Val Lys Leu Asn Arg Thr Val Ser Glu Leu Lys
            165                 170                 175 tct ttt aat cgc ttt gtt ttt tca gct tca aga tct tat gcg tca ata    576
Ser Phe Asn Arg Phe Val Phe Ser Ala Ser Arg Ser Tyr Ala Ser Ile
        180                 185                 190 tta ctt gta ttt ttg att aat aaa tta gaa aga gaa ttg aag ttt gcg    624
Leu Leu Val Phe Leu Ile Asn Lys Leu Glu Arg Glu Leu Lys Phe Ala
    195                 200                 205 gaa tct aat agg gca aat agt tcc ccg aaa caa ata ttt gat tta att    672
Glu Ser Asn Arg Ala Asn Ser Ser Pro Lys Gln Ile Phe Asp Leu Ile
210                 215                 220 gat gat att tac agc tta att caa ctt aac cta gat aaa gtt gaa gag    720
Asp Asp Ile Tyr Ser Leu Ile Gln Leu Asn Leu Asp Lys Val Glu Glu
225                 230                 235                 240 ctt gat agc att gaa ttt gat ttc caa aag cct ttg act aaa tta aat    768
Leu Asp Ser Ile Glu Phe Asp Phe Gln Lys Pro Leu Thr Lys Leu Asn
                245                 250                 255 cta ctt gct gat aga ttg tta act ctt tgt gag tat aga aag att aat    816
Leu Leu Ala Asp Arg Leu Leu Thr Leu Cys Glu Tyr Arg Lys Ile Asn
            260                 265                 270 aac ttt atc aga ttt gaa ttg cat gga aaa aaa tat ata tgt gaa agc    864
Asn Phe Ile Arg Phe Glu Leu His Gly Lys Lys Tyr Ile Cys Glu Ser
        275                 280                 285 ttt cct gaa gag ttt ttt gtt gct act aga tac tat ctt ttc ctt aaa    912
Phe Pro Glu Glu Phe Phe Val Ala Thr Arg Tyr Tyr Leu Phe Leu Lys
    290                 295                 300 agg aaa gca aca gct cca gcc aat gta agg ttt gaa aat aag aat gct    960
Arg Lys Ala Thr Ala Pro Ala Asn Val Arg Phe Glu Asn Lys Asn Ala
305                 310                 315                 320 ctg aga att act agt ata agt aga aat aag aat att gta act ttg tct   1008
Leu Arg Ile Thr Ser Ile Ser Arg Asn Lys Asn Ile Val Thr Leu Ser
                325                 330                 335 ctt tca gga gta aaa ctg gtt gac gtt gaa tgt tct atg att aat ttt   1056
Leu Ser Gly Val Lys Leu Val Asp Val Glu Cys Ser Met Ile Asn Phe
            340                 345                 350 aca act aga ttt gat aat atc gat gca ata tat gaa att caa aaa ggt   1104
Thr Thr Arg Phe Asp Asn Ile Asp Ala Ile Tyr Glu Ile Gln Lys Gly
        355                 360                 365 tct gag tgg gat ttt ata tta gcg gat agt agt gcg gtt ttt acg gct   1152
Ser Glu Trp Asp Phe Ile Leu Ala Asp Ser Ser Ala Val Phe Thr Ala
    370                 375                 380 ttt gaa ggt agt gag aat ttt gat ttc ttt ata gcc ttt tct taa       1197
Phe Glu Gly Ser Glu Asn Phe Asp Phe Phe Ile Ala Phe Ser
385                 390                 395

<210> SEQ ID NO 8
<211> LENGTH: 398
<212> TYPE: PRT
<213> ORGANISM: Francisella tularensis
<220> FEATURE:
<221> NAME/KEY: misc_feature
<222> LOCATION: (40)..(40)
<223> OTHER INFORMATION: The 'Xaa' at location 40 stands for Pro, or
      Leu.

<400> SEQUENCE: 8

Met Phe Leu Glu Arg Ile Tyr Trp Glu Asp Gly Leu Arg Leu Asp Ser
1               5                   10                  15

Asp Ile Leu Asp Lys Ser Asn Leu Ser Val Leu Glu Arg Leu Ser Thr
            20                  25                  30

Ala Ser Tyr Leu Pro Ala Asn Xaa Asn Lys Gly Ile Val Ser Phe Asp
```

```
            35                  40                  45
Leu Asp Val Glu Ser Leu Gln Thr Gly Leu Ile Leu Ile Lys Asp Leu
 50                  55                  60

Lys Leu Tyr Leu Asp Glu Lys Asn Phe Val Phe Tyr Asp Lys Ser Tyr
 65                  70                  75                  80

Pro Leu Ser Leu Gln Ile Met Thr Asp Lys Leu Ser Asp Glu Ile Pro
                 85                  90                  95

Leu Phe Leu Asn Ile Arg Glu Lys Val Ile Glu Lys Asn Gly Val Lys
                100                 105                 110

Tyr Ile Tyr Asn Gln Leu Ser Leu Ser Leu Glu His Ser Tyr Gly Phe
            115                 120                 125

Lys His Ser Ile Gln Ile Ala Leu Phe Arg Leu Asp Arg Gly Arg Leu
        130                 135                 140

Val Pro Glu Ile Tyr Asp Phe Pro Leu Leu Thr Leu Asn His Tyr Tyr
145                 150                 155                 160

Leu Gly Asp Ile Phe Val Lys Leu Asn Arg Thr Val Ser Glu Leu Lys
                165                 170                 175

Ser Phe Asn Arg Phe Val Phe Ser Ala Ser Arg Ser Tyr Ala Ser Ile
            180                 185                 190

Leu Leu Val Phe Leu Ile Asn Lys Leu Glu Arg Glu Leu Lys Phe Ala
        195                 200                 205

Glu Ser Asn Arg Ala Asn Ser Ser Pro Lys Gln Ile Phe Asp Leu Ile
210                 215                 220

Asp Asp Ile Tyr Ser Leu Ile Gln Leu Asn Leu Asp Lys Val Glu Glu
225                 230                 235                 240

Leu Asp Ser Ile Glu Phe Asp Phe Gln Lys Pro Leu Thr Lys Leu Asn
                245                 250                 255

Leu Leu Ala Asp Arg Leu Leu Thr Leu Cys Glu Tyr Arg Lys Ile Asn
            260                 265                 270

Asn Phe Ile Arg Phe Glu Leu His Gly Lys Lys Tyr Ile Cys Glu Ser
        275                 280                 285

Phe Pro Glu Glu Phe Phe Val Ala Thr Arg Tyr Tyr Leu Phe Leu Lys
290                 295                 300

Arg Lys Ala Thr Ala Pro Ala Asn Val Arg Phe Glu Asn Lys Asn Ala
305                 310                 315                 320

Leu Arg Ile Thr Ser Ile Ser Arg Asn Lys Asn Ile Val Thr Leu Ser
                325                 330                 335

Leu Ser Gly Val Lys Leu Val Asp Val Glu Cys Ser Met Ile Asn Phe
            340                 345                 350

Thr Thr Arg Phe Asp Asn Ile Asp Ala Ile Tyr Glu Ile Gln Lys Gly
        355                 360                 365

Ser Glu Trp Asp Phe Ile Leu Ala Asp Ser Ser Ala Val Phe Thr Ala
370                 375                 380

Phe Glu Gly Ser Glu Asn Phe Asp Phe Phe Ile Ala Phe Ser
385                 390                 395

<210> SEQ ID NO 9
<211> LENGTH: 1206
<212> TYPE: DNA
<213> ORGANISM: Francisella tularensis
<220> FEATURE:
<221> NAME/KEY: CDS
<222> LOCATION: (1)..(1203)

<400> SEQUENCE: 9
```

| | | | | | | | | | | | | | | | | |
|---|---|---|---|---|---|---|---|---|---|---|---|---|---|---|---|---|
| ttg | att | cta | atg | ttt | cta | gaa | agg | att | tat | tgg | gaa | gat | ggt | tta | aga | 48 |
| Met | Ile | Leu | Met | Phe | Leu | Glu | Arg | Ile | Tyr | Trp | Glu | Asp | Gly | Leu | Arg | |
| 1 | | | | 5 | | | | | 10 | | | | | 15 | | |
| tta | gat | agc | gat | att | tta | gat | aag | tca | aat | cta | tct | gtt | tta | gaa | agg | 96 |
| Leu | Asp | Ser | Asp | Ile | Leu | Asp | Lys | Ser | Asn | Leu | Ser | Val | Leu | Glu | Arg | |
| | | | 20 | | | | | 25 | | | | | 30 | | | |
| tta | agc | acc | gca | agc | tat | ttg | cca | gct | aat | ctt | aat | aag | gga | atc | gtt | 144 |
| Leu | Ser | Thr | Ala | Ser | Tyr | Leu | Pro | Ala | Asn | Leu | Asn | Lys | Gly | Ile | Val | |
| | | 35 | | | | | 40 | | | | | 45 | | | | |
| agc | ttt | gat | tta | gat | gtt | gaa | agt | ttg | cag | aca | ggt | ctt | atc | ctt | ata | 192 |
| Ser | Phe | Asp | Leu | Asp | Val | Glu | Ser | Leu | Gln | Thr | Gly | Leu | Ile | Leu | Ile | |
| | 50 | | | | | 55 | | | | | 60 | | | | | |
| aaa | gat | ctt | aaa | ttg | tac | tta | gat | gaa | aaa | aat | ttt | gtt | ttt | tat | gat | 240 |
| Lys | Asp | Leu | Lys | Leu | Tyr | Leu | Asp | Glu | Lys | Asn | Phe | Val | Phe | Tyr | Asp | |
| 65 | | | | | 70 | | | | | 75 | | | | | 80 | |
| aag | tct | tat | ccg | tta | tct | tta | caa | ata | atg | act | gat | aag | tta | agt | gat | 288 |
| Lys | Ser | Tyr | Pro | Leu | Ser | Leu | Gln | Ile | Met | Thr | Asp | Lys | Leu | Ser | Asp | |
| | | | | 85 | | | | | 90 | | | | | 95 | | |
| gaa | atc | ccc | tta | ttt | ctg | aat | atc | aga | gag | aaa | gta | att | gaa | aaa | aat | 336 |
| Glu | Ile | Pro | Leu | Phe | Leu | Asn | Ile | Arg | Glu | Lys | Val | Ile | Glu | Lys | Asn | |
| | | | 100 | | | | | 105 | | | | | 110 | | | |
| ggg | att | aaa | tat | atc | tat | aat | caa | ttg | tca | tta | tca | tta | gag | cat | agc | 384 |
| Gly | Ile | Lys | Tyr | Ile | Tyr | Asn | Gln | Leu | Ser | Leu | Ser | Leu | Glu | His | Ser | |
| | | 115 | | | | | 120 | | | | | 125 | | | | |
| tat | ggt | ttt | aaa | cat | agc | atc | caa | att | gca | tta | ttt | agg | tta | gat | aga | 432 |
| Tyr | Gly | Phe | Lys | His | Ser | Ile | Gln | Ile | Ala | Leu | Phe | Arg | Leu | Asp | Arg | |
| | 130 | | | | | 135 | | | | | 140 | | | | | |
| ggg | cga | tta | gta | cca | gaa | att | tat | gac | ttc | ccg | cta | tta | act | ctt | aat | 480 |
| Gly | Arg | Leu | Val | Pro | Glu | Ile | Tyr | Asp | Phe | Pro | Leu | Leu | Thr | Leu | Asn | |
| 145 | | | | | 150 | | | | | 155 | | | | | 160 | |
| cat | tat | tat | tta | ggt | gat | att | ttt | gta | aaa | ctt | aat | agg | act | gtt | tct | 528 |
| His | Tyr | Tyr | Leu | Gly | Asp | Ile | Phe | Val | Lys | Leu | Asn | Arg | Thr | Val | Ser | |
| | | | | 165 | | | | | 170 | | | | | 175 | | |
| gaa | cta | aag | tct | ttt | aat | cgc | ttt | gtt | ttt | tca | gct | tca | aga | tct | tat | 576 |
| Glu | Leu | Lys | Ser | Phe | Asn | Arg | Phe | Val | Phe | Ser | Ala | Ser | Arg | Ser | Tyr | |
| | | | 180 | | | | | 185 | | | | | 190 | | | |
| gcg | tca | ata | tta | ctt | gta | ttt | ttg | att | aat | aaa | tta | gaa | aga | gaa | ttg | 624 |
| Ala | Ser | Ile | Leu | Leu | Val | Phe | Leu | Ile | Asn | Lys | Leu | Glu | Arg | Glu | Leu | |
| | | 195 | | | | | 200 | | | | | 205 | | | | |
| aag | ttc | gca | gaa | tct | aat | agg | gca | aat | agt | tac | ccg | aaa | caa | ata | ttt | 672 |
| Lys | Phe | Ala | Glu | Ser | Asn | Arg | Ala | Asn | Ser | Tyr | Pro | Lys | Gln | Ile | Phe | |
| | 210 | | | | | 215 | | | | | 220 | | | | | |
| gat | tta | att | gat | gat | att | tac | agc | tta | att | caa | ctt | aac | cta | gat | aaa | 720 |
| Asp | Leu | Ile | Asp | Asp | Ile | Tyr | Ser | Leu | Ile | Gln | Leu | Asn | Leu | Asp | Lys | |
| 225 | | | | | 230 | | | | | 235 | | | | | 240 | |
| gtt | gaa | gag | ctt | gat | agc | att | gaa | ttt | gat | ttc | caa | aag | cct | ttg | act | 768 |
| Val | Glu | Glu | Leu | Asp | Ser | Ile | Glu | Phe | Asp | Phe | Gln | Lys | Pro | Leu | Thr | |
| | | | | 245 | | | | | 250 | | | | | 255 | | |
| aaa | tta | aat | cta | ctt | gct | gat | aga | ttg | tta | act | ctt | tgt | gag | tat | aga | 816 |
| Lys | Leu | Asn | Leu | Leu | Ala | Asp | Arg | Leu | Leu | Thr | Leu | Cys | Glu | Tyr | Arg | |
| | | | 260 | | | | | 265 | | | | | 270 | | | |
| aag | att | aat | aac | ttt | atc | aga | ttt | gaa | ttg | cat | gga | aaa | aaa | tat | ata | 864 |
| Lys | Ile | Asn | Asn | Phe | Ile | Arg | Phe | Glu | Leu | His | Gly | Lys | Lys | Tyr | Ile | |
| | | 275 | | | | | 280 | | | | | 285 | | | | |
| tgt | gaa | agc | ttt | cct | gaa | gag | ttt | ttt | gtt | gct | act | aga | tac | tat | ctt | 912 |
| Cys | Glu | Ser | Phe | Pro | Glu | Glu | Phe | Phe | Val | Ala | Thr | Arg | Tyr | Tyr | Leu | |
| | 290 | | | | | 295 | | | | | 300 | | | | | |
| ttc | ctt | aaa | agg | aaa | gca | aca | gct | cca | gcc | aat | gta | agg | ttt | gaa | aat | 960 |
| Phe | Leu | Lys | Arg | Lys | Ala | Thr | Ala | Pro | Ala | Asn | Val | Arg | Phe | Glu | Asn | |
| 305 | | | | | 310 | | | | | 315 | | | | | 320 | |

```
aag aat gct ctg aga att act agt ata agt aga aat aag aat att gta    1008
Lys Asn Ala Leu Arg Ile Thr Ser Ile Ser Arg Asn Lys Asn Ile Val
            325                 330                 335 gct ctg tct ctt tca gga gta aaa ctg gtt gac gtt gaa tgt tct atg    1056
Ala Leu Ser Leu Ser Gly Val Lys Leu Val Asp Val Glu Cys Ser Met
        340                 345                 350 att aat ttt aca act aga ttt gat aat atc gat gca ata tat gaa att    1104
Ile Asn Phe Thr Thr Arg Phe Asp Asn Ile Asp Ala Ile Tyr Glu Ile
                355                 360                 365 caa aaa ggt tct gag tgg gat ttt ata tta gcg gat agt agt gcg gtt    1152
Gln Lys Gly Ser Glu Trp Asp Phe Ile Leu Ala Asp Ser Ser Ala Val
    370                 375                 380 ttt acg gct ttt gaa ggt agt gag aat ttt gat ttc ttt ata gcc ttt    1200
Phe Thr Ala Phe Glu Gly Ser Glu Asn Phe Asp Phe Phe Ile Ala Phe
385                 390                 395                 400 tct taa                                                            1206
Ser
```

<210> SEQ ID NO 10
<211> LENGTH: 401
<212> TYPE: PRT
<213> ORGANISM: Francisella tularensis

<400> SEQUENCE: 10

```
Met Ile Leu Met Phe Leu Glu Arg Ile Tyr Trp Glu Asp Gly Leu Arg
1               5                   10                  15

Leu Asp Ser Asp Ile Leu Asp Lys Ser Asn Leu Ser Val Leu Glu Arg
            20                  25                  30

Leu Ser Thr Ala Ser Tyr Leu Pro Ala Asn Leu Asn Lys Gly Ile Val
        35                  40                  45

Ser Phe Asp Leu Asp Val Glu Ser Leu Gln Thr Gly Leu Ile Leu Ile
    50                  55                  60

Lys Asp Leu Lys Leu Tyr Leu Asp Glu Lys Asn Phe Val Phe Tyr Asp
65                  70                  75                  80

Lys Ser Tyr Pro Leu Ser Leu Gln Ile Met Thr Asp Lys Leu Ser Asp
                85                  90                  95

Glu Ile Pro Leu Phe Leu Asn Ile Arg Glu Lys Val Ile Glu Lys Asn
            100                 105                 110

Gly Ile Lys Tyr Ile Tyr Asn Gln Leu Ser Leu Ser Leu Glu His Ser
        115                 120                 125

Tyr Gly Phe Lys His Ser Ile Gln Ile Ala Leu Phe Arg Leu Asp Arg
    130                 135                 140

Gly Arg Leu Val Pro Glu Ile Tyr Asp Phe Pro Leu Leu Thr Leu Asn
145                 150                 155                 160

His Tyr Tyr Leu Gly Asp Ile Phe Val Lys Leu Asn Arg Thr Val Ser
                165                 170                 175

Glu Leu Lys Ser Phe Asn Arg Phe Val Phe Ser Ala Ser Arg Ser Tyr
            180                 185                 190

Ala Ser Ile Leu Leu Val Phe Leu Ile Asn Lys Leu Glu Arg Glu Leu
        195                 200                 205

Lys Phe Ala Glu Ser Asn Arg Ala Asn Ser Tyr Pro Lys Gln Ile Phe
    210                 215                 220

Asp Leu Ile Asp Asp Ile Tyr Ser Leu Ile Gln Leu Asn Leu Asp Lys
225                 230                 235                 240

Val Glu Glu Leu Asp Ser Ile Glu Phe Asp Phe Gln Lys Pro Leu Thr
                245                 250                 255
```

```
Lys Leu Asn Leu Leu Ala Asp Arg Leu Leu Thr Leu Cys Glu Tyr Arg
            260                 265                 270

Lys Ile Asn Asn Phe Ile Arg Phe Glu Leu His Gly Lys Lys Tyr Ile
        275                 280                 285

Cys Glu Ser Phe Pro Glu Glu Phe Val Ala Thr Arg Tyr Tyr Leu
    290                 295                 300

Phe Leu Lys Arg Lys Ala Thr Ala Pro Ala Asn Val Arg Phe Glu Asn
305                 310                 315                 320

Lys Asn Ala Leu Arg Ile Thr Ser Ile Ser Arg Asn Lys Asn Ile Val
                325                 330                 335

Ala Leu Ser Leu Ser Gly Val Lys Leu Val Asp Val Glu Cys Ser Met
            340                 345                 350

Ile Asn Phe Thr Thr Arg Phe Asp Asn Ile Asp Ala Ile Tyr Glu Ile
        355                 360                 365

Gln Lys Gly Ser Glu Trp Asp Phe Ile Leu Ala Asp Ser Ser Ala Val
    370                 375                 380

Phe Thr Ala Phe Glu Gly Ser Glu Asn Phe Asp Phe Phe Ile Ala Phe
385                 390                 395                 400

Ser

<210> SEQ ID NO 11
<211> LENGTH: 1197
<212> TYPE: DNA
<213> ORGANISM: Francisella tularensis
<220> FEATURE:
<221> NAME/KEY: CDS
<222> LOCATION: (1)..(1194)

<400> SEQUENCE: 11 atg ttt cta gaa agg att tat tgg gaa gat ggt tta aga tta gat agc      48
Met Phe Leu Glu Arg Ile Tyr Trp Glu Asp Gly Leu Arg Leu Asp Ser
1               5                   10                  15 gat att tta gat aag tca aat cta tct gtt tta gaa agg tta agc acc      96
Asp Ile Leu Asp Lys Ser Asn Leu Ser Val Leu Glu Arg Leu Ser Thr
                20                  25                  30 gcg agc tat ttg cca gct aat ctt aat aag gga atc gtt agc ttt gat     144
Ala Ser Tyr Leu Pro Ala Asn Leu Asn Lys Gly Ile Val Ser Phe Asp
            35                  40                  45 tta gat gtt gaa agt ttg cag aca ggt ctt atc ctt ata aaa gat ctt     192
Leu Asp Val Glu Ser Leu Gln Thr Gly Leu Ile Leu Ile Lys Asp Leu
        50                  55                  60 aaa ttg tac tta gat gaa aaa aat ttt gtt ttt tat gat aag tct tat     240
Lys Leu Tyr Leu Asp Glu Lys Asn Phe Val Phe Tyr Asp Lys Ser Tyr
65                  70                  75                  80 ccg tta tct tta caa ata atg act gat aag tta agt gat gaa atc ccc     288
Pro Leu Ser Leu Gln Ile Met Thr Asp Lys Leu Ser Asp Glu Ile Pro
                85                  90                  95 tta ttt ctg aat atc aga gag aaa gta att gaa aaa aat ggg att aaa     336
Leu Phe Leu Asn Ile Arg Glu Lys Val Ile Glu Lys Asn Gly Ile Lys
            100                 105                 110 tat atc tat aat caa ttg tca tta tca tta gag cat agc tat ggt ttt     384
Tyr Ile Tyr Asn Gln Leu Ser Leu Ser Leu Glu His Ser Tyr Gly Phe
        115                 120                 125 aaa cat agc atc caa att gca tta ttt agg tta gat aga ggg cga tta     432
Lys His Ser Ile Gln Ile Ala Leu Phe Arg Leu Asp Arg Gly Arg Leu
    130                 135                 140 gta cca gaa att tat gac ttc ccg cta tta act ctt aat cat tat tat     480
Val Pro Glu Ile Tyr Asp Phe Pro Leu Leu Thr Leu Asn His Tyr Tyr
```

```
                    145                 150                 155                 160
tta ggt gat att ttt gta aaa ctt aat agg act gtt tct gaa cta aag      528
Leu Gly Asp Ile Phe Val Lys Leu Asn Arg Thr Val Ser Glu Leu Lys
                    165                 170                 175 tct ttt aat cgc ttt gtt ttt tca gct tca aga tct tat gcg tca ata      576
Ser Phe Asn Arg Phe Val Phe Ser Ala Ser Arg Ser Tyr Ala Ser Ile
                180                 185                 190 tta ctt gta ttt ttg att aat aaa tta gaa aga gaa ttg aag ttc gca      624
Leu Leu Val Phe Leu Ile Asn Lys Leu Glu Arg Glu Leu Lys Phe Ala
            195                 200                 205 gaa tct aat agg gca aat agt tcc ccg aaa caa ata ttt gat tta att      672
Glu Ser Asn Arg Ala Asn Ser Ser Pro Lys Gln Ile Phe Asp Leu Ile
        210                 215                 220 gat gat att tac agc tta att caa ctt aac cta gat aaa gtt gaa gag      720
Asp Asp Ile Tyr Ser Leu Ile Gln Leu Asn Leu Asp Lys Val Glu Glu
225                 230                 235                 240 ctt gat agc att gaa ttt gat ttc caa aag cct ttg act aaa tta aat      768
Leu Asp Ser Ile Glu Phe Asp Phe Gln Lys Pro Leu Thr Lys Leu Asn
                245                 250                 255 cta ctt gct gat aga tta tta act ctt tgt gag tat aga aag att aat      816
Leu Leu Ala Asp Arg Leu Leu Thr Leu Cys Glu Tyr Arg Lys Ile Asn
            260                 265                 270 aac ttt atc aga ttt gaa ttg cat gga aaa aaa tat ata tgt gaa agc      864
Asn Phe Ile Arg Phe Glu Leu His Gly Lys Lys Tyr Ile Cys Glu Ser
        275                 280                 285 ttt cct gaa gag ttt ttt gtt gct act aga tac tat ctt ttc ctt aaa      912
Phe Pro Glu Glu Phe Phe Val Ala Thr Arg Tyr Tyr Leu Phe Leu Lys
    290                 295                 300 agg aaa gca aca gct cca gcc aat gta agg ttt gaa aat aag aat gct      960
Arg Lys Ala Thr Ala Pro Ala Asn Val Arg Phe Glu Asn Lys Asn Ala
305                 310                 315                 320 ctg aga att act agt ata agt aga aat aag aat att gta gct ctg tct     1008
Leu Arg Ile Thr Ser Ile Ser Arg Asn Lys Asn Ile Val Ala Leu Ser
                325                 330                 335 ctt tca gga gta aaa ctg gtt gac gtt gaa tgt tct atg att aat ttt     1056
Leu Ser Gly Val Lys Leu Val Asp Val Glu Cys Ser Met Ile Asn Phe
            340                 345                 350 aca act aga ttt gat aat att gat gca ata tat gaa att caa aaa ggt     1104
Thr Thr Arg Phe Asp Asn Ile Asp Ala Ile Tyr Glu Ile Gln Lys Gly
        355                 360                 365 tct gag tgg gat ttt ata tta gcg gat agt agt gcg gtt ttt acg gct     1152
Ser Glu Trp Asp Phe Ile Leu Ala Asp Ser Ser Ala Val Phe Thr Ala
    370                 375                 380 ttt gaa ggt agt gag aat ttt gat ttc ttt ata gcc ttt tct taa         1197
Phe Glu Gly Ser Glu Asn Phe Asp Phe Phe Ile Ala Phe Ser
385                 390                 395

<210> SEQ ID NO 12
<211> LENGTH: 398
<212> TYPE: PRT
<213> ORGANISM: Francisella tularensis

<400> SEQUENCE: 12

Met Phe Leu Glu Arg Ile Tyr Trp Glu Asp Gly Leu Arg Leu Asp Ser
1               5                   10                  15

Asp Ile Leu Asp Lys Ser Asn Leu Ser Val Leu Glu Arg Leu Ser Thr
                20                  25                  30

Ala Ser Tyr Leu Pro Ala Asn Leu Asn Lys Gly Ile Val Ser Phe Asp
            35                  40                  45
```

Leu Asp Val Glu Ser Leu Gln Thr Gly Leu Ile Leu Ile Lys Asp Leu
 50                  55                  60

Lys Leu Tyr Leu Asp Glu Lys Asn Phe Val Phe Tyr Asp Lys Ser Tyr
 65                  70                  75                  80

Pro Leu Ser Leu Gln Ile Met Thr Asp Lys Leu Ser Asp Glu Ile Pro
                 85                  90                  95

Leu Phe Leu Asn Ile Arg Glu Lys Val Ile Glu Lys Asn Gly Ile Lys
            100                 105                 110

Tyr Ile Tyr Asn Gln Leu Ser Leu Ser Leu Glu His Ser Tyr Gly Phe
        115                 120                 125

Lys His Ser Ile Gln Ile Ala Leu Phe Arg Leu Asp Arg Gly Arg Leu
130                 135                 140

Val Pro Glu Ile Tyr Asp Phe Pro Leu Leu Thr Leu Asn His Tyr Tyr
145                 150                 155                 160

Leu Gly Asp Ile Phe Val Lys Leu Asn Arg Thr Val Ser Glu Leu Lys
                165                 170                 175

Ser Phe Asn Arg Phe Val Phe Ser Ala Ser Arg Ser Tyr Ala Ser Ile
            180                 185                 190

Leu Leu Val Phe Leu Ile Asn Lys Leu Glu Arg Glu Leu Lys Phe Ala
        195                 200                 205

Glu Ser Asn Arg Ala Asn Ser Ser Pro Lys Gln Ile Phe Asp Leu Ile
210                 215                 220

Asp Asp Ile Tyr Ser Leu Ile Gln Leu Asn Leu Asp Lys Val Glu Glu
225                 230                 235                 240

Leu Asp Ser Ile Glu Phe Asp Phe Gln Lys Pro Leu Thr Lys Leu Asn
                245                 250                 255

Leu Leu Ala Asp Arg Leu Leu Thr Leu Cys Glu Tyr Arg Lys Ile Asn
            260                 265                 270

Asn Phe Ile Arg Phe Glu Leu His Gly Lys Lys Tyr Ile Cys Glu Ser
        275                 280                 285

Phe Pro Glu Glu Phe Phe Val Ala Thr Arg Tyr Tyr Leu Phe Leu Lys
290                 295                 300

Arg Lys Ala Thr Ala Pro Ala Asn Val Arg Phe Glu Asn Lys Asn Ala
305                 310                 315                 320

Leu Arg Ile Thr Ser Ile Ser Arg Asn Lys Asn Ile Val Ala Leu Ser
                325                 330                 335

Leu Ser Gly Val Lys Leu Val Asp Val Glu Cys Ser Met Ile Asn Phe
            340                 345                 350

Thr Thr Arg Phe Asp Asn Ile Asp Ala Ile Tyr Glu Ile Gln Lys Gly
        355                 360                 365

Ser Glu Trp Asp Phe Ile Leu Ala Asp Ser Ser Ala Val Phe Thr Ala
370                 375                 380

Phe Glu Gly Ser Glu Asn Phe Asp Phe Phe Ile Ala Phe Ser
385                 390                 395

<210> SEQ ID NO 13
<211> LENGTH: 555
<212> TYPE: DNA
<213> ORGANISM: Francisella tularensis
<220> FEATURE:
<221> NAME/KEY: CDS
<222> LOCATION: (1)..(552)
<220> FEATURE:
<221> NAME/KEY: modified_res
<222> LOCATION: (117)
<223> OTHER INFORMATION: x = can be any naturally occurring amino acid

<400> SEQUENCE: 13

```
atg gca aaa aat aaa atc cca aat tca agg ttg atg ata aat tat gaa      48
Met Ala Lys Asn Lys Ile Pro Asn Ser Arg Leu Met Ile Asn Tyr Glu
1               5                  10                  15 act aat gtt gat ggt gtc tta aag aaa aaa gag cta cct tac aga gtc      96
Thr Asn Val Asp Gly Val Leu Lys Lys Lys Glu Leu Pro Tyr Arg Val
            20                  25                  30 cta gtt gtt ggc gat tta tca aaa gga aga tct gtg gat gca aaa aaa     144
Leu Val Val Gly Asp Leu Ser Lys Gly Arg Ser Val Asp Ala Lys Lys
        35                  40                  45 gag ttc gca gat aga gag gtc aga aga gta aat aat ggt gtt gat agg     192
Glu Phe Ala Asp Arg Glu Val Arg Arg Val Asn Asn Gly Val Asp Arg
 50                  55                  60 gtt tta gaa gag atg aat ata tct ttt gat ttt gag gca cca aac ttt     240
Val Leu Glu Glu Met Asn Ile Ser Phe Asp Phe Glu Ala Pro Asn Phe
65                  70                  75                  80 gtt tct aaa gat cct agt aat tta aaa gtt aat tat aga att gaa agt     288
Val Ser Lys Asp Pro Ser Asn Leu Lys Val Asn Tyr Arg Ile Glu Ser
                85                  90                  95 gtc aaa gat ttt aga cct gat gct gtt gct aaa aaa gtt cct gaa atc     336
Val Lys Asp Phe Arg Pro Asp Ala Val Ala Lys Lys Val Pro Glu Ile
            100                 105                 110 aga gcg ctg ctt gra atg aaa gag ata tta gca tcg ttt gct aag gac     384
Arg Ala Leu Leu Xaa Met Lys Glu Ile Leu Ala Ser Phe Ala Lys Asp
        115                 120                 125 att gaa aat aat cgt aat ctc aag aaa acc ata gat atg att ttt tca     432
Ile Glu Asn Asn Arg Asn Leu Lys Lys Thr Ile Asp Met Ile Phe Ser
130                 135                 140 gat agt aac gaa tta gaa tca tta aag agt aag att cct gct ttg aca     480
Asp Ser Asn Glu Leu Glu Ser Leu Lys Ser Lys Ile Pro Ala Leu Thr
145                 150                 155                 160 aat tat acg att aaa gac tct tgt gat gct gct gag tct caa gac tta     528
Asn Tyr Thr Ile Lys Asp Ser Cys Asp Ala Ala Glu Ser Gln Asp Leu
                165                 170                 175 agt aat caa caa gta gat gat aag tag                                 555
Ser Asn Gln Gln Val Asp Asp Lys
            180
```

<210> SEQ ID NO 14
<211> LENGTH: 184
<212> TYPE: PRT
<213> ORGANISM: Francisella tularensis
<220> FEATURE:
<221> NAME/KEY: misc_feature
<222> LOCATION: (117)..(117)
<223> OTHER INFORMATION: The 'Xaa' at location 117 stands for Gly, or Glu.

<400> SEQUENCE: 14

```
Met Ala Lys Asn Lys Ile Pro Asn Ser Arg Leu Met Ile Asn Tyr Glu
1               5                  10                  15

Thr Asn Val Asp Gly Val Leu Lys Lys Lys Glu Leu Pro Tyr Arg Val
            20                  25                  30

Leu Val Val Gly Asp Leu Ser Lys Gly Arg Ser Val Asp Ala Lys Lys
        35                  40                  45

Glu Phe Ala Asp Arg Glu Val Arg Arg Val Asn Asn Gly Val Asp Arg
 50                  55                  60

Val Leu Glu Glu Met Asn Ile Ser Phe Asp Phe Glu Ala Pro Asn Phe
65                  70                  75                  80

Val Ser Lys Asp Pro Ser Asn Leu Lys Val Asn Tyr Arg Ile Glu Ser
```

```
                     85                  90                  95
Val Lys Asp Phe Arg Pro Asp Ala Val Ala Lys Lys Val Pro Glu Ile
                100                 105                 110
Arg Ala Leu Leu Xaa Met Lys Glu Ile Leu Ala Ser Phe Ala Lys Asp
            115                 120                 125
Ile Glu Asn Asn Arg Asn Leu Lys Lys Thr Ile Asp Met Ile Phe Ser
130                 135                 140
Asp Ser Asn Glu Leu Glu Ser Leu Lys Ser Lys Ile Pro Ala Leu Thr
145                 150                 155                 160
Asn Tyr Thr Ile Lys Asp Ser Cys Asp Ala Ala Glu Ser Gln Asp Leu
                165                 170                 175
Ser Asn Gln Gln Val Asp Asp Lys
            180

<210> SEQ ID NO 15
<211> LENGTH: 591
<212> TYPE: DNA
<213> ORGANISM: Francisella tularensis
<220> FEATURE:
<221> NAME/KEY: CDS
<222> LOCATION: (1)..(588)

<400> SEQUENCE: 15 ttg ctt ata agg tgt tgt gaa aaa aag gac aat aag atg gca aaa aat      48
Met Leu Ile Arg Cys Cys Glu Lys Lys Asp Asn Lys Met Ala Lys Asn
1               5                  10                  15 aaa atc cca aat tca agg ttg atg ata aat tat gaa act aat gtt gat      96
Lys Ile Pro Asn Ser Arg Leu Met Ile Asn Tyr Glu Thr Asn Val Asp
            20                  25                  30 ggt gtc tta aag aaa aaa gag cta cct tac aga gtc cta gtt gtt ggc     144
Gly Val Leu Lys Lys Lys Glu Leu Pro Tyr Arg Val Leu Val Val Gly
        35                  40                  45 gat tta tca aaa gga aga tct gtg gat gca aaa aaa gag ttc gca gat     192
Asp Leu Ser Lys Gly Arg Ser Val Asp Ala Lys Lys Glu Phe Ala Asp
    50                  55                  60 aga gag gtc aga aga gta aat aat ggt gtt gat agg gtt tta gaa gag     240
Arg Glu Val Arg Arg Val Asn Asn Gly Val Asp Arg Val Leu Glu Glu
65                  70                  75                  80 atg aat ata tct ttt gat ttt gag gca cca aac ttt gtt tct aaa gat     288
Met Asn Ile Ser Phe Asp Phe Glu Ala Pro Asn Phe Val Ser Lys Asp
                85                  90                  95 cgt agt aat tta aaa gtt aat tat aga att gaa agt gtc aaa gat ttt     336
Arg Ser Asn Leu Lys Val Asn Tyr Arg Ile Glu Ser Val Lys Asp Phe
            100                 105                 110 aga cct gat gct gtt gct aaa aaa gtt cct gaa atc aga gcg ctg ctt     384
Arg Pro Asp Ala Val Ala Lys Lys Val Pro Glu Ile Arg Ala Leu Leu
        115                 120                 125 gaa atg aaa gag ata tta gca tcc ttt gct aag gac att gaa aat aat     432
Glu Met Lys Glu Ile Leu Ala Ser Phe Ala Lys Asp Ile Glu Asn Asn
    130                 135                 140 cgt aat ctc aag aaa acc ata gat atg att ttt tca gat agt aac gaa     480
Arg Asn Leu Lys Lys Thr Ile Asp Met Ile Phe Ser Asp Ser Asn Glu
145                 150                 155                 160 tta gaa tca tta aag agt aag att cct gct ttg aca aac tat acg att     528
Leu Glu Ser Leu Lys Ser Lys Ile Pro Ala Leu Thr Asn Tyr Thr Ile
                165                 170                 175 aaa gac tct tgt gat gct gct gag tct caa gac tta agt aat caa caa     576
Lys Asp Ser Cys Asp Ala Ala Glu Ser Gln Asp Leu Ser Asn Gln Gln
            180                 185                 190
```

```
gta gat ggt aag tag                                                591
Val Asp Gly Lys
        195

<210> SEQ ID NO 16
<211> LENGTH: 196
<212> TYPE: PRT
<213> ORGANISM: Francisella tularensis

<400> SEQUENCE: 16

Met Leu Ile Arg Cys Cys Glu Lys Lys Asp Asn Lys Met Ala Lys Asn
1               5                   10                  15

Lys Ile Pro Asn Ser Arg Leu Met Ile Asn Tyr Glu Thr Asn Val Asp
            20                  25                  30

Gly Val Leu Lys Lys Lys Glu Leu Pro Tyr Arg Val Leu Val Val Gly
        35                  40                  45

Asp Leu Ser Lys Gly Arg Ser Val Asp Ala Lys Lys Glu Phe Ala Asp
    50                  55                  60

Arg Glu Val Arg Arg Val Asn Asn Gly Val Asp Arg Val Leu Glu Glu
65                  70                  75                  80

Met Asn Ile Ser Phe Asp Phe Glu Ala Pro Asn Phe Val Ser Lys Asp
                85                  90                  95

Arg Ser Asn Leu Lys Val Asn Tyr Arg Ile Glu Ser Val Lys Asp Phe
            100                 105                 110

Arg Pro Asp Ala Val Ala Lys Lys Val Pro Glu Ile Arg Ala Leu Leu
        115                 120                 125

Glu Met Lys Glu Ile Leu Ala Ser Phe Ala Lys Asp Ile Glu Asn Asn
    130                 135                 140

Arg Asn Leu Lys Lys Thr Ile Asp Met Ile Phe Ser Asp Ser Asn Glu
145                 150                 155                 160

Leu Glu Ser Leu Lys Ser Lys Ile Pro Ala Leu Thr Asn Tyr Thr Ile
                165                 170                 175

Lys Asp Ser Cys Asp Ala Ala Glu Ser Gln Asp Leu Ser Asn Gln Gln
            180                 185                 190

Val Asp Gly Lys
        195

<210> SEQ ID NO 17
<211> LENGTH: 555
<212> TYPE: DNA
<213> ORGANISM: Francisella tularensis
<220> FEATURE:
<221> NAME/KEY: CDS
<222> LOCATION: (1)..(552)

<400> SEQUENCE: 17 atg gca aaa aat aaa atc cca aat tca agg ttg atg ata aat tat gaa       48
Met Ala Lys Asn Lys Ile Pro Asn Ser Arg Leu Met Ile Asn Tyr Glu
1               5                   10                  15 act aat gtt gat ggt gtc tta aag aaa aaa gag cta cct tac aga gtc       96
Thr Asn Val Asp Gly Val Leu Lys Lys Lys Glu Leu Pro Tyr Arg Val
            20                  25                  30 cta gtt gtt ggc gat tta tca aaa gga aga tct gtg gat gca aaa aaa      144
Leu Val Val Gly Asp Leu Ser Lys Gly Arg Ser Val Asp Ala Lys Lys
        35                  40                  45 gag ttc gca tat aga gag gtc aga aga gta aat aat ggt gtt gat agg      192
Glu Phe Ala Tyr Arg Glu Val Arg Arg Val Asn Asn Gly Val Asp Arg
    50                  55                  60 gtt tta gaa gag atg aat ata tct ttt gat ttt gag gca cca aac ttt      240
```

```
                                                                                288
gtt tct aaa gat cct agt aat tta aaa gtt aat tat aga att gaa agt
Val Ser Lys Asp Pro Ser Asn Leu Lys Val Asn Tyr Arg Ile Glu Ser
             85                  90                  95

336
gtc aaa gat ttt aga cct gat gct gtt gct aaa aaa gtt cct gaa atc
Val Lys Asp Phe Arg Pro Asp Ala Val Ala Lys Lys Val Pro Glu Ile
            100                 105                 110

384
aga gcg ctg ctt gaa atg aaa gag ata tta gca tcc ttt gct aag gac
Arg Ala Leu Leu Glu Met Lys Glu Ile Leu Ala Ser Phe Ala Lys Asp
        115                 120                 125

432
att gaa aat aat cgt aat ctc aag aaa acc ata gat atg att ttt tca
Ile Glu Asn Asn Arg Asn Leu Lys Lys Thr Ile Asp Met Ile Phe Ser
    130                 135                 140

480
gat agt aac gaa tta gaa tca tta aag agt aag att cct gct ttg aca
Asp Ser Asn Glu Leu Glu Ser Leu Lys Ser Lys Ile Pro Ala Leu Thr
145                 150                 155                 160

528
aat tat acg att aaa gac tct tgt gat gct gct ggg tct caa gac tta
Asn Tyr Thr Ile Lys Asp Ser Cys Asp Ala Ala Gly Ser Gln Asp Leu
                165                 170                 175

555
agt aat caa caa gta gat ggt aag tag
Ser Asn Gln Gln Val Asp Gly Lys
            180

<210> SEQ ID NO 18
<211> LENGTH: 184
<212> TYPE: PRT
<213> ORGANISM: Francisella tularensis

<400> SEQUENCE: 18

Met Ala Lys Asn Lys Ile Pro Asn Ser Arg Leu Met Ile Asn Tyr Glu
1               5                   10                  15

Thr Asn Val Asp Gly Val Leu Lys Lys Lys Glu Leu Pro Tyr Arg Val
            20                  25                  30

Leu Val Val Gly Asp Leu Ser Lys Gly Arg Ser Val Asp Ala Lys Lys
        35                  40                  45

Glu Phe Ala Tyr Arg Glu Val Arg Arg Val Asn Asn Gly Val Asp Arg
    50                  55                  60

Val Leu Glu Glu Met Asn Ile Ser Phe Asp Phe Glu Ala Pro Asn Phe
65                  70                  75                  80

Val Ser Lys Asp Pro Ser Asn Leu Lys Val Asn Tyr Arg Ile Glu Ser
                85                  90                  95

Val Lys Asp Phe Arg Pro Asp Ala Val Ala Lys Lys Val Pro Glu Ile
            100                 105                 110

Arg Ala Leu Leu Glu Met Lys Glu Ile Leu Ala Ser Phe Ala Lys Asp
        115                 120                 125

Ile Glu Asn Asn Arg Asn Leu Lys Lys Thr Ile Asp Met Ile Phe Ser
    130                 135                 140

Asp Ser Asn Glu Leu Glu Ser Leu Lys Ser Lys Ile Pro Ala Leu Thr
145                 150                 155                 160

Asn Tyr Thr Ile Lys Asp Ser Cys Asp Ala Ala Gly Ser Gln Asp Leu
                165                 170                 175

Ser Asn Gln Gln Val Asp Gly Lys
            180

<210> SEQ ID NO 19
<211> LENGTH: 1545
<212> TYPE: DNA
```

<213> ORGANISM: Francisella tularensis
<220> FEATURE:
<221> NAME/KEY: CDS
<222> LOCATION: (1)..(1542)

<400> SEQUENCE: 19

```
atg ata agt aga gag gat ttt gtt atg aca ata aat aaa tta agt ctc        48
Met Ile Ser Arg Glu Asp Phe Val Met Thr Ile Asn Lys Leu Ser Leu
1               5                   10                  15 act gat gaa ctt tta aat aat ttt ggg gga tct aca gaa gtt gat agt        96
Thr Asp Glu Leu Leu Asn Asn Phe Gly Gly Ser Thr Glu Val Asp Ser
            20                  25                  30 gta ctc aaa aat ata gat ttt gat gtt tca gat gat gct tct aaa gtt       144
Val Leu Lys Asn Ile Asp Phe Asp Val Ser Asp Asp Ala Ser Lys Val
        35                  40                  45 tta tct tta tct act gac tac aat gct aga aac ctt atg gcg cta tct       192
Leu Ser Leu Ser Thr Asp Tyr Asn Ala Arg Asn Leu Met Ala Leu Ser
    50                  55                  60 ttg gta tta gca aat aat gat aat ata aat aat tac aat caa aaa tat       240
Leu Val Leu Ala Asn Asn Asp Asn Ile Asn Asn Tyr Asn Gln Lys Tyr
65                  70                  75                  80 att caa aaa gtt att aca gtt att gat aag ctg att gat tta caa gtt       288
Ile Gln Lys Val Ile Thr Val Ile Asp Lys Leu Ile Asp Leu Gln Val
                85                  90                  95 aac tct att ata tct aat gat gag ttt aga gca ctt gag caa gaa tgg       336
Asn Ser Ile Ile Ser Asn Asp Glu Phe Arg Ala Leu Glu Gln Glu Trp
            100                 105                 110 cta aag gtg caa gag gtt tgt caa gaa gac tat gat aat gtt gaa gta       384
Leu Lys Val Gln Glu Val Cys Gln Glu Asp Tyr Asp Asn Val Glu Val
        115                 120                 125 agt ata tta gat gta aaa aaa gaa gag cta caa tat gat ttc gag aga       432
Ser Ile Leu Asp Val Lys Lys Glu Glu Leu Gln Tyr Asp Phe Glu Arg
    130                 135                 140 aat tta tat gat ata tct agt agt gac ttt ttc aaa aaa gta tat gtt       480
Asn Leu Tyr Asp Ile Ser Ser Ser Asp Phe Phe Lys Lys Val Tyr Val
145                 150                 155                 160 tca gaa ttt gat caa tat ggt ggc gaa cct tat ggc gca ata tta gga       528
Ser Glu Phe Asp Gln Tyr Gly Gly Glu Pro Tyr Gly Ala Ile Leu Gly
                165                 170                 175 ttg tat aat ttt gaa aat acc aca aat gat ata att tgg ttg act gga       576
Leu Tyr Asn Phe Glu Asn Thr Thr Asn Asp Ile Ile Trp Leu Thr Gly
            180                 185                 190 atg ggt atg gtg gca aag aat tct cat gca cca ttt att gca tca att       624
Met Gly Met Val Ala Lys Asn Ser His Ala Pro Phe Ile Ala Ser Ile
        195                 200                 205 gat aag tca ttc ttt ggt gtt aag gat tta tca gaa atc act cat ata       672
Asp Lys Ser Phe Phe Gly Val Lys Asp Leu Ser Glu Ile Thr His Ile
    210                 215                 220 aaa agt ttt gaa gct ttg ctt gag cat cct aga tat aaa gag tgg aat       720
Lys Ser Phe Glu Ala Leu Leu Glu His Pro Arg Tyr Lys Glu Trp Asn
225                 230                 235                 240 gat ttt aga aac ctt gat gtt gct gca tat ata ggt ttg acc gta ggt       768
Asp Phe Arg Asn Leu Asp Val Ala Ala Tyr Ile Gly Leu Thr Val Gly
                245                 250                 255 gat ttt atg ttg cgg caa cca tat aat cct gag aat aat cca gtt cag       816
Asp Phe Met Leu Arg Gln Pro Tyr Asn Pro Glu Asn Asn Pro Val Gln
            260                 265                 270 tat aaa ctt atg gaa ggc ttt aat gag ttt gtt gat tat gat aag aat       864
Tyr Lys Leu Met Glu Gly Phe Asn Glu Phe Val Asp Tyr Asp Lys Asn
        275                 280                 285
```

| | | |
|---|---|---|
| gaa agt tat cta tgg gga cct gct tca att cat cta gtt aag aat atg<br>Glu Ser Tyr Leu Trp Gly Pro Ala Ser Ile His Leu Val Lys Asn Met<br>290                         295                            300 | 912 |
| atg aga tct tat gat aaa act aga tgg ttc caa tat ata aga gga gtt<br>Met Arg Ser Tyr Asp Lys Thr Arg Trp Phe Gln Tyr Ile Arg Gly Val<br>305                    310                   315                 320 | 960 |
| gag agt ggt ggt tat gta aaa aac ttg gta gct tgc gta tat gat aat<br>Glu Ser Gly Gly Tyr Val Lys Asn Leu Val Ala Cys Val Tyr Asp Asn<br>                     325                   330                   335 | 1008 |
| aaa ggc att cta gaa act aag tca cct cta aat gta tta ttt gct gat<br>Lys Gly Ile Leu Glu Thr Lys Ser Pro Leu Asn Val Leu Phe Ala Asp<br>340                         345                            350 | 1056 |
| tat atg gag tta tca ctt gca aat att ggt tta ata cca ttt gta agt<br>Tyr Met Glu Leu Ser Leu Ala Asn Ile Gly Leu Ile Pro Phe Val Ser<br>               355                   360                   365 | 1104 |
| gaa aaa ggt act agt aac gct tgt ttc ttt agt gta aat tct gct aaa<br>Glu Lys Gly Thr Ser Asn Ala Cys Phe Phe Ser Val Asn Ser Ala Lys<br>370                         375                            380 | 1152 |
| aaa gtc gaa gaa ttt gta gat gga ttt gac tca gca aac tca aga tta<br>Lys Val Glu Glu Phe Val Asp Gly Phe Asp Ser Ala Asn Ser Arg Leu<br>385                    390                   395                 400 | 1200 |
| att gct aac ctt tct tac act atg tgt ata tcg aga ata tct cat tat<br>Ile Ala Asn Leu Ser Tyr Thr Met Cys Ile Ser Arg Ile Ser His Tyr<br>                           405                   410                   415 | 1248 |
| att aaa tgt gta att aga gat aag att ggt agt att gtg gat gtc gag<br>Ile Lys Cys Val Ile Arg Asp Lys Ile Gly Ser Ile Val Asp Val Glu<br>                     420                   425                   430 | 1296 |
| tcg att caa aaa att ctt tct gat tgg ata tca gaa ttt gtc acc aca<br>Ser Ile Gln Lys Ile Leu Ser Asp Trp Ile Ser Glu Phe Val Thr Thr<br>               435                   440                   445 | 1344 |
| gtc tat caa cca acc cct tta gaa atg gcg aga tat cct ttc aga aac<br>Val Tyr Gln Pro Thr Pro Leu Glu Met Ala Arg Tyr Pro Phe Arg Asn<br>450                         455                            460 | 1392 |
| gtt tct atc gag gtt aaa acc ata ccg ggt aag cct ggc tgg tat tca<br>Val Ser Ile Glu Val Lys Thr Ile Pro Gly Lys Pro Gly Trp Tyr Ser<br>465                    470                   475                 480 | 1440 |
| tgc aaa ata aat gta att ccc cac att caa ttt gaa gga atg aat act<br>Cys Lys Ile Asn Val Ile Pro His Ile Gln Phe Glu Gly Met Asn Thr<br>                         485                   490                   495 | 1488 |
| aca atg act ata gat act agg ctt gaa cca gaa tta ttc ggt aca aat<br>Thr Met Thr Ile Asp Thr Arg Leu Glu Pro Glu Leu Phe Gly Thr Asn<br>                     500                         505                   510 | 1536 |
| aat aac taa<br>Asn Asn | 1545 |

```
<210> SEQ ID NO 20
<211> LENGTH: 514
<212> TYPE: PRT
<213> ORGANISM: Francisella tularensis

<400> SEQUENCE: 20
```

Met Ile Ser Arg Glu Asp Phe Val Met Thr Ile Asn Lys Leu Ser Leu
1                5                    10                   15

Thr Asp Glu Leu Leu Asn Asn Phe Gly Gly Ser Thr Glu Val Asp Ser
              20                    25                    30

Val Leu Lys Asn Ile Asp Phe Asp Val Ser Asp Ala Ser Lys Val
                 35                    40                    45

Leu Ser Leu Ser Thr Asp Tyr Asn Ala Arg Asn Leu Met Ala Leu Ser
              50                    55                    60

-continued

```
Leu Val Leu Ala Asn Asn Asp Asn Ile Asn Asn Tyr Asn Gln Lys Tyr
 65                  70                  75                  80

Ile Gln Lys Val Ile Thr Val Ile Asp Lys Leu Ile Asp Leu Gln Val
             85                  90                  95

Asn Ser Ile Ile Ser Asn Asp Glu Phe Arg Ala Leu Glu Gln Glu Trp
             100                 105                 110

Leu Lys Val Gln Glu Val Cys Gln Glu Asp Tyr Asp Asn Val Glu Val
             115                 120                 125

Ser Ile Leu Asp Val Lys Lys Glu Glu Leu Gln Tyr Asp Phe Glu Arg
     130                 135                 140

Asn Leu Tyr Asp Ile Ser Ser Asp Phe Lys Lys Val Tyr Val
145                 150                 155                 160

Ser Glu Phe Asp Gln Tyr Gly Gly Glu Pro Tyr Gly Ala Ile Leu Gly
             165                 170                 175

Leu Tyr Asn Phe Glu Asn Thr Thr Asn Asp Ile Ile Trp Leu Thr Gly
             180                 185                 190

Met Gly Met Val Ala Lys Asn Ser His Ala Pro Phe Ile Ala Ser Ile
     195                 200                 205

Asp Lys Ser Phe Phe Gly Val Lys Asp Leu Ser Glu Ile Thr His Ile
     210                 215                 220

Lys Ser Phe Glu Ala Leu Leu Glu His Pro Arg Tyr Lys Glu Trp Asn
225                 230                 235                 240

Asp Phe Arg Asn Leu Asp Val Ala Ala Tyr Ile Gly Leu Thr Val Gly
                 245                 250                 255

Asp Phe Met Leu Arg Gln Pro Tyr Asn Pro Glu Asn Asn Pro Val Gln
             260                 265                 270

Tyr Lys Leu Met Glu Gly Phe Asn Glu Phe Val Asp Tyr Asp Lys Asn
         275                 280                 285

Glu Ser Tyr Leu Trp Gly Pro Ala Ser Ile His Leu Val Lys Asn Met
     290                 295                 300

Met Arg Ser Tyr Asp Lys Thr Arg Trp Phe Gln Tyr Ile Arg Gly Val
305                 310                 315                 320

Glu Ser Gly Gly Tyr Val Lys Asn Leu Val Ala Cys Val Tyr Asp Asn
                 325                 330                 335

Lys Gly Ile Leu Glu Thr Lys Ser Pro Leu Asn Val Leu Phe Ala Asp
             340                 345                 350

Tyr Met Glu Leu Ser Leu Ala Asn Ile Gly Leu Ile Pro Phe Val Ser
         355                 360                 365

Glu Lys Gly Thr Ser Asn Ala Cys Phe Phe Ser Val Asn Ser Ala Lys
     370                 375                 380

Lys Val Glu Glu Phe Val Asp Gly Phe Asp Ser Ala Asn Ser Arg Leu
385                 390                 395                 400

Ile Ala Asn Leu Ser Tyr Thr Met Cys Ile Ser Arg Ile Ser His Tyr
                 405                 410                 415

Ile Lys Cys Val Ile Arg Asp Lys Ile Gly Ser Ile Val Asp Val Glu
             420                 425                 430

Ser Ile Gln Lys Ile Leu Ser Asp Trp Ile Ser Glu Phe Val Thr Thr
         435                 440                 445

Val Tyr Gln Pro Thr Pro Leu Glu Met Ala Arg Tyr Pro Phe Arg Asn
     450                 455                 460

Val Ser Ile Glu Val Lys Thr Ile Pro Gly Lys Pro Gly Trp Tyr Ser
465                 470                 475                 480

Cys Lys Ile Asn Val Ile Pro His Ile Gln Phe Glu Gly Met Asn Thr
```

```
                          485                 490                 495
Thr Met Thr Ile Asp Thr Arg Leu Glu Pro Glu Leu Phe Gly Thr Asn
        500                 505                 510

Asn Asn

<210> SEQ ID NO 21
<211> LENGTH: 1545
<212> TYPE: DNA
<213> ORGANISM: Francisella tularensis
<220> FEATURE:
<221> NAME/KEY: CDS
<222> LOCATION: (1)..(1542)

<400> SEQUENCE: 21 atg gta agt agg gag gat ttt att atg aca ata aat aaa tta agt ctc      48
Met Val Ser Arg Glu Asp Phe Ile Met Thr Ile Asn Lys Leu Ser Leu
1               5                   10                  15 act gat gaa ctt tta aat aat ttt ggg gga tct aca gaa gtt gat agt      96
Thr Asp Glu Leu Leu Asn Asn Phe Gly Gly Ser Thr Glu Val Asp Ser
            20                  25                  30 gta ctc aaa aat ata gat ttt gat gtt tca gat gat gct tct aaa gtt     144
Val Leu Lys Asn Ile Asp Phe Asp Val Ser Asp Asp Ala Ser Lys Val
        35                  40                  45 tta tct tta tct act gac tac aat gct aga aac ctt atg gcg cta tct     192
Leu Ser Leu Ser Thr Asp Tyr Asn Ala Arg Asn Leu Met Ala Leu Ser
    50                  55                  60 ttg gta tta gca aat aat gat aat ata aat aat tat aat caa aaa tat     240
Leu Val Leu Ala Asn Asn Asp Asn Ile Asn Asn Tyr Asn Gln Lys Tyr
65                  70                  75                  80 atc cag aaa gtt att aca gtt att gat aag ctt att gat tta caa gtt     288
Ile Gln Lys Val Ile Thr Val Ile Asp Lys Leu Ile Asp Leu Gln Val
                85                  90                  95 aat tct att ata tct aat gat gag ttt aga gca ctt gag caa gaa tgg     336
Asn Ser Ile Ile Ser Asn Asp Glu Phe Arg Ala Leu Glu Gln Glu Trp
            100                 105                 110 cta aag gtg caa gag gtt tgt caa gaa gac tat gat aat gtt gaa gta     384
Leu Lys Val Gln Glu Val Cys Gln Glu Asp Tyr Asp Asn Val Glu Val
        115                 120                 125 agt ata tta gat gta aaa aaa gaa gag cta caa tat gat ttc gag aga     432
Ser Ile Leu Asp Val Lys Lys Glu Glu Leu Gln Tyr Asp Phe Glu Arg
    130                 135                 140 aat tta tat gat ata tct agt agt gac ttt ttc aaa aaa gtt tac gtt     480
Asn Leu Tyr Asp Ile Ser Ser Ser Asp Phe Phe Lys Lys Val Tyr Val
145                 150                 155                 160 tca gaa ttt gat caa tat ggt ggc gaa cct tat ggc gca ata tta gga     528
Ser Glu Phe Asp Gln Tyr Gly Gly Glu Pro Tyr Gly Ala Ile Leu Gly
                165                 170                 175 ttg tat aat ttt gaa aat acc aca aat gat ata att tgg ttg act gga     576
Leu Tyr Asn Phe Glu Asn Thr Thr Asn Asp Ile Ile Trp Leu Thr Gly
            180                 185                 190 atg ggt atg gtg gca aag aat tct cat gca cca ttt att gca tca att     624
Met Gly Met Val Ala Lys Asn Ser His Ala Pro Phe Ile Ala Ser Ile
        195                 200                 205 gat aag tca ttc ttt ggt gtt aag gat tta tca gaa atc act cat ata     672
Asp Lys Ser Phe Phe Gly Val Lys Asp Leu Ser Glu Ile Thr His Ile
    210                 215                 220 aaa agt ttt gaa gct ttg ctt gag cat cct aga tat aaa gag tgg aat     720
Lys Ser Phe Glu Ala Leu Leu Glu His Pro Arg Tyr Lys Glu Trp Asn
225                 230                 235                 240 gat ttt aga aac ctt gat gtt gct gca tat ata ggt ttg acc gta ggt     768
```

| | | | | | | | | | | | | | | | |
|---|---|---|---|---|---|---|---|---|---|---|---|---|---|---|---|
|Asp|Phe|Arg|Asn|Leu|Asp|Val|Ala|Ala|Tyr|Ile|Gly|Leu|Thr|Val|Gly|
| | | |245| | | |250| | | | |255| | | |

```
gat ttt atg ttg cgg caa cca tat aat cct gag aat aat cca gtt cag      816
Asp Phe Met Leu Arg Gln Pro Tyr Asn Pro Glu Asn Asn Pro Val Gln
        260                 265                 270 tat aaa ctt atg gaa ggc ttt aat gag ttt gtt gat tat gat aag aat      864
Tyr Lys Leu Met Glu Gly Phe Asn Glu Phe Val Asp Tyr Asp Lys Asn
            275                 280                 285 gaa agt tat cta tgg gga cct gct tca att cat cta gtt aag aat atg      912
Glu Ser Tyr Leu Trp Gly Pro Ala Ser Ile His Leu Val Lys Asn Met
    290                 295                 300 atg aga tct tat gat aaa act aga tgg ttc caa tat ata aga gga gtt      960
Met Arg Ser Tyr Asp Lys Thr Arg Trp Phe Gln Tyr Ile Arg Gly Val
305                 310                 315                 320 gag agt ggt ggt tat gta aag aac ttg gta gct tgc gta tat gat aat     1008
Glu Ser Gly Gly Tyr Val Lys Asn Leu Val Ala Cys Val Tyr Asp Asn
                325                 330                 335 aaa ggc att cta gaa act aag tca cct tta aat gta tta ttc gct gat     1056
Lys Gly Ile Leu Glu Thr Lys Ser Pro Leu Asn Val Leu Phe Ala Asp
            340                 345                 350 tat atg gag tta tca ctt gca aat att ggt tta ata cca ttt gta agt     1104
Tyr Met Glu Leu Ser Leu Ala Asn Ile Gly Leu Ile Pro Phe Val Ser
    355                 360                 365 gaa aaa ggt act agt aac gct tgt ttc ttt agt gta aat tct gct aaa     1152
Glu Lys Gly Thr Ser Asn Ala Cys Phe Phe Ser Val Asn Ser Ala Lys
370                 375                 380 aaa gtc gaa gaa ttt gta gat gga ttt gac tca gca aac tca aga tta     1200
Lys Val Glu Glu Phe Val Asp Gly Phe Asp Ser Ala Asn Ser Arg Leu
385                 390                 395                 400 att gct aac ctt tct tac act atg tgt ata tcg aga ata tct cat tat     1248
Ile Ala Asn Leu Ser Tyr Thr Met Cys Ile Ser Arg Ile Ser His Tyr
                405                 410                 415 att aaa tgt gta att aga gat aag att ggt agt att gtg gat gtc gag     1296
Ile Lys Cys Val Ile Arg Asp Lys Ile Gly Ser Ile Val Asp Val Glu
            420                 425                 430 tcg att caa aaa att ctt tct gat tgg ata tca gaa ttt gtc acc aca     1344
Ser Ile Gln Lys Ile Leu Ser Asp Trp Ile Ser Glu Phe Val Thr Thr
    435                 440                 445 gtc tat caa cca acc cct tta gaa atg gcg aga tat cct ttc aga aac     1392
Val Tyr Gln Pro Thr Pro Leu Glu Met Ala Arg Tyr Pro Phe Arg Asn
450                 455                 460 gtt tct atc gag gtt gaa acc ata ccg ggt aag cct ggc tgg tat tca     1440
Val Ser Ile Glu Val Glu Thr Ile Pro Gly Lys Pro Gly Trp Tyr Ser
465                 470                 475                 480 tgc aaa ata aat gta att ccc cac att caa ttt gaa gga atg aat act     1488
Cys Lys Ile Asn Val Ile Pro His Ile Gln Phe Glu Gly Met Asn Thr
                485                 490                 495 aca atg act ata gat act agg ctt gaa cca gaa tta ttc ggt aca aat     1536
Thr Met Thr Ile Asp Thr Arg Leu Glu Pro Glu Leu Phe Gly Thr Asn
            500                 505                 510 aat aac taa                                                          1545
Asn Asn
```

<210> SEQ ID NO 22
<211> LENGTH: 514
<212> TYPE: PRT
<213> ORGANISM: Francisella tularensis

<400> SEQUENCE: 22

Met Val Ser Arg Glu Asp Phe Ile Met Thr Ile Asn Lys Leu Ser Leu

-continued

```
1               5                   10                  15

Thr Asp Glu Leu Leu Asn Asn Phe Gly Gly Ser Thr Glu Val Asp Ser
                20                  25                  30

Val Leu Lys Asn Ile Asp Phe Asp Val Ser Asp Ala Ser Lys Val
                35                  40                  45

Leu Ser Leu Ser Thr Asp Tyr Asn Ala Arg Asn Leu Met Ala Leu Ser
                50                  55                  60

Leu Val Leu Ala Asn Asn Asp Asn Ile Asn Asn Tyr Asn Gln Lys Tyr
 65                 70                  75                  80

Ile Gln Lys Val Ile Thr Val Ile Asp Lys Leu Ile Asp Leu Gln Val
                85                  90                  95

Asn Ser Ile Ile Ser Asn Asp Glu Phe Arg Ala Leu Glu Gln Glu Trp
                100                 105                 110

Leu Lys Val Gln Glu Val Cys Gln Glu Asp Tyr Asp Asn Val Glu Val
                115                 120                 125

Ser Ile Leu Asp Val Lys Lys Glu Glu Leu Gln Tyr Asp Phe Glu Arg
                130                 135                 140

Asn Leu Tyr Asp Ile Ser Ser Ser Asp Phe Phe Lys Lys Val Tyr Val
145                 150                 155                 160

Ser Glu Phe Asp Gln Tyr Gly Gly Glu Pro Tyr Gly Ala Ile Leu Gly
                165                 170                 175

Leu Tyr Asn Phe Glu Asn Thr Thr Asn Asp Ile Ile Trp Leu Thr Gly
                180                 185                 190

Met Gly Met Val Ala Lys Asn Ser His Ala Pro Phe Ile Ala Ser Ile
                195                 200                 205

Asp Lys Ser Phe Phe Gly Val Lys Asp Leu Ser Glu Ile Thr His Ile
                210                 215                 220

Lys Ser Phe Glu Ala Leu Leu Glu His Pro Arg Tyr Lys Glu Trp Asn
225                 230                 235                 240

Asp Phe Arg Asn Leu Asp Val Ala Ala Tyr Ile Gly Leu Thr Val Gly
                245                 250                 255

Asp Phe Met Leu Arg Gln Pro Tyr Asn Pro Glu Asn Asn Pro Val Gln
                260                 265                 270

Tyr Lys Leu Met Glu Gly Phe Asn Glu Phe Val Asp Tyr Asp Lys Asn
                275                 280                 285

Glu Ser Tyr Leu Trp Gly Pro Ala Ser Ile His Leu Val Lys Asn Met
                290                 295                 300

Met Arg Ser Tyr Asp Lys Thr Arg Trp Phe Gln Tyr Ile Arg Gly Val
305                 310                 315                 320

Glu Ser Gly Gly Tyr Val Lys Asn Leu Val Ala Cys Val Tyr Asp Asn
                325                 330                 335

Lys Gly Ile Leu Glu Thr Lys Ser Pro Leu Asn Val Leu Phe Ala Asp
                340                 345                 350

Tyr Met Glu Leu Ser Leu Ala Asn Ile Gly Leu Ile Pro Phe Val Ser
                355                 360                 365

Glu Lys Gly Thr Ser Asn Ala Cys Phe Phe Ser Val Asn Ser Ala Lys
                370                 375                 380

Lys Val Glu Glu Phe Val Asp Gly Phe Asp Ser Ala Asn Ser Arg Leu
385                 390                 395                 400

Ile Ala Asn Leu Ser Tyr Thr Met Cys Ile Ser Arg Ile Ser His Tyr
                405                 410                 415

Ile Lys Cys Val Ile Arg Asp Lys Ile Gly Ser Ile Val Asp Val Glu
                420                 425                 430
```

```
Ser Ile Gln Lys Ile Leu Ser Asp Trp Ile Ser Glu Phe Val Thr Thr
            435                 440                 445

Val Tyr Gln Pro Thr Pro Leu Glu Met Ala Arg Tyr Pro Phe Arg Asn
    450                 455                 460

Val Ser Ile Glu Val Glu Thr Ile Pro Gly Lys Pro Gly Trp Tyr Ser
465                 470                 475                 480

Cys Lys Ile Asn Val Ile Pro His Ile Gln Phe Glu Gly Met Asn Thr
                485                 490                 495

Thr Met Thr Ile Asp Thr Arg Leu Glu Pro Glu Leu Phe Gly Thr Asn
            500                 505                 510

Asn Asn

<210> SEQ ID NO 23
<211> LENGTH: 1521
<212> TYPE: DNA
<213> ORGANISM: Francisella tularensis
<220> FEATURE:
<221> NAME/KEY: CDS
<222> LOCATION: (1)..(1518)

<400> SEQUENCE: 23 atg aca ata aat aaa tta agt ctc act gat gaa ctt tta aat aat ttt      48
Met Thr Ile Asn Lys Leu Ser Leu Thr Asp Glu Leu Leu Asn Asn Phe
1               5                   10                  15 ggg gga tct aca gaa gtt gat agt gta ctc aaa aat ata gat ttt gat      96
Gly Gly Ser Thr Glu Val Asp Ser Val Leu Lys Asn Ile Asp Phe Asp
                20                  25                  30 gtt tca gat gat gct tct aaa gtt tta tct tta tct act gac tac aat     144
Val Ser Asp Asp Ala Ser Lys Val Leu Ser Leu Ser Thr Asp Tyr Asn
            35                  40                  45 gct aga aac ctt atg gcg cta tct ttg gta tta gca aat aat gat aat     192
Ala Arg Asn Leu Met Ala Leu Ser Leu Val Leu Ala Asn Asn Asp Asn
        50                  55                  60 ata aat aat tat aat caa aaa tat atc cag aaa gtt att aca gtt att     240
Ile Asn Asn Tyr Asn Gln Lys Tyr Ile Gln Lys Val Ile Thr Val Ile
65                  70                  75                  80 gat agg ctt att gat tta caa gtt aat tct att ata tct aat gat gag     288
Asp Arg Leu Ile Asp Leu Gln Val Asn Ser Ile Ile Ser Asn Asp Glu
                85                  90                  95 ttt aga gca ctt gag caa gaa tgg cta aag gtg caa gag gtt tgt caa     336
Phe Arg Ala Leu Glu Gln Glu Trp Leu Lys Val Gln Glu Val Cys Gln
                100                 105                 110 gaa gac tat gat aat gtt gaa gta agt ata tta gat gta aaa aaa gaa     384
Glu Asp Tyr Asp Asn Val Glu Val Ser Ile Leu Asp Val Lys Lys Glu
            115                 120                 125 gag cta caa tat gat ttc gag aga aat tta tat gat ata tct agt agt     432
Glu Leu Gln Tyr Asp Phe Glu Arg Asn Leu Tyr Asp Ile Ser Ser Ser
        130                 135                 140 gac ttt ttc aaa aaa gtt tac gtt tca gaa ttt gat caa tat ggt gga     480
Asp Phe Phe Lys Lys Val Tyr Val Ser Glu Phe Asp Gln Tyr Gly Gly
145                 150                 155                 160 gaa cct tat ggc gca ata tta gga ttg tat aat ttt gaa aat acc aca     528
Glu Pro Tyr Gly Ala Ile Leu Gly Leu Tyr Asn Phe Glu Asn Thr Thr
                165                 170                 175 aat gat ata att tgg ttg act gga atg ggt atg gtg gca aag aat tct     576
Asn Asp Ile Ile Trp Leu Thr Gly Met Gly Met Val Ala Lys Asn Ser
            180                 185                 190 cat gca cca ttt att gca tca att gat aag tca ttc ttt ggt gtt aag     624
His Ala Pro Phe Ile Ala Ser Ile Asp Lys Ser Phe Phe Gly Val Lys
```

-continued

```
                  195                 200                 205
gat tta tca gaa atc act cat ata aaa agt ttt gaa gct ttg ctt gag         672
Asp Leu Ser Glu Ile Thr His Ile Lys Ser Phe Glu Ala Leu Leu Glu
    210                 215                 220 cat cct aga tat aaa gag tgg aat gat ttt aga aac ctt gat gtt gct         720
His Pro Arg Tyr Lys Glu Trp Asn Asp Phe Arg Asn Leu Asp Val Ala
225                 230                 235                 240 gca tat ata ggt ttg acc gta ggt gat ttt atg ttg cgg caa cca tat         768
Ala Tyr Ile Gly Leu Thr Val Gly Asp Phe Met Leu Arg Gln Pro Tyr
                245                 250                 255 aat cct gag aat aat cca gtt cag tat aaa ctt atg gaa ggc ttt aat         816
Asn Pro Glu Asn Asn Pro Val Gln Tyr Lys Leu Met Glu Gly Phe Asn
            260                 265                 270 gag ttt gtt gat tat gat aag aat gaa agt tat cta tgg gga cct gct         864
Glu Phe Val Asp Tyr Asp Lys Asn Glu Ser Tyr Leu Trp Gly Pro Ala
        275                 280                 285 tca att cat cta gtt aag aat atg atg aga tct tat gat aaa act aga         912
Ser Ile His Leu Val Lys Asn Met Met Arg Ser Tyr Asp Lys Thr Arg
    290                 295                 300 tgg ttc caa tat ata aga gga gtt gag agt ggt ggt tat gta aag aac         960
Trp Phe Gln Tyr Ile Arg Gly Val Glu Ser Gly Gly Tyr Val Lys Asn
305                 310                 315                 320 ttg gta gct tgc gta tat gat aat aaa ggc att cta gaa act aag tca        1008
Leu Val Ala Cys Val Tyr Asp Asn Lys Gly Ile Leu Glu Thr Lys Ser
                325                 330                 335 cct tta aat gta tta ttt gct gat tat atg gag tta tca ctt gca aat        1056
Pro Leu Asn Val Leu Phe Ala Asp Tyr Met Glu Leu Ser Leu Ala Asn
            340                 345                 350 att ggt tta ata cca ttt gta agt gaa aaa ggt act agt aat gct tgt        1104
Ile Gly Leu Ile Pro Phe Val Ser Glu Lys Gly Thr Ser Asn Ala Cys
        355                 360                 365 ttt ttt agt gta aat tct gct aaa aaa gtc gaa gaa ttt gta gat gga        1152
Phe Phe Ser Val Asn Ser Ala Lys Lys Val Glu Glu Phe Val Asp Gly
    370                 375                 380 ttt gac tca gca aac tca aga tta att gct aac ctt tct tac act atg        1200
Phe Asp Ser Ala Asn Ser Arg Leu Ile Ala Asn Leu Ser Tyr Thr Met
385                 390                 395                 400 tgt ata tcg aga ata tct cat tat att aaa tgt gta att aga gat aag        1248
Cys Ile Ser Arg Ile Ser His Tyr Ile Lys Cys Val Ile Arg Asp Lys
                405                 410                 415 att ggt agt att gtg gat gtc gag tcg att caa aaa att ctt tct gat        1296
Ile Gly Ser Ile Val Asp Val Glu Ser Ile Gln Lys Ile Leu Ser Asp
            420                 425                 430 tgg ata tca gaa ttt gtc acc aca gtc tat caa cca acc cct tta gaa        1344
Trp Ile Ser Glu Phe Val Thr Thr Val Tyr Gln Pro Thr Pro Leu Glu
        435                 440                 445 atg gcg aga tat cct ttc aga aac gtt tct atc gag gtt aaa acc ata        1392
Met Ala Arg Tyr Pro Phe Arg Asn Val Ser Ile Glu Val Lys Thr Ile
    450                 455                 460 ccg ggt aag cct ggc tgg tat tca tgc aaa ata aat gta att ccc cac        1440
Pro Gly Lys Pro Gly Trp Tyr Ser Cys Lys Ile Asn Val Ile Pro His
465                 470                 475                 480 att caa ttt gaa gga atg aat act aca atg act ata gat act agg ctt        1488
Ile Gln Phe Glu Gly Met Asn Thr Thr Met Thr Ile Asp Thr Arg Leu
                485                 490                 495 gaa cca gaa tta ttc ggt aca aat aat aac taa                            1521
Glu Pro Glu Leu Phe Gly Thr Asn Asn Asn
            500                 505
```

<210> SEQ ID NO 24
<211> LENGTH: 506
<212> TYPE: PRT
<213> ORGANISM: Francisella tularensis

<400> SEQUENCE: 24

Met Thr Ile Asn Lys Leu Ser Leu Thr Asp Glu Leu Leu Asn Asn Phe
1               5                   10                  15

Gly Gly Ser Thr Glu Val Asp Ser Val Leu Lys Asn Ile Asp Phe Asp
            20                  25                  30

Val Ser Asp Ala Ser Lys Val Leu Ser Leu Ser Thr Asp Tyr Asn
        35                  40                  45

Ala Arg Asn Leu Met Ala Leu Ser Leu Val Leu Ala Asn Asn Asp Asn
    50                  55                  60

Ile Asn Asn Tyr Asn Gln Lys Tyr Ile Gln Lys Val Ile Thr Val Ile
65                  70                  75                  80

Asp Arg Leu Ile Asp Leu Gln Val Asn Ser Ile Ile Ser Asn Asp Glu
                85                  90                  95

Phe Arg Ala Leu Glu Gln Glu Trp Leu Lys Val Gln Glu Val Cys Gln
            100                 105                 110

Glu Asp Tyr Asp Asn Val Glu Val Ser Ile Leu Asp Val Lys Lys Glu
        115                 120                 125

Glu Leu Gln Tyr Asp Phe Glu Arg Asn Leu Tyr Asp Ile Ser Ser Ser
    130                 135                 140

Asp Phe Phe Lys Lys Val Tyr Val Ser Glu Phe Asp Gln Tyr Gly Gly
145                 150                 155                 160

Glu Pro Tyr Gly Ala Ile Leu Gly Leu Tyr Asn Phe Glu Asn Thr Thr
                165                 170                 175

Asn Asp Ile Ile Trp Leu Thr Gly Met Gly Met Val Ala Lys Asn Ser
            180                 185                 190

His Ala Pro Phe Ile Ala Ser Ile Asp Lys Ser Phe Phe Gly Val Lys
        195                 200                 205

Asp Leu Ser Glu Ile Thr His Ile Lys Ser Phe Glu Ala Leu Leu Glu
    210                 215                 220

His Pro Arg Tyr Lys Glu Trp Asn Asp Phe Arg Asn Leu Asp Val Ala
225                 230                 235                 240

Ala Tyr Ile Gly Leu Thr Val Gly Asp Phe Met Leu Arg Gln Pro Tyr
                245                 250                 255

Asn Pro Glu Asn Asn Pro Val Gln Tyr Lys Leu Met Glu Gly Phe Asn
            260                 265                 270

Glu Phe Val Asp Tyr Asp Lys Asn Glu Ser Tyr Leu Trp Gly Pro Ala
        275                 280                 285

Ser Ile His Leu Val Lys Asn Met Met Arg Ser Tyr Asp Lys Thr Arg
    290                 295                 300

Trp Phe Gln Tyr Ile Arg Gly Val Glu Ser Gly Tyr Val Lys Asn
305                 310                 315                 320

Leu Val Ala Cys Val Tyr Asp Asn Lys Gly Ile Leu Glu Thr Lys Ser
                325                 330                 335

Pro Leu Asn Val Leu Phe Ala Asp Tyr Met Glu Leu Ser Leu Ala Asn
            340                 345                 350

Ile Gly Leu Ile Pro Phe Val Ser Glu Lys Gly Thr Ser Asn Ala Cys
        355                 360                 365

Phe Phe Ser Val Asn Ser Ala Lys Lys Val Glu Glu Phe Val Asp Gly
    370                 375                 380

```
Phe Asp Ser Ala Asn Ser Arg Leu Ile Ala Asn Leu Ser Tyr Thr Met
385                 390                 395                 400

Cys Ile Ser Arg Ile Ser His Tyr Ile Lys Cys Val Ile Arg Asp Lys
            405                 410                 415

Ile Gly Ser Ile Val Asp Val Glu Ser Ile Gln Lys Ile Leu Ser Asp
            420                 425                 430

Trp Ile Ser Glu Phe Val Thr Thr Val Tyr Gln Pro Thr Pro Leu Glu
            435                 440                 445

Met Ala Arg Tyr Pro Phe Arg Asn Val Ser Ile Glu Val Lys Thr Ile
450                 455                 460

Pro Gly Lys Pro Gly Trp Tyr Ser Cys Lys Ile Asn Val Ile Pro His
465                 470                 475                 480

Ile Gln Phe Glu Gly Met Asn Thr Thr Met Thr Ile Asp Thr Arg Leu
                485                 490                 495

Glu Pro Glu Leu Phe Gly Thr Asn Asn Asn
                500                 505

<210> SEQ ID NO 25
<211> LENGTH: 618
<212> TYPE: DNA
<213> ORGANISM: Francisella tularensis
<220> FEATURE:
<221> NAME/KEY: CDS
<222> LOCATION: (1)..(618)

<400> SEQUENCE: 25 ttg ctt tta tac aca aaa aaa gat gat atc tat agc gat ata gtc cgc      48
Met Leu Leu Tyr Thr Lys Lys Asp Asp Ile Tyr Ser Asp Ile Val Arg
1               5                   10                  15 atg atc ctt ctt att aaa ggg gct aat gcg aaa att gta gat gtt tct      96
Met Ile Leu Leu Ile Lys Gly Ala Asn Ala Lys Ile Val Asp Val Ser
                20                  25                  30 aaa gaa gaa aac tca aaa cat cta gaa gag cta aat atc att aca cct     144
Lys Glu Glu Asn Ser Lys His Leu Glu Glu Leu Asn Ile Ile Thr Pro
            35                  40                  45 aat ggt aat ata cct acg ctt agc aca gat gat ttt gca gtg tat agg     192
Asn Gly Asn Ile Pro Thr Leu Ser Thr Asp Asp Phe Ala Val Tyr Arg
        50                  55                  60 ctt agt gtg att ata gaa gct ata gag gat cta tat ccc ttt cct ccg     240
Leu Ser Val Ile Ile Glu Ala Ile Glu Asp Leu Tyr Pro Phe Pro Pro
65                  70                  75                  80 atg ttt cca gta ttt cca aaa cag cga gct aat gca aga ata ttg tta     288
Met Phe Pro Val Phe Pro Lys Gln Arg Ala Asn Ala Arg Ile Leu Leu
                85                  90                  95 gaa tat gtt aat aag acg ttt cta caa aat att att aaa tta caa agt     336
Glu Tyr Val Asn Lys Thr Phe Leu Gln Asn Ile Ile Lys Leu Gln Ser
            100                 105                 110 cct gat ttg gat gaa aaa caa gct aac gaa ata aaa atg cta atg caa     384
Pro Asp Leu Asp Glu Lys Gln Ala Asn Glu Ile Lys Met Leu Met Gln
        115                 120                 125 agg gat ata ata agc act tat aag aca ata gtt agt gaa aga gaa gta     432
Arg Asp Ile Ile Ser Thr Tyr Lys Thr Ile Val Ser Glu Arg Glu Val
130                 135                 140 aat gca gaa agt aat cca gat gct caa aat atc aac gta ttg act ctg     480
Asn Ala Glu Ser Asn Pro Asp Ala Gln Asn Ile Asn Val Leu Thr Leu
145                 150                 155                 160 ata ata act ttc gtt ttt tat tat ttc att aag tta aag atc tca ata     528
Ile Ile Thr Phe Val Phe Tyr Tyr Phe Ile Lys Leu Lys Ile Ser Ile
                165                 170                 175
```

```
cct acc aaa gat aaa aac att atc aaa gag atc aaa gaa tta ctt agc      576
Pro Thr Lys Asp Lys Asn Ile Ile Lys Glu Ile Lys Glu Leu Leu Ser
        180                 185                 190 gaa cct aac ttt ata aaa act atc aaa gca aaa gga gct taa              618
Glu Pro Asn Phe Ile Lys Thr Ile Lys Ala Lys Gly Ala
        195                 200                 205
```

<210> SEQ ID NO 26
<211> LENGTH: 205
<212> TYPE: PRT
<213> ORGANISM: Francisella tularensis

<400> SEQUENCE: 26

```
Met Leu Leu Tyr Thr Lys Lys Asp Asp Ile Tyr Ser Asp Ile Val Arg
1               5                   10                  15

Met Ile Leu Leu Ile Lys Gly Ala Asn Ala Lys Ile Val Asp Val Ser
                20                  25                  30

Lys Glu Glu Asn Ser Lys His Leu Glu Glu Leu Asn Ile Ile Thr Pro
            35                  40                  45

Asn Gly Asn Ile Pro Thr Leu Ser Thr Asp Asp Phe Ala Val Tyr Arg
        50                  55                  60

Leu Ser Val Ile Ile Glu Ala Ile Glu Asp Leu Tyr Pro Phe Pro Pro
65                  70                  75                  80

Met Phe Pro Val Phe Pro Lys Gln Arg Ala Asn Ala Arg Ile Leu Leu
                85                  90                  95

Glu Tyr Val Asn Lys Thr Phe Leu Gln Asn Ile Ile Lys Leu Gln Ser
            100                 105                 110

Pro Asp Leu Asp Glu Lys Gln Ala Asn Glu Ile Lys Met Leu Met Gln
        115                 120                 125

Arg Asp Ile Ile Ser Thr Tyr Lys Thr Ile Val Ser Glu Arg Glu Val
130                 135                 140

Asn Ala Glu Ser Asn Pro Asp Ala Gln Asn Ile Asn Val Leu Thr Leu
145                 150                 155                 160

Ile Ile Thr Phe Val Phe Tyr Tyr Phe Ile Lys Leu Lys Ile Ser Ile
                165                 170                 175

Pro Thr Lys Asp Lys Asn Ile Ile Lys Glu Ile Lys Glu Leu Leu Ser
        180                 185                 190

Glu Pro Asn Phe Ile Lys Thr Ile Lys Ala Lys Gly Ala
        195                 200                 205
```

<210> SEQ ID NO 27
<211> LENGTH: 618
<212> TYPE: DNA
<213> ORGANISM: Francisella tularensis
<220> FEATURE:
<221> NAME/KEY: CDS
<222> LOCATION: (1)..(618)

<400> SEQUENCE: 27

```
ttg ctt tta tac aca aaa aaa gat gat atc tat agc gat ata gtc cgc      48
Met Leu Leu Tyr Thr Lys Lys Asp Asp Ile Tyr Ser Asp Ile Val Arg
1               5                   10                  15 atg atc ctt ctt att aaa gga gct aat gcg aaa att gta gat gtt tct      96
Met Ile Leu Leu Ile Lys Gly Ala Asn Ala Lys Ile Val Asp Val Ser
                20                  25                  30 aaa gaa gaa aat tca aaa cat cta gaa gag cta aat atc att aca cct      144
Lys Glu Glu Asn Ser Lys His Leu Glu Glu Leu Asn Ile Ile Thr Pro
            35                  40                  45 aat ggt aat ata cct acg ctt agc aca gat gat ttt gca gtg tat agg      192
```

```
                                                                          240
ctt agt gtg att ata gaa gct ata gag gat cta tat ccc ttt cct ccg
Leu Ser Val Ile Ile Glu Ala Ile Glu Asp Leu Tyr Pro Phe Pro Pro
65              70                  75                  80

288
atg ttt cca gta ttt cca aaa cag cga gct aat gca aga ata ttg tta
Met Phe Pro Val Phe Pro Lys Gln Arg Ala Asn Ala Arg Ile Leu Leu
                85                  90                  95

336
gaa tat gtt aat aaa acg ttt ctg caa aat att atc aaa tta caa agc
Glu Tyr Val Asn Lys Thr Phe Leu Gln Asn Ile Ile Lys Leu Gln Ser
            100                 105                 110

384
cct gat ttg gat gaa aaa caa gct aac gaa ata aaa atg cta atg caa
Pro Asp Leu Asp Glu Lys Gln Ala Asn Glu Ile Lys Met Leu Met Gln
        115                 120                 125

432
agg gat ata ata agc act tat aag aaa ata gtt agt gaa aga gaa gta
Arg Asp Ile Ile Ser Thr Tyr Lys Lys Ile Val Ser Glu Arg Glu Val
    130                 135                 140

480
aat gca gaa agt aat cca gat gct caa aat ata aat gta ttg act ctg
Asn Ala Glu Ser Asn Pro Asp Ala Gln Asn Ile Asn Val Leu Thr Leu
145                 150                 155                 160

528
ata ata act ttc gtt ttt tat tat ttc att aaa tta aag atc tca ata
Ile Ile Thr Phe Val Phe Tyr Tyr Phe Ile Lys Leu Lys Ile Ser Ile
                165                 170                 175

576
cct acc aaa gat aaa aac att atc aaa gag atc aaa gaa tta ctt agc
Pro Thr Lys Asp Lys Asn Ile Ile Lys Glu Ile Lys Glu Leu Leu Ser
            180                 185                 190

618
gaa cct aac ttt ata aaa act atc aaa gca aaa gga gct taa
Glu Pro Asn Phe Ile Lys Thr Ile Lys Ala Lys Gly Ala
        195                 200                 205
```

<210> SEQ ID NO 28
<211> LENGTH: 205
<212> TYPE: PRT
<213> ORGANISM: Francisella tularensis

<400> SEQUENCE: 28

```
Met Leu Leu Tyr Thr Lys Lys Asp Asp Ile Tyr Ser Asp Ile Val Arg
1               5                   10                  15

Met Ile Leu Leu Ile Lys Gly Ala Asn Ala Lys Ile Val Asp Val Ser
                20                  25                  30

Lys Glu Glu Asn Ser Lys His Leu Glu Glu Leu Asn Ile Ile Thr Pro
            35                  40                  45

Asn Gly Asn Ile Pro Thr Leu Ser Thr Asp Phe Ala Val Tyr Arg
        50                  55                  60

Leu Ser Val Ile Ile Glu Ala Ile Glu Asp Leu Tyr Pro Phe Pro Pro
65              70                  75                  80

Met Phe Pro Val Phe Pro Lys Gln Arg Ala Asn Ala Arg Ile Leu Leu
                85                  90                  95

Glu Tyr Val Asn Lys Thr Phe Leu Gln Asn Ile Ile Lys Leu Gln Ser
            100                 105                 110

Pro Asp Leu Asp Glu Lys Gln Ala Asn Glu Ile Lys Met Leu Met Gln
        115                 120                 125

Arg Asp Ile Ile Ser Thr Tyr Lys Lys Ile Val Ser Glu Arg Glu Val
    130                 135                 140

Asn Ala Glu Ser Asn Pro Asp Ala Gln Asn Ile Asn Val Leu Thr Leu
145                 150                 155                 160

Ile Ile Thr Phe Val Phe Tyr Tyr Phe Ile Lys Leu Lys Ile Ser Ile
                165                 170                 175
```

```
Pro Thr Lys Asp Lys Asn Ile Ile Lys Glu Ile Lys Glu Leu Leu Ser
            180                 185                 190

Glu Pro Asn Phe Ile Lys Thr Ile Lys Ala Lys Gly Ala
            195                 200             205

<210> SEQ ID NO 29
<211> LENGTH: 570
<212> TYPE: DNA
<213> ORGANISM: Francisella tularensis
<220> FEATURE:
<221> NAME/KEY: CDS
<222> LOCATION: (1)..(570)

<400> SEQUENCE: 29 atg atc ctt ctt att aaa gga gct aat gcg aaa att gta gat gtt tct    48
Met Ile Leu Leu Ile Lys Gly Ala Asn Ala Lys Ile Val Asp Val Ser
1               5                   10                  15 aaa gaa gaa aac tca aaa cat cta gaa gag cta aat atc att aca cct    96
Lys Glu Glu Asn Ser Lys His Leu Glu Glu Leu Asn Ile Ile Thr Pro
            20                  25                  30 aat ggt aat ata cct acg ctt agc aca gat gat ttt gca gtg tat agg   144
Asn Gly Asn Ile Pro Thr Leu Ser Thr Asp Asp Phe Ala Val Tyr Arg
        35                  40                  45 ctt agt gtg att ata gaa gct ata gag gat cta tat ccc ttt cct ccg   192
Leu Ser Val Ile Ile Glu Ala Ile Glu Asp Leu Tyr Pro Phe Pro Pro
    50                  55                  60 atg ttt cca gta ttt cca aaa cag cga gct aat gca aga ata ttg tta   240
Met Phe Pro Val Phe Pro Lys Gln Arg Ala Asn Ala Arg Ile Leu Leu
65                  70                  75                  80 gaa tat gtt aat aaa acg ttt ctg caa aat att atc aaa tta caa agc   288
Glu Tyr Val Asn Lys Thr Phe Leu Gln Asn Ile Ile Lys Leu Gln Ser
                85                  90                  95 cct gat ttg gat gaa aaa caa gct aac gaa ata aaa atg cta atg caa   336
Pro Asp Leu Asp Glu Lys Gln Ala Asn Glu Ile Lys Met Leu Met Gln
            100                 105                 110 agg gat ata ata agc act tat aag aaa ata gtt agt gaa aga gaa gta   384
Arg Asp Ile Ile Ser Thr Tyr Lys Lys Ile Val Ser Glu Arg Glu Val
        115                 120                 125 aat gca gaa agt aat cca gat gct caa aat ata aat gta ttg act ctg   432
Asn Ala Glu Ser Asn Pro Asp Ala Gln Asn Ile Asn Val Leu Thr Leu
    130                 135                 140 ata ata act ttc gtt ttt tat tat ttc att aag tta aag atc tca ata   480
Ile Ile Thr Phe Val Phe Tyr Tyr Phe Ile Lys Leu Lys Ile Ser Ile
145                 150                 155                 160 cct acc aaa gat aaa aac att atc aaa gag atc aaa gaa tta ctt agc   528
Pro Thr Lys Asp Lys Asn Ile Ile Lys Glu Ile Lys Glu Leu Leu Ser
                165                 170                 175 gaa cct aac ttt ata aaa act atc aaa gca aaa gga gct taa            570
Glu Pro Asn Phe Ile Lys Thr Ile Lys Ala Lys Gly Ala
            180                 185

<210> SEQ ID NO 30
<211> LENGTH: 189
<212> TYPE: PRT
<213> ORGANISM: Francisella tularensis

<400> SEQUENCE: 30

Met Ile Leu Leu Ile Lys Gly Ala Asn Ala Lys Ile Val Asp Val Ser
1               5                   10                  15

Lys Glu Glu Asn Ser Lys His Leu Glu Glu Leu Asn Ile Ile Thr Pro
            20                  25                  30
```

```
Asn Gly Asn Ile Pro Thr Leu Ser Thr Asp Asp Phe Ala Val Tyr Arg
            35                  40                  45

Leu Ser Val Ile Ile Glu Ala Ile Glu Asp Leu Tyr Pro Phe Pro Pro
    50                  55                  60

Met Phe Pro Val Phe Pro Lys Gln Arg Ala Asn Ala Arg Ile Leu Leu
65                  70                  75                  80

Glu Tyr Val Asn Lys Thr Phe Leu Gln Asn Ile Ile Lys Leu Gln Ser
                85                  90                  95

Pro Asp Leu Asp Glu Lys Gln Ala Asn Glu Ile Lys Met Leu Met Gln
            100                 105                 110

Arg Asp Ile Ile Ser Thr Tyr Lys Lys Ile Val Ser Glu Arg Glu Val
            115                 120                 125

Asn Ala Glu Ser Asn Pro Asp Ala Gln Asn Ile Asn Val Leu Thr Leu
        130                 135                 140

Ile Ile Thr Phe Val Phe Tyr Tyr Phe Ile Lys Leu Lys Ile Ser Ile
145                 150                 155                 160

Pro Thr Lys Asp Lys Asn Ile Ile Lys Glu Ile Lys Glu Leu Leu Ser
                165                 170                 175

Glu Pro Asn Phe Ile Lys Thr Ile Lys Ala Lys Gly Ala
            180                 185

<210> SEQ ID NO 31
<211> LENGTH: 2122
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 31
ggatcctacc atttgtaagt gaaaaaggta ctagtaacgc ttgtttcttt agtgtaaatt      60
ctgctaaaaa agtcgaagaa tttgtagatg gatttgactc agcaaactca agattaattg    120
ctaacctttc ttacactatg tgtatatcga gaatatctca ttatattaaa tgtgtaatta    180
gagataagat tggtagtatt gtggatgtcg agtcgattca aaaaattctt tctgattgga    240
tatcagaatt tgtcaccaca gtctatcaac caacccettt agaaatggcg agatatcctt    300
tcagaaacgt ttctatcgag gttaaaacca taccgggtaa gcctggctgg tattcatgca    360
aaataaatgt aattccccac attcaatttg aaggaatgaa actacaatg actatagata    420 ctaggcttga accagaatta ttcggtacaa ataataacta aaaaaaggag aatgattatg    480
agtgagatga taacaagaca acaggaattc acgcgttggc taacacacac gccattccaa    540
ccaatagttt tctcggcata aagccatgct ctgacgctta aatgcactaa tgccttaaaa    600
aaacattaaa gtctaacaca ctagacttat ttacttcgta attaagtcgt taaaccgtgt    660
gctctacgac caaagtata aaacctttaa gaactttctt ttttcttgta aaaaagaaa     720 ctagataaat ctctcatatc ttttattcaa taatcgcatc agattgcagt ataaatttaa    780
cgatcactca tcatgttcat atttatcaga gctcgtgcta taattatact aattttataa    840
ggaggaaaaa ataagagggg ttataatgaa cgagaaaaat ataaaacaca gtcaaaactt    900
tattacttca aaacataata tagataaaat aatgacaaat ataagattaa atgaacatga    960
taatatcttt gaaatcggct caggaaaagg gcattttacc cttgaattag tacagaggtg    1020
taatttcgta actgccattg aaatagacca taaattatgc aaaactacag aaaataaact    1080
tgttgatcac gataatttcc aagttttaaa caaggatata ttgcagttta aatttcctaa    1140
```

```
aaaccaatcc tataaaatat ttggtaatat accttataac ataagtacgg atataatacg    1200
caaaattgtt tttgatagta tagctgatga gatttattta atcgtggaat acgggtttgc    1260
taaaagatta ttaaatacaa aacgctcatt ggcattattt ttaatggcag aagttgatat    1320
ttctatatta agtatggttc aagagaata ttttcatcct aaacctaaag tgaatagctc     1380
acttatcaga ttaaatagaa aaaatcaag aatatcacac aaagataaac agaagtataa    1440
ttatttcgtt atgaaatggg ttaacaaaga atacaagaaa atatttacaa aaaatcaatt    1500
taacaattcc ttaaaacatg caggaattga cgatttaaac aatattagct ttgaacaatt    1560
cttatctctt ttcaatagct ataaattatt taataagtaa ctgcagggat atattgcagc    1620
tgcatagtaa gatcggagtt gattctaatg tttctagaaa ggatttattg ggaagatggt    1680
ttaagattag atagcgatat tttagataag tcaaatctat ctgttttaga aaggttaagc    1740
accgcaagct atttgccagc taatctaata agggaatcgt tagctttgat ttagatgttg    1800
aaagtttgca gacaggtctt atccttataa aagatcttaa attgtactta gatgaaaaaa    1860
attttgtttt ttatgataag tcttatccgt tatctttaca aataatgact gataagttaa    1920
gtgatgaaat acccttattt ctgaatatca gagagaaagt aattgaaaaa atgggggtta    1980
aatatatcta taatcaattg tcattatcat tagagcatag ctatggtttt aaacatagca    2040
tccaaattgc attatttagg ctagatagag ggcgattagt accagaaatt tatgactttc    2100
cgctattaac tcttaaaagc tt                                             2122
```

<210> SEQ ID NO 32
<211> LENGTH: 2331
<212> TYPE: DNA
<213> ORGANISM: Artificial Sequence
<220> FEATURE:
<223> OTHER INFORMATION: Description of Artificial Sequence: Synthetic Primer

<400> SEQUENCE: 32

```
ggatccaaca cgtcagtcag agtacgaaat ggtaaagtca agagggttag cagcattgat      60
aggaatgcta atactgaagc tatcttacaa agtatttatg ataatataat tgcgtttgat     120
gaacaagatt tagaaagact atttacgggg tttaggattt taaaacaaga aaattcgaca     180
aacactaata aagccgtttt caatattggt ttaacatatc atccaataac taataatgct     240
tttgttgaat ttaataagga tcaacaaagt ttattgtact catataataa tttaagcaaa     300
gatgcgtatg tcacaaaaat taaaagtata gttgatgcta agttgctttt aaaccttagt     360
tttgaacatg aagagattag aagttcacaa ggttttagtg tcttagcaac tgtaccagct     420
agaggatatt ctatagatga tttaaataga agtatagac caatgatctg ggtttaaatt     480
tagctgtata aacattgtgt tattggcgtt gttaaggtaa cttgcttata aggtgttgta     540
aaaaaaggac aataagatgg caaaaaataa atcccaaat tcaaggttga tgataaatta     600
tgaagaattc acgcgttggc taacacacac gccattccaa ccaatagttt tctcggcata     660
aagccatgct ctgacgctta aatgcactaa tgccttaaaa aaacattaaa gtctaacaca     720
ctagacttat ttacttcgta attaagtcgt taaaccgtgt gctctacgac caaaagtata     780
aaacctttaa gaactttctt ttttcttgta aaaaagaaa ctagataaat ctctcatatc     840
ttttattcaa taatcgcatc agattgcagt ataaatttaa cgatcactca tcatgttcat     900 attatatcaga gctcgtgcta taattatact aattttataa ggaggaaaaa ataaagaggg    960
ttataatgaa cgagaaaaat ataaaacaca gtcaaaactt tattacttca aaacataata   1020
```

```
tagataaaat aatgacaaat ataagattaa atgaacatga taatatcttt gaaatcggct    1080
caggaaaagg gcattttacc cttgaattag tacagaggtg taatttcgta actgccattg    1140
aaatagacca taaattatgc aaaactacag aaaataaact tgttgatcac gataatttcc    1200
aagttttaaa caaggatata ttgcagttta aatttcctaa aaaccaatcc tataaaatat    1260
ttggtaatat accttataac ataagtacgg atataatacg caaaattgtt tttgatagta    1320
tagctgatga gatttattta atcgtggaat acgggtttgc taaaagatta ttaaatacaa    1380
aacgctcatt ggcattattt ttaatggcag aagttgatat ttctatatta agtatggttc    1440
caagagaata ttttcatcct aaacctaaag tgaatagctc acttatcaga ttaaatagaa    1500
aaaaatcaag aatatcacac aaagataaac agaagtataa ttatttcgtt atgaaatggg    1560
ttaacaaaga atacaagaaa atatttacaa aaaatcaatt taacaattcc ttaaaacatg    1620
caggaattga cgatttaaac aatattagct ttgaacaatt cttatctctt ttcaatagct    1680
ataaattatt taataagtaa ctccagctgc aggattcctg ctttgacaaa ttatacgatt    1740
aaagactctt gtgatgctgc tgagtctcaa gacttaagta atcaacaagt agatgataag    1800
tagagaggat tttgttatga caataaataa attaagtctc actgatgaac ttttaaataa    1860
ttttggggga tctacagaag ttgatagtgt actcaaaaat atagattttg atgtttcaga    1920
tgatgcttct aaagttttat cttatctac tgactacaat gctagaaacc ttatggcgct    1980
atctttggta ttagcaaata atgataatat aaataattac aatcaaaaat atattccaaaa   2040 agttattaca gttattgata agctgattga tttacaagtt aactctatta tatctaatga    2100
tgagtttaga gcacttgagc aagaatggct aaaggtgcaa gaggtttgtc aagaagacta    2160
tgataatgtt gaagtaagta tattagatgt aaaaaaagaa gagctacaat atgatttcga    2220
gagaaattta tatgatatat ctagtagtga cttttttcaaa aaagtatatg tttcagaatt    2280
tgatcaatat ggtggcgaac cttatggcgc aatattagga ttgtagtcga c             2331
```

<210> SEQ ID NO 33
<211> LENGTH: 2318
<212> TYPE: DNA
<213> ORGANISM: Artificial Sequence
<220> FEATURE:
<223> OTHER INFORMATION: Description of Artificial Sequence: Synthetic Primer

<400> SEQUENCE: 33

```
ggatcccata tgttctagaa aggatttatt gggaagatgg tttaagatta gatagcgata      60
ttttagataa gtcaaatcta tctgttttag aaaggttaag caccgcaagc tatttgccag     120
ctaatctaat aagggaatcg ttagctttga tttagatgtt gaaagtttgc agacaggtct     180
tatccttata aaagatctta aattgtactt agatgaaaaa aattttgttt tttatgataa     240
gtcttatccg ttatctttac aaataatgac tgataagtta agtgatgaaa tacccttatt     300
tctgaatatc agagagaaag taattgaaaa aaatgggggtt aaatatatct ataatcaatt    360
gtcattatca ttagagcata gctatggttt taaacatagc atccaaattg cattatttag    420
gctagataga gggcgattag taccagaaat ttatgacttt ccgctattaa ctcttaatca    480
ttattattta ggtgatattt ttgtaaaact taataggact gttctgaac taaagtctt      540 taatcgcttt gttttttcag cttcaagatc ttatgcgtca atattacttg tattttgat    600 taataaatta gaattcacgc gttggctaac acacacgcca ttccaaccaa tagttttctc    660
ggcataaagc catgctctga cgcttaaatg cactaatgcc ttaaaaaaac attaaagtct    720
```

| aacacactag acttatttac ttcgtaatta agtcgttaaa ccgtgtgctc tacgaccaaa | 780 |
| agtataaaac ctttaagaac tttctttttt cttgtaaaaa aagaaactag ataaatctct | 840 |
| catatctttt attcaataat cgcatcagat tgcagtataa atttaacgat cactcatcat | 900 |
| gttcatattt atcagagctc gtgctataat tatactaatt ttataaggag gaaaaaataa | 960 |
| agagggttat aatgaacgag aaaaatataa aacacagtca aaactttatt acttcaaaac | 1020 |
| ataatataga taaaataatg acaaatataa gattaaatga acatgataat atctttgaaa | 1080 |
| tcggctcagg aaaagggcat tttacccttg aattagtaca gaggtgtaat ttcgtaactg | 1140 |
| ccattgaaat agaccataaa ttatgcaaaa ctacagaaaa taaacttgtt gatcacgata | 1200 |
| atttccaagt tttaaacaag gatatattgc agtttaaatt tcctaaaaac caatcctata | 1260 |
| aaatatttgg taatatacct tataacataa gtacggatat aatacgcaaa attgttttg | 1320 |
| atagtatagc tgatgagatt tatttaatcg tggaatacgg gtttgctaaa agattattaa | 1380 |
| atacaaaacg ctcattggca ttattttaa tggcagaagt tgatatttct atattaagta | 1440 |
| tggttccaag agaatatttt catcctaaac ctaaagtgaa tagctcactt atcagattaa | 1500 |
| atagaaaaaa atcaagaata tcacacaaag ataaacagaa gtataattat ttcgttatga | 1560 |
| aatgggttaa caaagaatac aagaaaatat ttacaaaaaa tcaatttaac aattccttaa | 1620 |
| aacatgcagg aattgacgat ttaaacaata ttagctttga acaattctta tctcttttca | 1680 |
| atagctataa attatttaat aagtaactgc agaatattgt aactttgtct ctttcaggag | 1740 |
| taaaactggt tgacgttgaa tgttctatga ttaattttac aactagattt gataatatcg | 1800 |
| atgcaatata tgaaattcaa aaaggttctg agtgggattt tatattagcg gatagtagtg | 1860 |
| cggttttac ggcttttgaa ggtagtgaga attttgattt ctttatagcc ttttcttaac | 1920 |
| tagagttata ttatagtaat tttctttca taatgaggga tagcccagcc atcagctatg | 1980 |
| cgttcgagat ttacgcctaa aaatttacct ttatcataat tgctacaatt attattgtct | 2040 |
| gtatctataa aaatagatcc ttcactaagt gataaatata atcctgaaga tacaaaccaa | 2100 |
| ttatatataa cttgtgagta gtaagtttca tatttattat ttttaaataa actcaaacat | 2160 |
| atatttattg cttctggtgg agattcttct ttatcatgtt tatataatat tgttaaatct | 2220 |
| ttagctgatt tagcattgat tggcactgac aagtaatagt aaatacgact aagaggttct | 2280 |
| ctaactaatt cagttatata aatacaatta ttaagctt | 2318 |

<210> SEQ ID NO 34
<211> LENGTH: 2114
<212> TYPE: DNA
<213> ORGANISM: Artificial Sequence
<220> FEATURE:
<223> OTHER INFORMATION: Description of Artificial Sequence:  Synthetic
     Primer

<400> SEQUENCE: 34

| ggatccgagc tctaatcgag tatgatgaag aacttaaacc agctcttcgt gaagcaggtt | 60 |
| ttgttactcg tgacccacgt aaagttgagc gtaagaaatt tggtcttaga aaagctcgta | 120 |
| gaagaagaca attctctaag cgttaatcta ttttatatta cctttctatt attctttttt | 180 |
| attttattac taggaggata caatcttgct tttatacaca aaaaaagatg atatctatag | 240 |
| cgatatagtc cgcatgatcc ttcttattaa aggggctaat gcgaaaattg tagatgtttc | 300 |
| taaagaagaa aactcaaaac atctagaaga gctaaatatc attacaccta atggtaatat | 360 |
| acctacgctt agcacagatg attttgcagt gtataggctt agtgtgatta tagaagctat | 420 |

```
agaggatcta tatcccttc ctccgatgtt tccagtattt ccaaaacagc gagctaatgc      480
aagaatattg ttagaatatg ttaatgaatt cacgcgttgg ctaacacaca cgccattcca      540
accaatagtt ttctcggcat aaagccatgc tctgacgctt aaatgcacta atgccttaaa      600
aaaacattaa agtctaacac actagactta tttacttcgt aattaagtcg ttaaaccgtg      660
tgctctacga ccaaaagtat aaaacccttta agaactttct ttttcttgt aaaaaaagaa      720 actagataaa tctctcatat cttttattca ataatcgcat cagattgcag tataaattta      780
acgatcactc atcatgttca tatttatcag agctcgtgct ataattatac taattttata      840
aggaggaaaa aataaagagg gttataatga acgagaaaaa tataaaacac agtcaaaact      900
ttattacttc aaaacataat atagataaaa taatgacaaa tataagatta aatgaacatg      960
ataatatctt tgaaatcggc tcaggaaaag ggcattttac ccttgaatta gtacagaggt     1020
gtaatttcgt aactgccatt gaaatagacc ataaattatg caaaactaca gaaaataaac     1080
ttgttgatca cgataatttc caagttttaa acaaggatat attgcagttt aaatttccta     1140 aaaccaatc ctataaaata tttggtaata taccttataa cataagtacg gatataatac     1200
gcaaaattgt ttttgatagt atagctgatg agatttattt aatcgtggaa tacgggtttg     1260
ctaaaagatt attaaataca aaacgctcat tggcattatt tttaatggca gaagttgata     1320
tttctatatt aagtatggtt ccaagagaat attttcatcc taaacctaaa gtgaatagct     1380
cacttatcag attaaataga aaaaaatcaa gaatatcaca caaagataaa cagaagtata     1440
attatttcgt tatgaaatgg gttaacaaag aatacaagaa aatatttaca aaaaatcaat     1500
ttaacaattc cttaaaacat gcaggaattg acgatttaaa caatattagc tttgaacaat     1560
tcttatctct tttcaatagc tataaattat ttaataagta actgcagaaa gcaaaaggag     1620
cttaatatgg ctatgcttag agcatatgta gttaaagcta catacaactg gctagttgat     1680
catggattta caccttatgt tttagttgat actgagtatg aaggtgttat agtaccagca     1740
aactatattg atgaagataa aaaaatactt ttagatttat ctcctcaagc aatacaagat     1800
ttagttatag atgataatca tattagcttt gctgcaacgt ttgatagtga gccaatgtct     1860
ataaatattc ctatcgaggc tgtcttagaa gtattttcta aagaaacaga gcaaggaatg     1920
tatgctcgcg aatttggtta tggaattaat atcaatgaag gcgaagatga tgaaactgct     1980
aatcctaaga aattaggaga aactaattca gataacgttc tttcattaga ttaattcttt     2040
actcttaata accttctgta tttatctgta attataggca aatatcctac tataaaactc     2100
aatggtataa gctt                                                       2114
```